(12) United States Patent
Longo

(10) Patent No.: US 8,865,646 B2
(45) Date of Patent: Oct. 21, 2014

(54) DIETARY COMPOSITIONS AND METHODS FOR PROTECTION AGAINST CHEMOTHERAPY, RADIOTHERAPY, OXIDATIVE STRESS, AND AGING

(75) Inventor: Valter Longo, Los Angeles, CA (US)

(73) Assignee: University of South California, Los Angeles, CA (US)

( * ) Notice: Subject to any disclaimer, the term of this patent is extended or adjusted under 35 U.S.C. 154(b) by 170 days.

(21) Appl. No.: 12/430,058

(22) Filed: Apr. 24, 2009

(65) Prior Publication Data

US 2010/0004309 A1    Jan. 7, 2010

Related U.S. Application Data

(63) Continuation-in-part of application No. 12/058,600, filed on Mar. 28, 2008.

(60) Provisional application No. 60/908,636, filed on Mar. 28, 2007, provisional application No. 60/942,561, filed on Jun. 7, 2007, provisional application No. 61/047,680, filed on Apr. 24, 2008.

(51) Int. Cl.
| | |
|---|---|
| *A01N 61/00* | (2006.01) |
| *A61K 31/00* | (2006.01) |
| *A61K 38/00* | (2006.01) |
| *A61K 9/00* | (2006.01) |
| *A61K 47/18* | (2006.01) |

(52) U.S. Cl.
CPC ............. *A61K 9/0053* (2013.01); *A61K 47/183* (2013.01)
USPC ................ 514/5.5; 514/1; 514/1.1; 514/19.2; 514/19.3

(58) Field of Classification Search
None
See application file for complete search history.

(56) References Cited

U.S. PATENT DOCUMENTS

| | | | |
|---|---|---|---|
| 4,724,234 A | 2/1988 | Cone, Jr. | |
| 5,292,723 A | 3/1994 | Audry et al. | |
| 6,338,856 B1 | 1/2002 | Allen et al. | |
| 2002/0035071 A1 | 3/2002 | Pitha et al. | |
| 2004/0005294 A1 | 1/2004 | Lee | |
| 2004/0121407 A1 | 6/2004 | Distefano et al. | |
| 2005/0245462 A1 | 11/2005 | Tidmarsh | |
| 2005/0250709 A1 | 11/2005 | Khodadoust | |
| 2005/0266438 A1 | 12/2005 | Spindler et al. | |
| 2006/0025337 A1 | 2/2006 | Sinclair et al. | |
| 2006/0073514 A1 | 4/2006 | Dedera et al. | |
| 2006/0233804 A1 | 10/2006 | Deshayes et al. | |
| 2006/0275506 A1* | 12/2006 | Fisher et al. ................... | 424/641 |
| 2007/0009576 A1* | 1/2007 | Stillman ....................... | 424/439 |

FOREIGN PATENT DOCUMENTS

| | | |
|---|---|---|
| EP | 0 232 652 A1 | 8/1987 |
| EP | 0 560 989 A1 | 9/1993 |
| GB | 2 029 220 A | 3/1980 |
| WO | 2008/123298 A1 | 12/2009 |

OTHER PUBLICATIONS

International search report for corresponding PCT application PCT/US09/41736 lists the references above, Nov. 24, 2009.
Supplementary European Search Report dated Aug. 31, 2011 in corresponding EP Appn. No. 09 73 4637, filed Nov. 19, 2010, 1 PG.
Suh et al. Lactate dehydrogenase as a prognostic factor for survival time of terminally ill cancer patients: A preliminary study. European Journal of Cancer 43(6): 1051-1059, Apr. 2007.
Barvick, et al, "Effects of combined chemotherapy on sarcoma 180, with special reference to food intake, body-weight changes, and survival time," J. of Nat'l. Cancer Inst. 15(1): 177-189, Aug. 1954.
Breuss, R., The Breuss Cancer Cure, Alive Books, Burnaby, BC, Canada, Jun. 1995.
Raffaghello et al., "Starvation-dependent differential stress resistance protects normal but not cancer cells against high-dose chemotherapy," PNAS 105(24): 8215-8220, Jun. 17, 2008.
Supplementary European Search Report dated Jan. 25, 2011 in corresponding EP Appn. No. 08733006.4-2107, filed Mar. 28, 2008, 10 pgs.

\* cited by examiner

*Primary Examiner* — Alana Harris Dent
(74) *Attorney, Agent, or Firm* — Brooks Kushman P.C.

(57) ABSTRACT

The present invention relates to dietary compositions comprising reduced level of methionine, tryptophan, all amino acids, or protein, dietary compositions comprising glycerol as a substitute for monosaccharides, disaccharides, and polysaccharides, and hypocaloric or calorie free diets with reduced level of energy, carbohydrates, or protein. Also disclosed are methods of using these compositions and diets, as well as fasting, to protect subjects against chemotherapy, radiotherapy, oxidative stress, or aging.

9 Claims, 43 Drawing Sheets

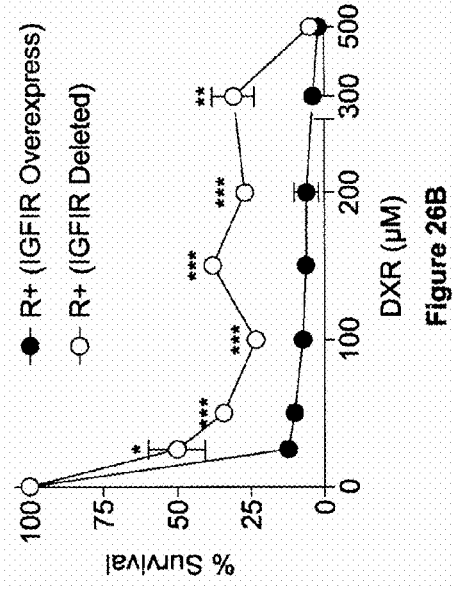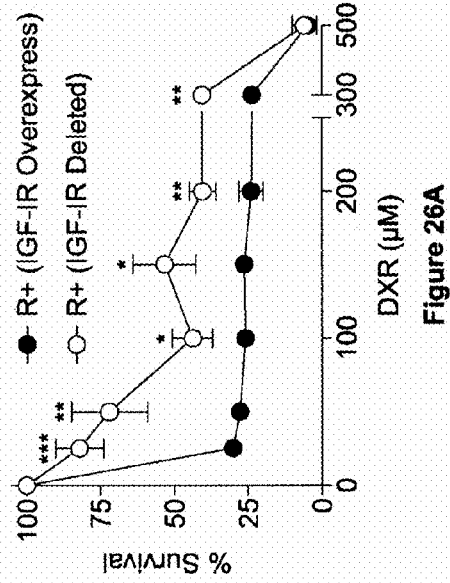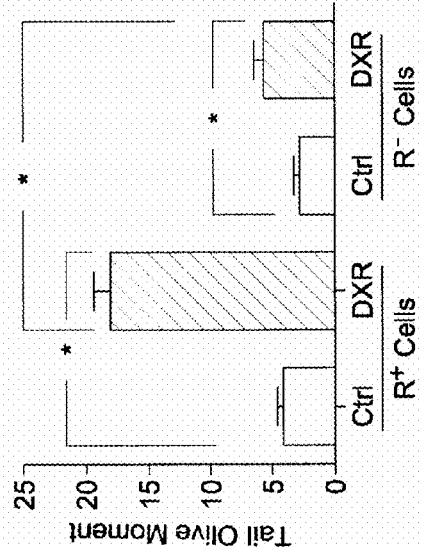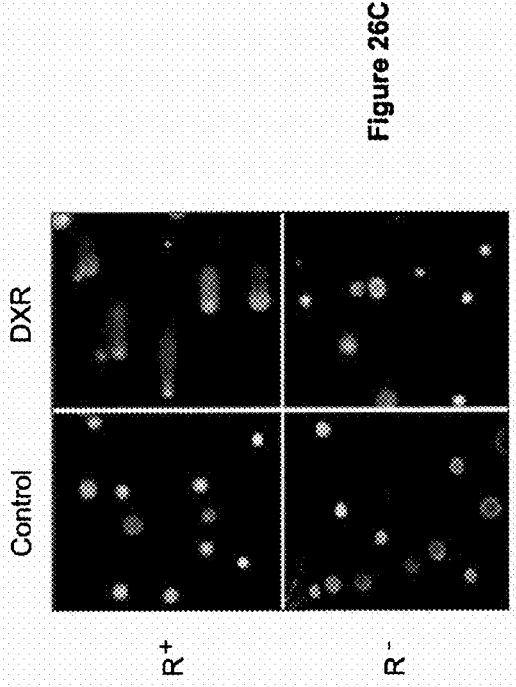
Figure 26A
Figure 26B
Figure 26C
Figure 26D

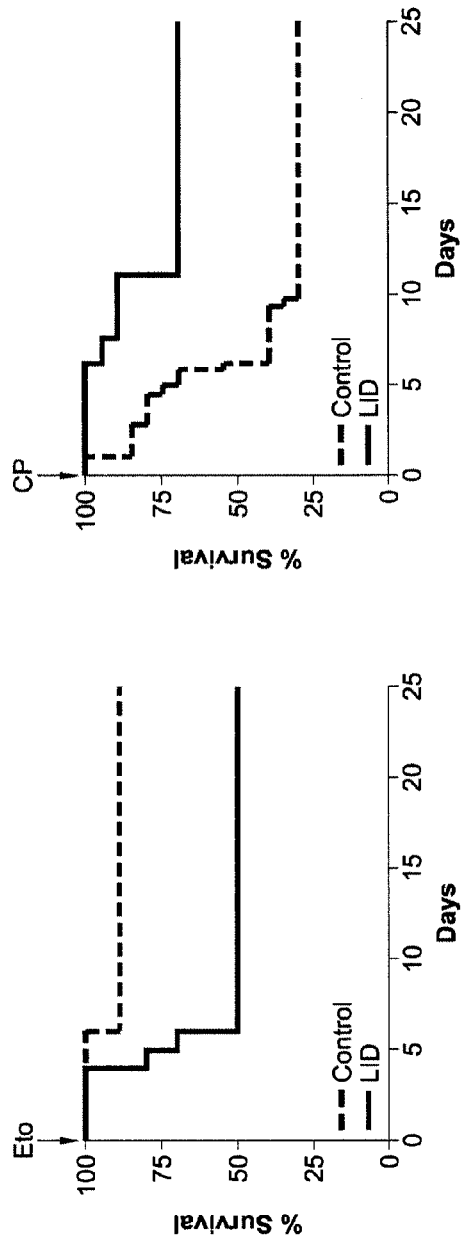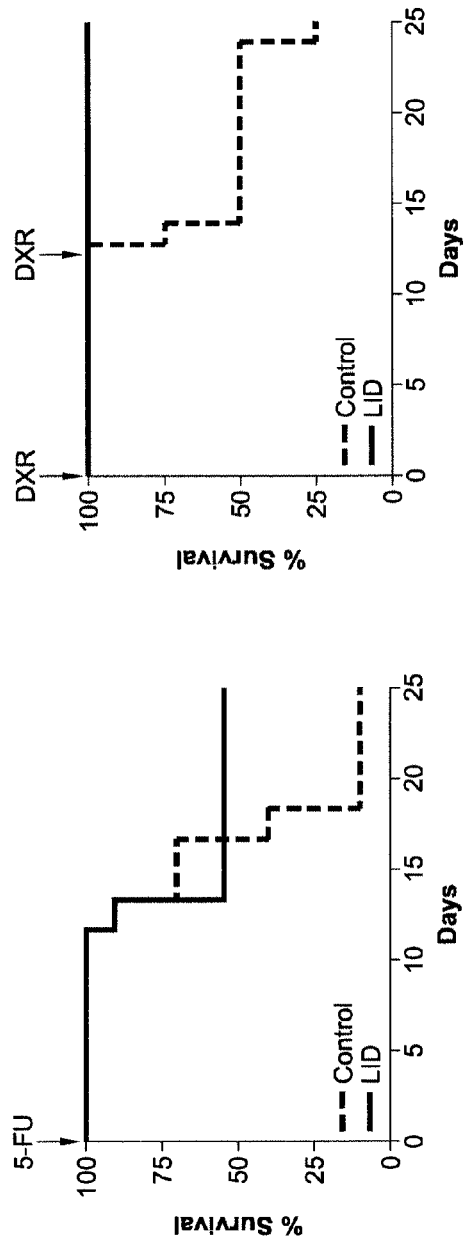

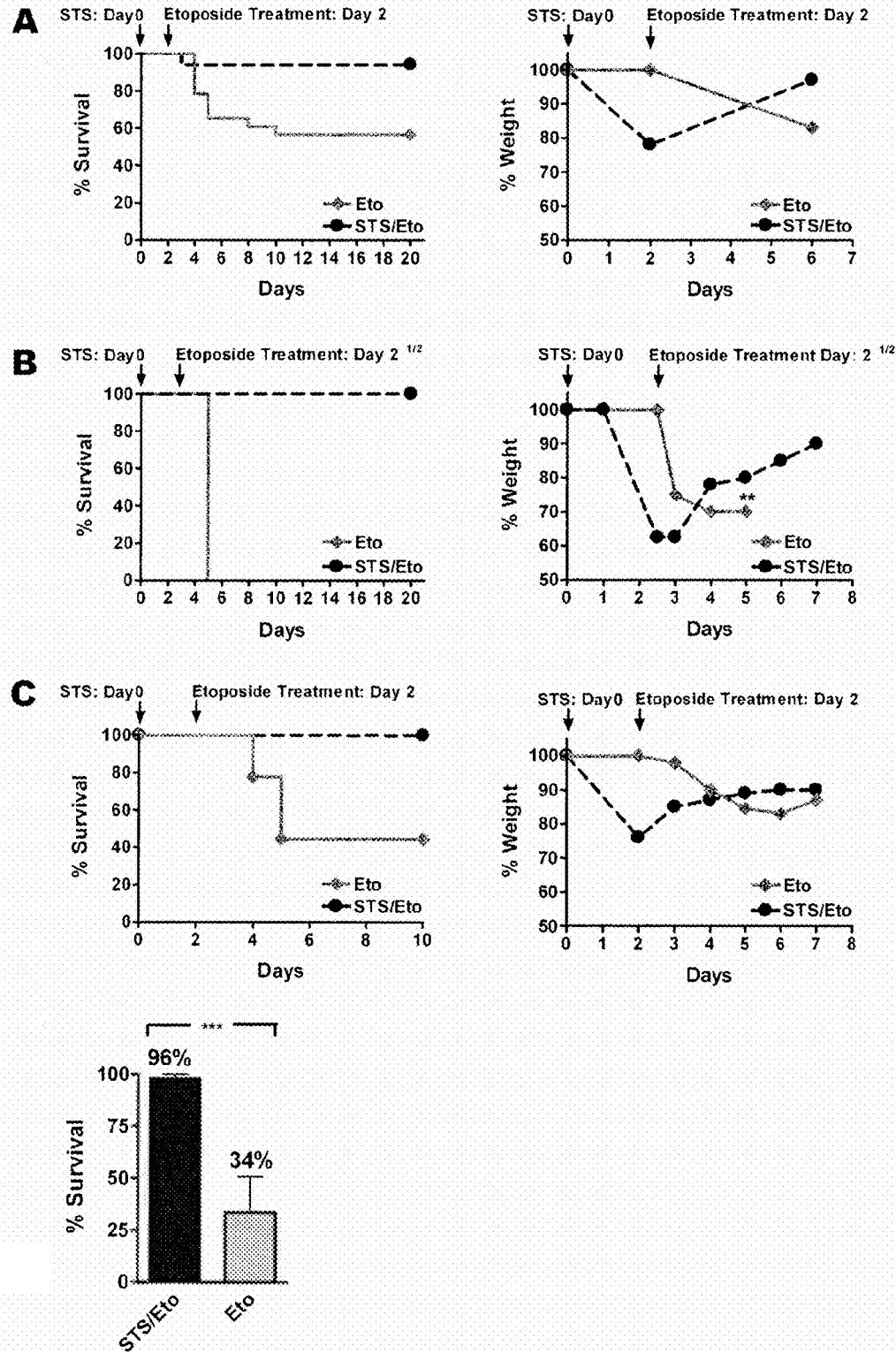
Figure 33 A-D

US 8,865,646 B2

DIETARY COMPOSITIONS AND METHODS FOR PROTECTION AGAINST CHEMOTHERAPY, RADIOTHERAPY, OXIDATIVE STRESS, AND AGING

RELATED APPLICATIONS

This application is a continuation-in-part application of U.S. application Ser. No. 12/058,600, filed Mar. 28, 2008, now U.S. Pat. No. 8,211,700, issued Jul. 3, 2012, which claims priority to U.S. Provisional Application Ser. No. 60/908,636, filed Mar. 28, 2007, now expired, and U.S. Provisional Application Ser. No. 60/942,561, filed Jun. 7, 2007, now expired. The present application also claims priority to U.S. Provisional Application Ser. No. 61/047,680, filed on Apr. 24, 2008, now expired. The contents of U.S. application Ser. No. 12/058,600, now U.S. Pat. No. 8,211,700, and U.S. Provisional Application Ser. Nos. 60/908,636, 60/942,561, and 61/047,680 are incorporated herein by reference in their entirety.

FUNDING

This invention was made with support in part by grants from the National Institutes of Health, AG20642, AG025135, GM075308, and Neurosciences Blueprint. Therefore, the U.S. government has certain rights.

FIELD OF THE INVENTION

The present invention relates in general to treatment of diseases. More specifically, the invention provides dietary compositions and methods for protection against chemotherapy, radiotherapy, oxidative stress, and aging.

BACKGROUND OF THE INVENTION

Modern chemotherapy can improve the quality of life of cancer patients via palliation of cancer-related symptoms, and can significantly extend survival in many malignancies as well. However, the inevitable toxic side-effects frequently limit dose intensity and frequency of drugs administration. For instance, the use of doxorubicin or cisplatin can effectively treat many malignancies, but the drug-induced cardiotoxicity and nephrotoxicity, respectively, limit their full potential. Thus, reducing undesired toxicity by selectively protecting normal cells without compromising cancer targeting would prove beneficial to chemotherapy and enhance clinical outcome.

SUMMARY OF THE INVENTION

The present invention relates to novel dietary compositions and methods useful for protection against chemotherapy, radiotherapy, oxidative stress, and aging.

Accordingly, in one aspect, the invention features a dietary composition comprising 0-0.2% (by weight) L-methionine, as well as L-tryptophan, L-isoleucine, L-leucine, L-lysine, L-phenylalanine, L-threonine, and L-valine in the amount of at least 0.05% (by weight) each, and no protein. The composition may further comprise one or more amino acids selected from the group consisting of L-alanine, L-asparagine, L-aspartic acid, L-cysteine, L-glutamatic acid, L-glutamine, L-glycine, L-proline, L-serine, L-tyrosine, L-arginine, and L-histidine.

In another aspect, the invention features a dietary composition comprising 0-0.2% (by weight) L-tryptophan, as well as L-methionine, L-isoleucine, L-leucine, L-lysine, L-phenylalanine, L-threonine, L-valine in the amount of at least 0.05% (by weight) each, and no protein. The composition may further comprise one or more amino acids selected from the group consisting of L-alanine, L-asparagine, L-aspartic acid, L-cysteine, L-glutamatic acid, L-glutamine, L-glycine, L-proline, L-serine, L-tyrosine, L-arginine, and L-histidine.

In still another aspect, the invention features a dietary composition comprising L-methionine, L-tryptophan, L-isoleucine, L-leucine, L-lysine, L-phenylalanine, L-threonine, L-valine, L-alanine, L-asparagine, L-aspartic acid, L-cysteine, L-glutamatic acid, L-glutamine, L-glycine, L-proline, L-serine, L-tyrosine, L-arginine, and L-histidine in the amount of 0-0.2% (by weight) each, and no protein.

In yet another aspect, the invention features a dietary composition comprising glycerol as a substitute for monosaccharides, disaccharides, and polysaccharides.

Also within the invention is a method of protecting an animal or human against chemotherapy, radiotherapy, oxidative stress, or aging. The method comprises administering a composition of the invention to an animal or human, thereby protecting the animal or human against chemotherapy, radiotherapy, oxidative stress, or aging. The method may further comprise exposing the animal or human to the chemotherapy, radiotherapy, or oxidative stress. In some embodiments, the composition is administered to the animal or human for 3-10 consecutive days prior to the exposing step, 24 hours following the exposing step, or a combination thereof. In some embodiments, the composition is administered every third meal or every 3-10 days to protect the animal or human against aging.

In addition, the invention features a hypocaloric or calorie free diet comprising dietary materials capable of providing nutrition to a human subject while providing no more than 813-957 kcal total energy, no more than half of which is in carbohydrates if the carbohydrates are present in the dietary materials, wherein the dietary materials include no more than 30-36 g protein. In some embodiments, the dietary materials are capable of providing no more than 700 kcal total energy.

Moreover, the invention provides a method of protecting an animal or human against chemotherapy, radiotherapy, oxidative stress, or aging by administering to an animal or human a diet capable of providing nutrition while providing no more than 11 kcal energy per kg body weight of the animal or human per day, and no more than 0.4 g protein per kg body weight of the animal or human per day, wherein no more than half of the energy is in carbohydrates if the carbohydrates are present in the diet. In some embodiments, the diet is capable of providing no more than 700 kcal total energy per day. The method may further comprise exposing the animal or human to the chemotherapy, radiotherapy, or oxidative stress. In some embodiments, the diet is administered to the animal or human for 3-10 consecutive days prior to the exposing step, 24 hours following the exposing step, or a combination thereof. In some embodiments, the diet is administered every third meal or every 3-10 days to protect the animal or human against aging.

The invention further provides a method of protecting an animal or human against chemotherapy. The method comprises fasting an animal or human suffering from cancer for 48-140 hours prior to one round of chemotherapy, 4-56 hours following the chemotherapy, or a combination thereof; and exposing the animal or human to the chemotherapy. In some embodiments, the animal or human is fasted for no more than 180 hours prior to and following one round of chemotherapy.

The above-mentioned and other features of this invention and the manner of obtaining and using them will become more apparent, and will be best understood, by reference to the following description, taken in conjunction with the accompanying drawings. The drawings depict only typical embodiments of the invention and do not therefore limit its scope.

BRIEF DESCRIPTION OF THE FIGURES

FIG. 26. $R^+$ and $R^-$ cells were grown to confluence and treated with DXR (0-500 μM) in DMEM/F12 supplemented with 10% FBS for (A) 24 hours or (3) 48 hours. Viability was determined by the relative degree of MTT reduction compared to untreated; mean±SD. * P<0.05,  P<0.01, * P<0.001 by Student's t test; $R^+$ vs. $R^-$ cells at same DXR concentration. (C) Comet assay. Cells overexpressing IGF-IR or with IGF-IR deficiency ($R^+$ and $R^-$) were treated with 50 μM DXR for 1 hour. Significant DNA damages were observed in the DXR treated $R^+$ cells, while $R^-$ cells were protected from DXR induced DNA damage.  P<0.01, ** P<0.0001 by Student's t test; $R^+$ control vs. $R^+$ DXR; $R^-$ control vs. $R^-$ DXR; $R^+$ DXR vs. $R^-$ DXR. Similar results were obtained from two independent experiments. Representative experiment is shown.

FIG. 28. Stress resistance testing in LID mice with various high-dose chemotherapeutic drugs. LID and control mice received (A) a single injection of 100 mg/kg etoposide (Eto, P=0.064), (B) a single injection of 500 mg/kg CP (P=0.001), (C) a single injection of 400 mg/kg 5-fluorouracil (5-FU, P=0.148), (D) two injections of doxorubicin (DXR). The first injection of 20 mg/kg was given on day zero, and the second injection of 28 mg/kg was given on day 22 (P=0.022). Toxicity evaluated by percent survival is shown. P values by Peto's log rank test.

DETAILED DESCRIPTION OF THE INVENTION

Figure 1:
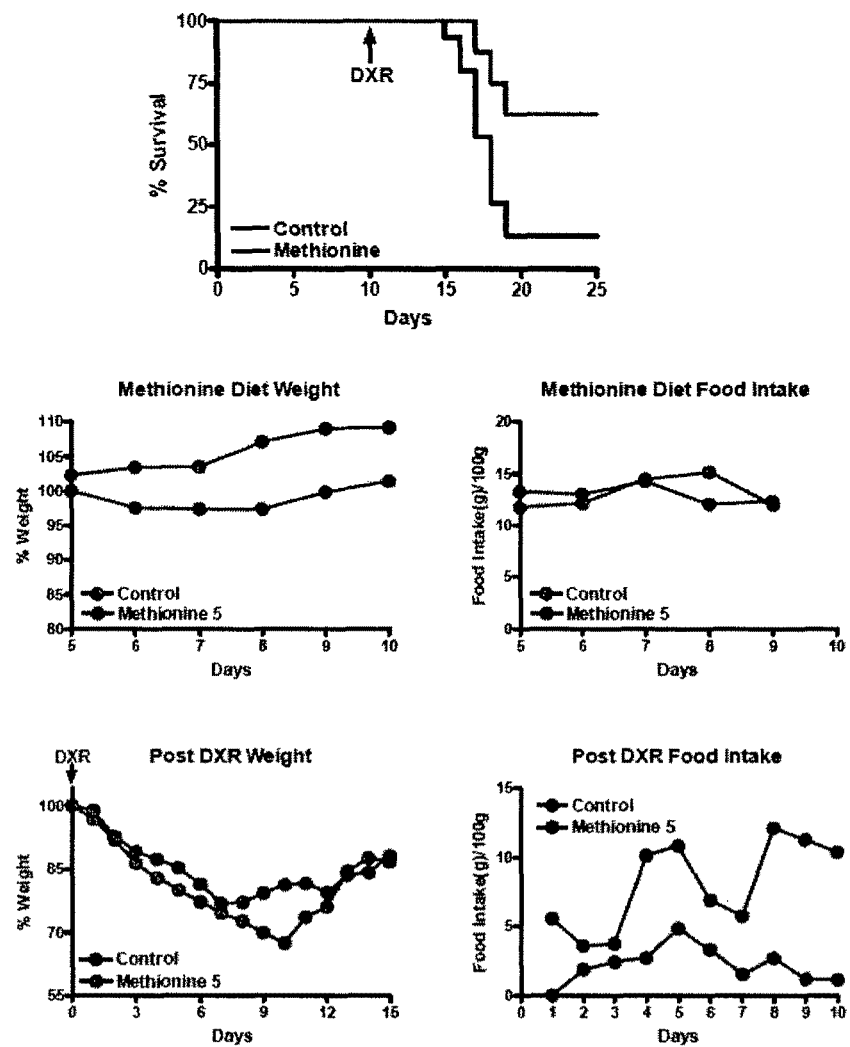
FIG. 1. Graph of (A) % survival, (B) methionine diet body weight %, (C) methionine food intake, (D) post treatment body weight %, and (E) post treatment food intake as a function of days. Mice were treated with a low methionine amino acid mix (LMA1) before treatment with doxorubicin.

The present invention is based, at least in part, upon the unexpected discovery that dietary compositions comprising reduced level of methionine, tryptophan, all amino acids, or protein, dietary compositions comprising glycerol as a substitute for monosaccharides, disaccharides, and polysaccharides, and hypocaloric or calorie free diets with reduced level of energy, carbohydrates, or protein, as well as fasting, can be used to protect subjects against chemotherapy, radiotherapy, oxidative stress, or aging.

More specifically, one dietary composition of the invention contains 0-0.2% (e.g., 0.02%, 0.05%, 0.1%, or 0.15%) by weight L-methionine and at least 0.05% (e.g., 0.1%, 0.5%, 1%, or 2%) by weight of each of L-tryptophan, L-isoleucine, L-leucine, L-lysine, L-phenylalanine, L-threonine, and L-valine, but no protein. In some embodiments, the composition also contains one or more amino acids selected from the group consisting of L-alanine, L-asparagine, L-aspartic acid, L-cysteine, L-glutamatic acid, L-glutamine, L-glycine, L-proline, L-serine, L-tyrosine, L-arginine, and L-histidine, e.g., each in the amount of at least 0.05% (e.g., 0.1%, 0.5%, 1%, or 2%) by weight. In some embodiments, the composition contains a normal amount of each of L-tryptophan, L-isoleucine, L-leucine, L-lysine, L-phenylalanine, L-threonine, L-valine, L-alanine, L-asparagine, L-aspartic acid, L-cysteine, L-glutamatic acid, L-glutamine, L-glycine, L-proline, L-serine, L-tyrosine, L-arginine, and L-histidine.

A second dietary composition of the invention contains 0-0.2% (e.g., 0.02%, 0.05%, 0.1%, or 0.15%) by weight L-tryptophan and at least 0.05% (e.g., 0.1%, 0.5%, 1%, or 2%) by weight of each of L-methionine, L-isoleucine, L-leucine, L-lysine, L-phenylalanine, L-threonine, L-valine, but no protein. In some embodiments, the composition also contains one or more amino acids selected from the group consisting of L-alanine, L-asparagine, L-aspartic acid, L-cysteine, L-glutamatic acid, L-glutamine, L-glycine, L-proline, L-serine, L-tyrosine, L-arginine, and L-histidine, e.g., each in the amount of at least 0.05% (e.g., 0.1%, 0.5%, 1%, or 2%) by weight. In some embodiments, the composition contains a normal amount of each of L-methionine, L-isoleucine, L-leucine, L-lysine, L-phenylalanine, L-threonine, L-valine, L-alanine, L-asparagine, L-aspartic acid, L-cysteine, L-glutamatic acid, t-glutamine, L-glycine, L-proline, L-serine, L-tyrosine, L-arginine, and L-histidine.

A third dietary composition of the invention contains L-methionine, L-tryptophan, L-isoleucine, L-leucine, L-lysine, L-phenylalanine, L-threonine, L-valine, L-alanine, L-asparagine, L-aspartic acid, L-cysteine, L-glutamatic acid, L-glutamine, L-glycine, L-proline, L-serine, L-tyrosine, L-arginine, and L-histidine, each in the amount of 0-0.2% (e.g., 0.02%, 0.05%, 0.1%, or 0.15%) by weight, but no protein.

A fourth dietary composition of the invention contains glycerol as a substitute for monosaccharides (e.g., glucose), disaccharides, and polysaccharides.

A dietary composition of the invention can be used to protect an animal or human against chemotherapy, radiotherapy, oxidative stress, or aging. More specifically, an animal or human may be fed with a dietary composition of the invention. When the animal or human is exposed to chemotherapy, radiotherapy, or oxidative stress, normal cells, but not abnormal cells such as cancer cells, in the animal or human are protected. For example, the composition may be administered to the animal or human for 3-10 consecutive days prior to the animal or human is exposed to chemotherapy, radiotherapy, or oxidative stress. The composition may also be administered to the animal or human for 24 hours following the exposure. Preferably, the composition may be administered to the animal or human for both 3-10 consecutive days prior to the animal or human is exposed to chemotherapy, radiotherapy, or oxidative stress and 24 hours following the exposure. For protection of an animal or human against aging, the composition may be administered every third meal or every 3-10 days.

Examples of chemotherapy include, but are not limited to, etoposide, doxorubicin, cisplatin, 5-FU, gemcitabine, cyclophosphamide, docetaxel, cyclophosphamide, carboplatin, GMZ, and paclitaxel. These drugs may be used individually or in combination.

The invention also provides a hypocaloric or calorie free diet. The diet contains dietary materials capable of providing nutrition to a human subject while providing no more than 813-957 kcal (e.g., no more than 700, 500, 300, or 100 kcal, or 0 kcal) total energy, and no more than 30-36 g (e.g., no more than 20, 10, or 5 g, or 0 g) protein. If carbohydrates are present in the dietary materials, no more than half of the energy is in the carbohydrates.

A diet of the invention can be administered to an animal or human (e.g., once or in 3 portions a day) for protection against chemotherapy, radiotherapy, oxidative stress, or aging. For example, the diet may be administered to the animal or human for 3-10 consecutive days prior to the animal or human is exposed to chemotherapy, radiotherapy, or oxidative stress. The diet may also be administered to the animal or human for 24 hours following the exposure. Preferably, the diet may be administered to the animal or human for both 3-10 consecutive days prior to the animal or human is exposed to chemotherapy, radiotherapy, or oxidative stress and 24 hours following the exposure. For protection of an animal or human against aging, the diet may be administered every third meal or every 3-10 days.

The invention further provides a method of protecting an animal or human against chemotherapy, radiotherapy, oxidative stress, or aging by administering to an animal or human a diet capable of providing nutrition while providing no more than 11 kcal (e.g., no more than 8, 5, or 2 kcal, or 0 kcal) energy per kg body weight of the animal or human per day and no more than 0.4 g (e.g., 0.3, 0.2, or 0.1 g or 0 g) protein per kg body weight of the animal or human per day. If carbohydrates are present in the diet, no more than half of the energy is in the carbohydrates. In some embodiments, the diet is capable of providing no more than 700 kcal (e.g., 600, 400, or 200 kcal or 0 kcal) total energy per day. When the animal or human is exposed to chemotherapy, radiotherapy, or oxidative stress, normal cells, but not abnormal cells such as cancer cells, in the animal or human are protected. For example, the diet may be administered to the animal or human for 3-10 consecutive days prior to the animal or human is exposed to chemotherapy, radiotherapy, or oxidative stress. The diet may also be administered to the animal or human for 24 hours following the exposure. Preferably, the diet may be administered to the animal or human for both 3-10 consecutive days prior to the animal or human is exposed to chemotherapy, radiotherapy, or oxidative stress and 24 hours following the exposure. For protection of an animal or human against aging, the diet may be administered every third meal or every 3-10 days.

In addition, the invention provides a method of protecting an animal or human against chemotherapy by fasting an animal or human suffering from cancer prior to or following chemotherapy. For example, an animal or human suffering from cancer may be fasted for 48-140 hours prior to one round of chemotherapy or 4-56 hours following the chemotherapy. Preferably, an animal or human suffering from cancer is fasted for 48-140 hours prior to one round of chemotherapy and 4-56 hours following the chemotherapy. When the animal or human is exposed to chemotherapy, normal cells, but not cancer cells, in the animal or human are protected. In some embodiments, the animal or human is fasted for no more than 180 hours prior to and following one round of chemotherapy.

It was observed in animals that fasting 48-60 hours pre-chemo+/−24 hours post chemo protects mice and sensitizes cancer cells against chemotherapy. Further, as shown below, in cancer patients, fasting or a very low calorie diet protected patients but not cancer cells against chemotherapy. The very low calorie/fasting diet also appeared to sensitize cancer cells to chemo. It was also observed in animal studies that fasting sensitized various cancers to several types of chemotherapy. In addition, in animal studies, fasting caused a 75% reduction in IGF-I and a 75-90% reduction in IGF-I was sufficient to protect animals but to sensitize cancer cells against chemotherapy. Moreover, human clinical trials showed that 5-day fasting and/or a low calorie/low protein/low sugar diet caused a 75% or higher reduction in IGF-I (Thissen et al. (1994) Endocrine Review 15 (1):80-101). Therefore, the very low calorie/low sugars but also very low protein diet will protect animals and human against chemotherapy and sensitize many types of cancer cells against chemotherapy.

The following examples are intended to illustrate, but not to limit, the scope of the invention. While such examples are typical of those that might be used, other procedures known to those skilled in the art may alternatively be utilized. Indeed, those of ordinary skill in the art can readily envision and produce further embodiments, based on the teachings herein, without undue experimentation.

EXAMPLE I

The strategies to treat cancer have focused largely on increasing the toxicity to tumor cells. The inventor has departed from the classic tumor-centric drug development focused on tumor killing and put focus on increasing the protection of normal cells. Recently, the inventor reported that a short-term starvation (STS; 40-60 hours) can enhance host resistance to chemotherapy while concomitantly enhancing tumor sensitivity to chemotherapy-induced apoptosis (Differential Stress Resistance, DSR) (1). The foundation of STS comes from the work of Dr. Longo in the aging field where growth-factor suppression and calorie restriction (CR) increase lifespan and stress resistance in various organisms. However, although a STS is a powerful method to differentially protect the host, it could have limited application in clinical settings. Therefore, the inventor investigated alternative pharmaceutical interventions that could also enhance host resistance against chemotherapy. During the search, the inventor determined 3 promising preparations that provided increased protection to the host against chemotherapy drugs. The pharmaceutical preparations that were effective in enhancing resistance against chemotherapy were 1) a methionine restricted amino acid mix (LAM1), 2) a tryptophan restricted amino acid mix (LTA1), and 3) glycerol (G1). LMA1 is effective only if the diet lacks other sources of methionine and LTA1 is effective only if the diet lacks other sources of tryptophan. Finally, G1 is effective in combination with a glucose-restricted diet. Interestingly, despite the fact that the diets were isocaloric and the food intake was similar, LMA1/LTA1 treated animals showed a lower weight profile. This suggests that LMA1/LTA1 allow the animals to shift the energy towards 'maintenance' rather than 'growth/reproduction', and therefore increases resistance against chemotherapy toxicity.

LMA1 Mix

Methionine restriction has been shown to increase lifespan and stress resistance in laboratory rodents (2, 3). Therefore, the effect of a low methionine amino acid mix (LMA1) in the absence of proteins in the diet in protection against chemotherapy toxicity in laboratory rodents was investigated. 5 days prior to chemotherapy, eight mice were given the LMA1 mix in combination with a protein-free diet (Harlan, TD. 07789). Methionine levels in the LMA1 mix were 20% of that of the control diet (TD. 07788). Following the 5-day LMA1 diet, mice were intravenously injected with a high-dose of doxorubicin (DXR, a widely used chemotherapy drug). To determine the degree of toxicity, mice were monitored daily for weight loss and abnormal behavior. Body weight and food intake was recorded daily. LMA1 treated mice recovered from the weight loss more quickly compared to the control group (FIG. 1). Furthermore, LMA1-treated mice showed significantly higher survival rate compared to the control mice following high-dose chemotherapy (63% vs. 13% respectively) (FIG. 1).

LTA1 Mix

Figure 2:
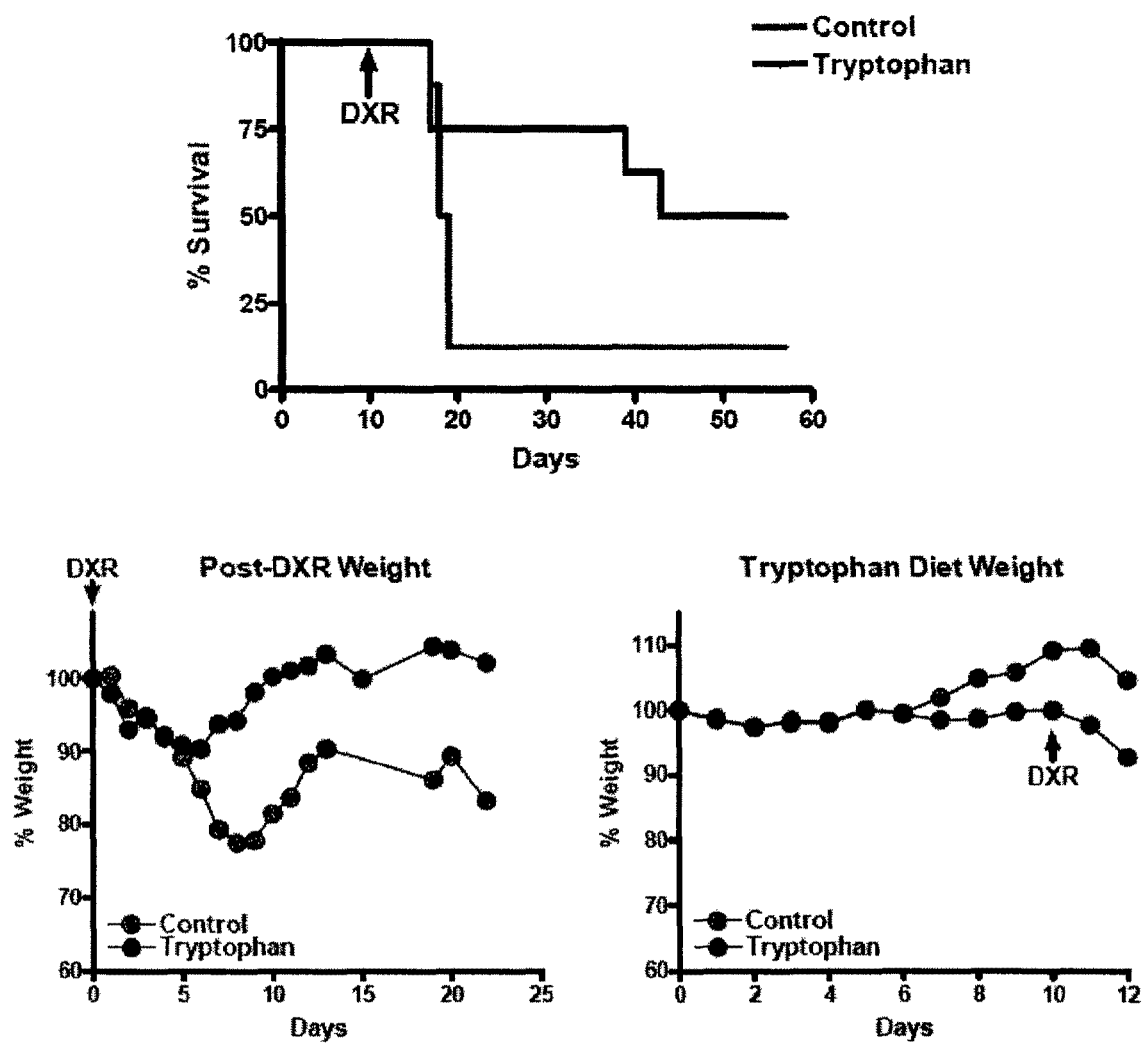
FIG. 2. Graph of (A) % survival, (B) post treatment body weight %, and (C) tryptophan diet body weight % as a function of days. Mice were treated with a low tryptophan amino acid mix (LTA1) before treatment with doxorubicin.

As with methionine restriction, a diet with low levels of tryptophan has also been shown to increase lifespan and decrease some age-related disease including cancer (4-7). Based on the fact that there is a strong correlation between longevity and stress resistance, the inventors believed that treatment of mice with a low tryptophan amino acid mix in the absence of other sources of tryptophan could also provide increased stress resistance in addition to lifespan extension. 10 days prior to chemotherapy, eight mice were treated with the LTA1 mix in combination with a diet lacking protein (Harlan, TD. 077 90). Tryptophan levels in the LTA1 mix was 20% of that of the control diet (TD. 07788). Toxicity was determined as done with the LMA1 mix experiments. The LTA1 mix improved weight management after chemotherapy, causing a quicker recovering of the weight loss compared to controls (FIG. 2). Also, mice treated with the LTA1 mix had a 4-fold higher survival rate compared to the controls (50% vs 12.5%) (FIG. 2).

G1 Mix

Figure 3:
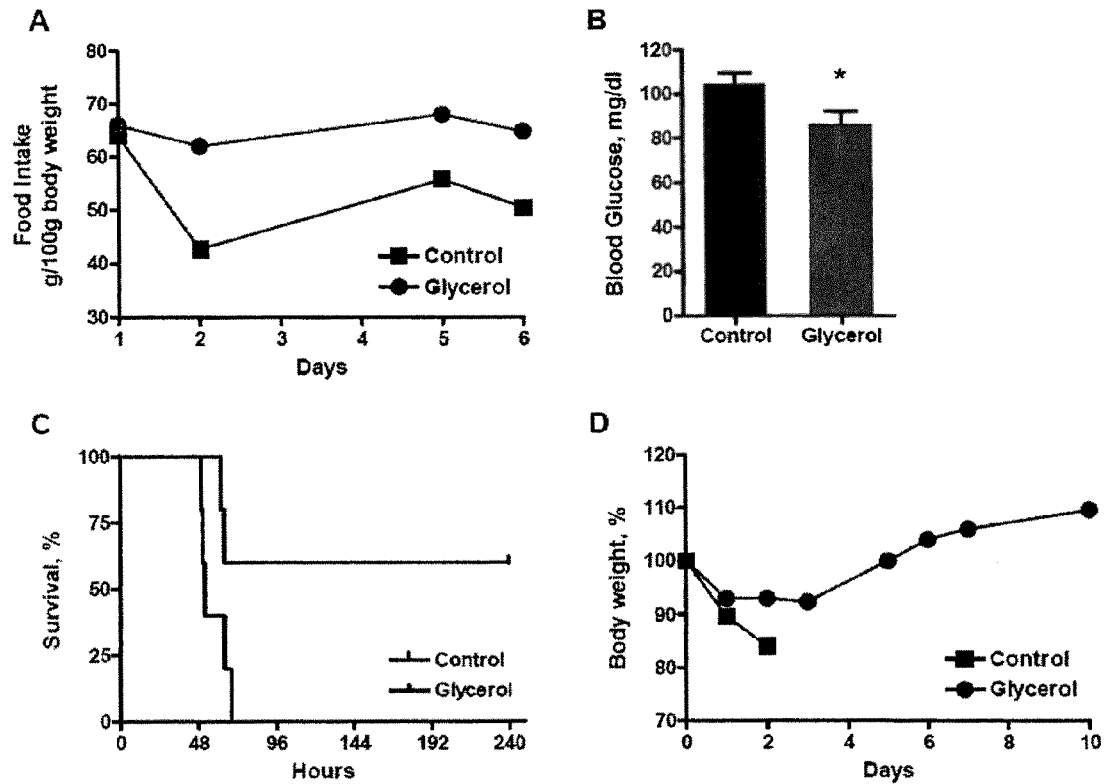
FIG. 3. Graph of (A) food intake as a function of days, (B) blood glucose levels, (C) % survival as a function of time, and (D) body weight % as a function of days. Mice were given a glycerol diet before treatment with paraquat.

Calorie restriction enhances stress resistance and extends life span in model organism ranging from yeast to mammals (Longo, 2003) (8, 9). In view of our recent results with starvation showing effects in the protection against multiple chemotherapy and the beneficial effects of carbon source substitution with glycerol in life span and stress resistance in yeast, the effect of feeding mice with glycerol on protection against toxins was studied. Two groups of five mice each were fed ad libitum for six days with two isocaloric diets, the control diet (Teklad 8604 chow supplemented with 40% starch/sucrose/maltose dextrin) or the G1 diet containing glycerol (supplemented with 40% glycerol). Although the mice on the glycerol diet ate slightly more than those on the control diet, they showed an 18% reduction in blood glucose level by day 6 (FIG. 3). Both groups of mice were then given a single dose of 50 mg/kg paraquat intraperitoneally and put back on a normal diet (8604 chow). Paraquat is known to cause S-phase arrest of liver and lung cells (10) and lead to death (11). All mice in the control group were dead by day 3, whereas three out of five glycerol-fed mice fully protected from the paraquat toxicity (FIG. 3C, p<0.05) and regained normal body weight five days after paraquat treatment (FIG. 3D). These results indicate that dietary carbon source substitution with glycerol enhances oxidative stress resistance in vivo and has the potential to mimic calorie restriction in higher eukaryotes.

Materials and Methods

LMA1 and LTA1

LMA1 and LTA1 are based on purified synthetic amino acid mixes (1) and were custom manufactured for us by Harlan Tekald in a ½" pellet form. All groups including Control (TD. 07788), LMA1 (TD. 07790), and LTA1 (TD. 07789) received isocaloric diets (3.9 Kcal/g).

LMA1 mix: CD-1 mice, weighing 25-30 g, were prefed for 5 days prior to chemotherapy with purified synthetic amino acids mixes containing either normal (0.86%) or low (0.17%) levels of methionine.

LTA1 mix: CD-1 mice, weighing 25-30 g, were prefed for 5 days prior to chemotherapy with purified synthetic amino acids mixes containing either normal (0.86%) or low (0.17%) levels of tryptophan.

TABLE I

Composition of control diet

| Formula | g/Kg |
| --- | --- |
| L-Alanine | 3.5 |
| L-Arginine HCl | 12.1 |
| L-Asparagine | 6.0 |
| L-Aspartic Acid | 3.5 |
| L-Cystine | 3.5 |
| L-Glutamic Acid | 40.0 |
| Glycine | 23.3 |
| L-Histidine HCl, monohydrate | 4.5 |
| L-Isoleucine | 8.2 |
| L-Leucine | 11.1 |
| L-Lysine HCl | 18.0 |
| L-Methionine | 8.6 |
| L-Phenylalanine | 7.5 |
| L-Proline | 3.5 |
| L-Serine | 3.5 |
| L-Threonine | 8.2 |
| L-Tryptophan | 1.8 |
| L-Tyrosine | 5.0 |
| Sucrose | 344.53 |
| Corn Starch | 150.0 |
| Maltodextrin | 150.0 |
| Soybean Oil | 80.0 |
| Cellulose | 30.0 |
| Mineral Mix, AIN-93M-MX (94049) | 35.0 |
| Calcium Phosphate, monobasic, monohydrate | 8.2 |
| Vitamin Mix, AIN-93-VX (94047) | 19.5 |
| Choline Bitartrate | 2.75 |
| TBHQ, antioxidant | 0.02 |

Doxorubicin Studies in Mice

Following treatments with LMA1 or LTA1, mice were intravenously injected with 24-26 mg/kg doxorubicin (Bedford Laboratories) with 30 gauge insulin syringes (Becton, Dickinson and Company). Doxorubicin was dissolved in purified water and diluted in saline to a final concentration of 5 mg/ml. All doxorubicin injections were followed by a saline/heparin wash to minimize endothelial cell damage. To determine toxicity and efficacy, mice were monitored routinely for weight loss and general behavior. Body weight was recorded once daily throughout the experiment. Mice found moribund were sacrificed by $CO_2$ narcosis and necropsy was performed. Since cardiotoxicity is the major cause of death from acute doxorubicin toxicity, we prepared histological slides to examine the degree of damage at the tissue level.

Glycerol Diet in Mice

A/J mice, weighing 18-24 g, were given a 40% glycerol diet (w/w) for 6 days. The diet composed of 60% pellet (Harlan Teklad, Diet 8604) and 40% glycerol (Bio-Serv, NJ)

by weight. Briefly, pellets were finely ground using a food processor and mixed with USP grade glycerol. The density of glycerol (1.26 g/ml) was taken into account when mixing with pellet powder. Food was dried for 4 days. Since glycerol is hygroscopic, it absorbed atmospheric moisture and increased the pellet weight 3% during the first 3 days of the drying process and maintained stable weight thereafter. Blood glucose levels were measured on day 6. The tail vein was minimally punctured using a sterile 31 gauge needle and briefly bled. Blood glucose levels were determined with a Precision Xtra blood glucose monitoring system (Abbott Laboratories). Since glycerol is metabolized primarily in the liver and kidneys, these organs were collected at the time of necropsy for histological examination.

Paraquat Studies in Mice

Following the 6 days of glycerol diet, mice were injected with paraquat (Sigma). Paraquat was prepared in phosphate buffered saline (PBS) at 7.5 mg/ml and injected at 50 mg/kg intraperitoneally using a 31 gauge syringe (Becton, Dickinson and Co). Immediately following paraquat administration, animals were returned to the normal diet (Harlan Teklad, Diet 8604). Mice were monitored every 2 hours for 4 days and body weight was recorded once daily throughout the experiment. Body weight measures were divided into 2 phases—glycerol diet phase and post-paraquat phase—and analyzed. Mice were sacrificed when they showed signs of stress or pain and also determined to have no chance of recovery by highly trained and experienced researchers. Since the lung is the major target organ, sacrificed mice were necropsied and the lung was collected for histological examination. Briefly, the lung slices were fixed in 4% formaldehyde, paraffin embedded and sectioned to 4 μm thickness, and H&E stained.

REFERENCES

1. Raffaghello L, Lee C, Safdie F M, Wei M, Madia F, Bianchi G, & Longo V D (2008) Proc Natl Acad Sci USA.
2. Miller R A, Buehner G, Chang Y, Harper J M, Sigler R, & Smith-Wheelock M (2005) Aging Cell 4, 119-125.
3. Orentreich N, Matias J R, DeFelice A, & Zimmerman J A (1993) J Nutr 123, 269-274.
4. Ooka H, Segall P E, & Timiras P S (1988) Mech Ageing Dev 43, 79-98.
5. Segall P E & Timiras P S (1976) Mech Ageing Dev 5, 109-124.
6. Timiras P S, Hudson D B, & Segall P E (1984) Neurobiol Aging 5, 235-242.
7. Anisimov V N (2001) Exp Gerontol 36, 1101-1136.
8. Masoro E J (2005) Mech Ageing Dev 126, 913-922.
9. Kennedy B K, Steffen K K, & Kaeberlein M (2007) Cell Mol Life Sci 64, 1323-1328.
10. Matsubara M, Yamagami K, Kitazawa Y, Kawamoto K, & Tanaka T (1996) Arch Toxicol 70, 514-518.
11. Migliaccio E, Giorgio M, Mele S, Pelicci G, Reboldi P, Pandolfi P P, Lanfrancone L, & Pelicci P G (1999) Nature 402, 309-313.
12. Rogers Q R & Harper A E (1965) J Nutr 87, 267-273.

EXAMPLE II

SCH9-Regulated Carbon Source Substitution is as Effective as Calorie Restriction in Life Span Extension Summary The effect of calorie restriction (CR) on life span extension, demonstrated in organisms ranging from yeast to mice, may involve the down-regulation of pathways including Tor, Akt, and Ras. Here we present genetic and gene expression data suggesting that yeast Sch9 (a homolog of both mammalian kinases Akt and S6K) is a central component of a network that controls a common set of genes implicated in a metabolic switch from the TCA cycle and respiration to glycolysis and glycerol biosynthesis. During chronological survival, mutants lacking SCH9 depleted extracellular ethanol, reduced stored lipids but synthesized and released glycerol. Deletion of the glycerol biosynthesis genes GPD1, GPD2 or RHR2, among the most up-regulated in long-lived sch9Δ, tor1Δ, and ras2Δ mutants, was sufficient to reverse chronological life span extension and stress resistance in sch9Δ mutants. Replacement of glucose or ethanol with glycerol as carbon source caused a longevity extension comparable to that caused by calorie restriction or starvation. Replacement of glucose-based carbohydrates with glycerol in the mouse diet reduced glucose level and enhanced resistance to oxidative stress. These results suggest that "carbon source substitution" (CSS) represents a new strategy to delay aging and protect cells against damage.

Introduction

Mutations that decrease the activities of the Akt/PKB, Tor, and Ras pathways extend the lifespan of several model organisms, suggesting that the underlying mechanisms of longevity regulation are conserved in many eukaryotic organisms (Kenyon, 2001; Longo and Finch, 2003). Akt/PKB is a highly conserved serine-threonine kinase shown to function in the Daf-2 longevity pathway of *Caenorhabditis elegans* (Paradis et al., 1999). Homologous longevity modulating pathways were also identified in *Drosophila* and mice (Kenyon, 2001). In yeast, Sch9, which shares high sequence identity with the mammalian kinases Akt/PYB and S6K, is part of a nutrient-sensing pathway whose downregulation extends the chronological lifespan (CLS, the survival time of population of non-dividing yeast) by up to 3-fold (Fabrizio et al., 2001). The Ras G-proteins are also evolutionary conserved and implicated in cell division in response to glucose/growth factors. The deletion of RAS2 doubles the CLS of yeast (Fabrizio et al., 2003). In mammals, a role for Ras in longevity control has not been established conclusively but, together with Akt, Ras is one of the major mediators of IGF-I signaling, which has been shown to promote aging (Holzenberger, 2004; Longo, 2004). Another conserved nutrient-responsive pathway, regulating cell growth and cell-cycle progression, involves the protein kinase target of rapamycin, TOR, which has been associated with life span regulation in *C. elegans* and *Drosophila*. Knockdown of LET-363/CeTOR, starting at the first day of the adult life, more than doubled the life span of worm (Vellai et al., 2003). Similarly, a reduced activity of Daf-15, the worm ortholog of the mammalian mTOR-interacting protein raptor, promotes life span extension (Jia et al., 2004). In flies, overexpression of dominant-negative dTOR or TOR-inhibitory dTsc1/2 proteins also leads to longevity extension (Kapahi et al., 2004). Moreover, knockdown of CeTOR does not further extend the life span of worms subject to dietary restriction (DR) and inhibition of TOR protects flies from the deleterious effects of rich food, suggesting the beneficial effect of DR is, at least in part, mediated by TOR (Hansen et al., 2007; Kapahi et al., 2004).

Two TOR orthologs, TOR1 and TOR2, have been identified in yeast. Both Tor1 and Tor2 mediate growth-related signaling in a rapamycin-sensitive manner, whereas Tor2 has an additional rapamycin-insensitive function in controlling the cell-cycle-dependent organization of actin cytoskeleton (Loewith et al., 2002). Reduction of the TOR pathway activity results in an extension of yeast replicative life span (RLS), the number of daughter cells generated by individual mother cells (Kennedy et al., 1994; Mortimer and Johnston, 1959), comparable to that obtained when Sch9 is inactivated (Kaeberlein et al., 2005a; Kaeberlein and Kennedy, 2005). Furthermore, a high throughput assay to measure the CLS of individual yeast deletion mutants identified several long-lived strains carrying deletions of genes implicated in the Tor pathway (Powers et al., 2006). Additional evidence supporting an inverse correlation between Tor1 activity and CLS has recently been provided (Bonawitz et al., 2007).

The aging-regulatory function of both yeast Tor1 and Sch9 mediates the calorie restriction (CR)-dependent RLS extension. The down-regulation of either pathway mimics the effect of lowering the glucose content of the medium, and no further extension of RLS is observed when the sch9Δ or the tor1Δ mutants are calorie restricted (Kaeberlein et al., 2005b). Ethanol produced during fermentative growth is used as carbon source during diauxic shift and post-diauxic phase, when the yeast cells switch from rapid growth to slow budding and eventually ceasing proliferation (Gray et al., 2004; Lillie and Pringle, 1980). Switching yeast grown in glucose/ethanol medium to water models an extreme CR/starvation condition for non-dividing cells. This severe form of CR doubles chronological survival of wild type yeast (Fabrizio and Longo, 2003). In contrast to RLS, CR-induced increase of CLS is only partially mediated by Sch9 (Fabrizio et al., 2005; Wei et al., 2008).

Despite the extensive body of work demonstrating a link between nutrient-sensing pathways and life span regulation in different organisms, the key mechanisms responsible for delaying the aging process are still elusive. The direct correlation between life span extension and the ability to withstand different stress challenges, which has been observed in different model organisms, indicates that the activation of cellular protection represents an important survival strategy (Longo and Fabrizio, 2002). Our previous studies suggest that superoxide plays an important role in aging and age-dependent mortality, but protection against superoxide only accounts for a small portion of the potent effect of mutations in SCH9 and RAS2 on life span (Fabrizio et al., 2003). The connection between calorie restriction and the Sch9, Tor, and Ras2 pathways as well as the mechanisms of CR-dependent effects on life span are poorly understood. Here we present evidence that changes in the expression of a set of genes controlled by Sch9 but also Tor and Ras lead to a metabolic switch to glycerol production, which causes enhanced cellular protection and life span extension. Replacement of glucose or ethanol with glycerol as carbon source is as effective as calorie restriction in promoting cellular protection and life span extension. Dietary substitution of sugars with glycerol also protected mice against oxidative stress, suggesting that carbon source substitution (CSS) has the potential to trigger some of the protective effects of calorie restriction or starvation in higher eukaryotes.

Results

Genetic Interactions Between SCH9, and RAS2 and TOR1

Figure 4:
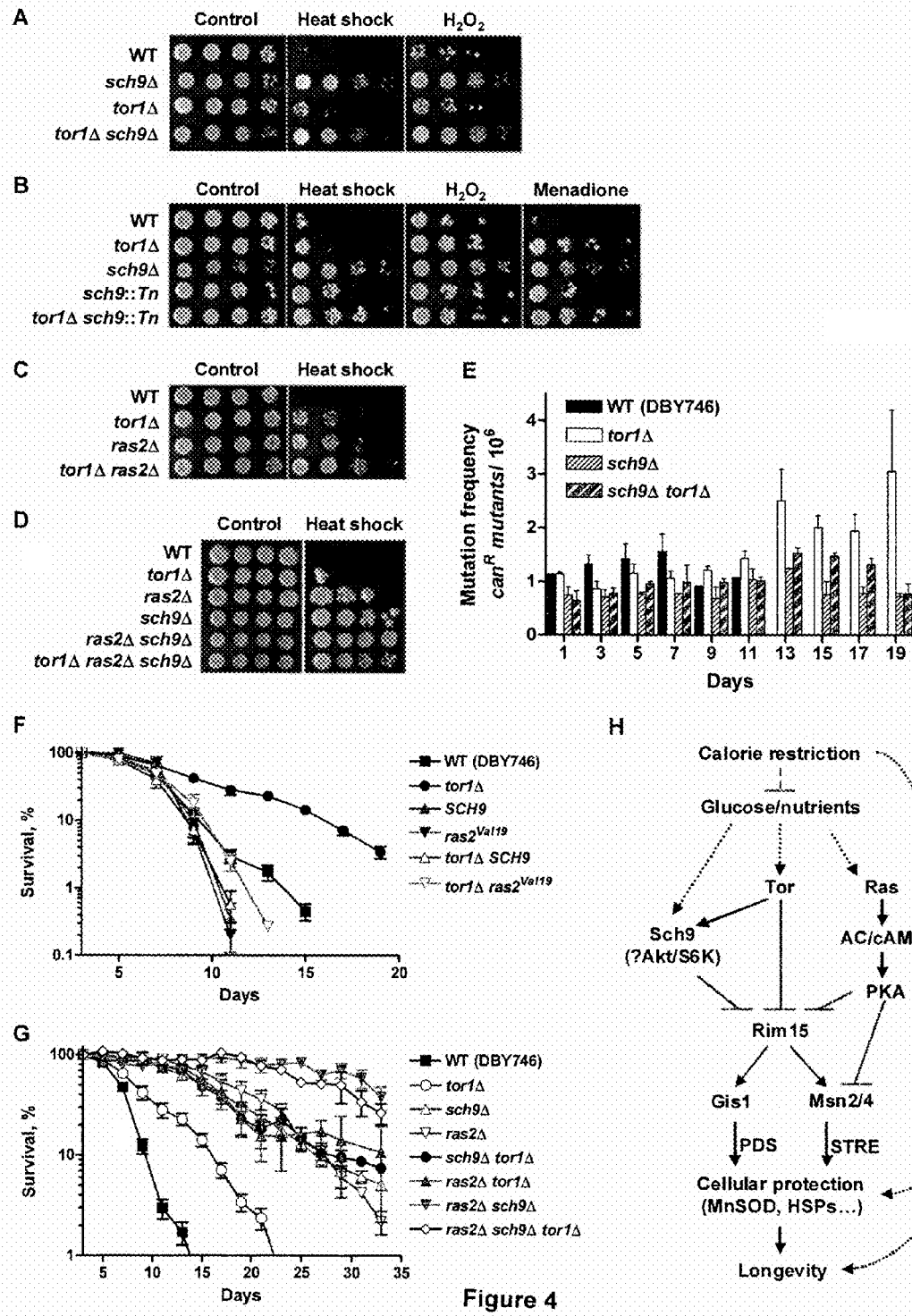
FIG. 4. Genetic interactions between Sch9, Tor1, and Ras2 in regulating stress resistance and life span. (A-D) Day 3 wild type (DBY746) and cells lacking Tor1, Sch9, or Ras2 were challenged with heat shock (55° C.: A, 105 min; B, 75 min; C, 150 min; and D, 120 min) or oxidative stresses ($H_2O_2$, 100 mM for 60 min; or menadione, 250 µM for 30 min). (E) Mutation frequency over time measured as $can^R$ mutants per million cells. The average of four experiments is shown. Error bars represent SEM. (F) Chronological survival in minimal complete medium (SDC) of wild type (DBY746), tor1Δ, and mutants overexpressing either SCH9 or constitutively active Ras2 ($ras2^{Val19}$). (G) Chronological survival of wild type (DBY746) and mutants lacking Tor1, Sch9, Ras2 or combinations shown in the graph. The data represent average of at least 4 experiments. Error bars show SEM. For mean life span calculated from non-linear curve fitting see Table 2. (H) Longevity regulatory pathways in yeast. The nutrient sensing pathways controlled by Sch9, Tor, and Ras converge on the protein kinase Rim15. In turn, the stress response transcription factors Msn2, Msn4, and Gis1 transactivate stress response genes and enhance cellular protection, which lead to life span extension. Pro-longevity effects of CR are partially mediated by Sch9, Tor, and Ras, and may also require additional yet-to-be identified mechanism(s).
Figure 5:
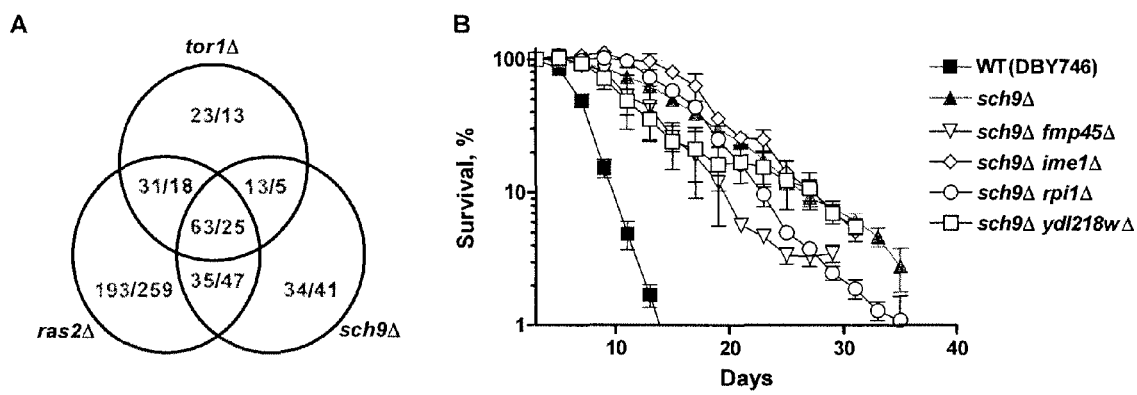
FIG. 5. Gene-expression profiles of long-lived mutants. (A) Venn diagram of the number of genes up- or down-regulated more than 2-fold in the tor1Δ, sch9Δ, and ras2Δ mutants, at day 2.5, compared to wild type cells. Microarray analyses were carried out in triplicates. Data represent up/down-regulated genes. (B) Life span of mutants with deletions of genes most upregulated in long-lived mutants in the sch9Δ background. Three to four independent experiments for each strain were performed. Data represent mean and SEM of pair matched pooled experiments.

Using a genetic approach, we examined the relationship between Sch9, Tor1, and Ras2 in regulating cellular protection against stress and life span. The effects on life span and stress resistance caused by deficiency in Tor1 activity are less robust than those observed in the strains lacking Sch9 or Ras2. We did not observe any significant difference in mean lifespan or stress resistance between sch9Δ and the tor1Δ sch9Δ double knockout strains (FIGS. 4A and 4G). By contrast, the deletion of TOR1 in a mutant carrying a transposon insertion in the promoter region of SCH9, which only reduces SCH9 expression (Fabrizio et al., 2001), caused a further increase of resistance to heat and to the superoxide-generating agent menadione, but not to $H_2O_2$ (FIG. 4B), suggesting that the lack of TOR1 contributes to the further inactivation of the Sch9 pathway. This result is in agreement with the recent study showing that Sch9 is a direct target of rapamycin-sensitive Tor complex I (TORC1) (Urban et al., 2007) In fact, reducing the TORC1 activity either by deleting TCO89, which encodes a TORC1 component, or by rapamycin treatment increased cell resistance to heat and $H_2O_2$. Since Sch9 activity is associated with an age-dependent increase of mutation frequency (Fabrizio et al., 2005), we examined the interaction between Sch9 and Tor1 in the regulation of genomic instability during chronological aging. Whereas the tor1Δ mutant was slightly less susceptible than wild type cells to genomic instability (measured as age-dependent frequency of mutations of the CAN1 gene) between day 1 and 7, there was no significant change in the mutation frequency of the double tor1Δ sch9Δ mutant compared to that of the sch9Δ mutant (FIG. 4E). Overexpression of TOR1 only slightly reduced the stress resistance phenotype of sch9Δ. However, resistance to stress and life span extension of tor1Δ was abolished by overexpressing SCH9 (FIG. 5F). Taken together, these data are in agreement with a shared signaling pathway between Tor and Sch9 in life span regulation and suggest an upstream role of Tor1 in Sch9 signaling (FIG. 4H).

Both Tor and Ras/cAMP-PKA signalings are known to regulate stress-responsive (STRE) genes (Zurita-Martinez and Cardenas, 2005). Elevating Ras activity by ectopically expressing constitutively active Ras2 ($ras2^{Val19}$) reversed the life span extension and the stress resistance of tor1Δ mutants (FIG. 4F). Conversely, deletion of RAS2 has an additive effect to tor1Δ with respect to stress resistance but not life span (FIGS. 4C and 4G), suggesting an overlapping in longevity modulation by Tor1 and Ras2.

We have previously shown that longevity regulations controlled by Tor1, Sch9, and Ras2 converge on the protein kinase Rim15 (Wei et al., 2008). Rim15 positively regulates stress response transcription factors (TFs) Msn2/4 and Gis1, which activate genes involved in cellular protection. Interestingly, enhancement of stress resistance and life span extension associated with Ras2 deficiency requires both the STRE-binding TFs Msn2/4 and PDS-binding Gis1, whereas the sch9Δ-mediated longevity regulation mainly depends on the latter (Fabrizio et al., 2001; Wei et al., 2008). These results indicate that the common downstream effectors are differentially modulated by the Sch9 and Ras2. In fact, the ras2Δ sch9Δ double knockout cells exhibited higher stress resistance than either of the single deletion mutants (FIG. 4D). It also showed a 5-fold increase in mean life span compared to wild type cells (FIG. 5G). The triple sch9Δ ras2Δ tor1Δ deletion mutant, however, did not show any further increase of life span or stress resistance (FIGS. 4D and 4G). These results depict a life-span regulatory network composed of parallel but partially connected signaling pathways controlled by Tor/Sch9 and Ras (FIG. 4H).

Gene Expression Profiles of Long-Lived Mutants

To identify the mediators of life span extension downstream of the Tor/Sch9 and Ras pathways, we carried out DNA microarray analyses for all three major long-lived mutants: sch9Δ, tor1Δ, and ras2Δ. Total RNA was extracted from 2.5 day-old cultures of long-lived mutants and wild type cells. This age was selected to avoid both the noise that may arise from a small fraction of cells that are still dividing at younger ages (day 1-2) and the general decrease in metabolism and consequently in gene expression that normally occurs at older ages (day 4-5) (Fabrizio and Longo, 2003). The cRNA obtained from total RNA was hybridized to gene chips that allow the detection of 5841 of the 5845 genes present in *S. cerevisiae*. Three independent populations of each genotype were analyzed. A total of 800 genes showed a greater than 2-fold change in expression relative to wild type cells. Among these, 63 genes were consistently up-regulated more than 2-fold in all three mutants, and 25 genes were consistently down-regulated (FIG. 5A). The mRNA levels of seven of the most up-regulated and one most down-regulated Although the data point to common changes in all 3 long-lived mutants, the GO category analysis indicated a divergence in expression pattern between ras2Δ and the other two mutants, which is in agreement with our genetic analysis of two parallel signaling pathways controlled by Sch9 and Ras2, and is consistent with the role of Sch9 and Tor in the same life span regulatory pathway (Table 1 and FIG. 4H) (Wei, 2008).

TABLE 1

Gene ontology (GO) analysis of expression profiles of long-lived mutants

| GO* | GO ID | Gene # | Annotation | sch9Δ p | sch9Δ q | tor1Δ p | tor1Δ q | ras2Δ p | ras2Δ q |
|---|---|---|---|---|---|---|---|---|---|
| | | | Positively affected TIGO categories | | | | | | |
| C | GO: 0005842 | 93 | cytosolic large ribosomal subunit | 0.00E+00 | 0.00E+00 | 0.00E+00 | 0.00E+00 | 1.64E−12 | 2.37E−10 |
| C | GO: 0005843 | 63 | cytosolic small ribosomal subunit | 0.00E+00 | 0.00E+00 | 0.00E+00 | 0.00E+00 | 7.49E−09 | 6.49E−07 |
| P | GO: 0016125 | 37 | sterol metabolism | 5.65E−03 | 6.20E−02 | 7.50E−03 | 7.56E−02 | 7.51E−05 | 2.32E−03 |
| P | GO: 0046365 | 33 | monosaccharide catabolism | 1.32E−03 | 2.01E−02 | 2.94E−05 | 1.02E−03 | 8.81E−06 | 3.81E−04 |
| | | | Negatively affected TIGO categories | | | | | | |
| C | GO: 0005762 | 43 | mitochondrial large ribosomal subunit | 1.56E−19 | 3.32E−17 | 1.13E−20 | 4.29E−18 | 1.34E−20 | 4.29E−18 |
| C | GO: 0005763 | 34 | mitochondrial small ribosomal subunit | 6.94E−13 | 4.93E−11 | 3.17E−13 | 2.54E−11 | 4.83E−14 | 4.41E−12 |
| C | GO: 0016591 | 74 | DNA-directed RNA polymerase II, holoenzyme | 1.61E−05 | 2.29E−04 | 9.05E−05 | 8.65E−04 | 4.97E−10 | 2.27E−08 |
| C | GO: 0000502 | 46 | proteasome complex | 3.92E−04 | 2.56E−03 | 4.51E−03 | 1.72E−02 | 1.35E−08 | 4.79E−07 |
| C | GO: 0005743 | 158 | mitochondrial inner membrane | 2.64E−16 | 2.82E−14 | 3.56E−17 | 5.70E−15 | 3.14E−09 | 1.34E−07 |
| F | GO: 0008080 | 37 | N-acetyltransferase activity | 6.89E−03 | 2.32E−02 | 6.43E−03 | 2.25E−02 | 3.16E−04 | 2.20E−03 |
| P | GO: 0016570 | 59 | histone modification | 1.56E−03 | 7.85E−03 | 2.16E−04 | 1.64E−03 | 7.30E−06 | 1.14E−04 |
| P | GO: 0006365 | 67 | 35S primary transcript processing | 1.93E−03 | 9.16E−03 | 3.84E−06 | 7.23E−05 | 4.05E−03 | 1.59E−02 |
| P | GO: 0007005 | 95 | mitochondrion organization and biogenesis | 6.62E−05 | 7.02E−04 | 1.32E−04 | 1.07E−03 | 4.51E−06 | 8.02E−05 |
| P | GO: 0016044 | 31 | membrane organization and biogenesis | 2.09E−03 | 9.85E−03 | 1.38E−03 | 7.18E−03 | 9.74E−03 | 3.06E−02 |
| P | GO: 0006626 | 47 | protein-mitochondrial targeting | 8.33E−06 | 1.27E−04 | 1.46E−06 | 3.11E−05 | 4.04E−04 | 2.59E−03 |
| P | GO: 0009060 | 82 | aerobic respiration | 2.66E−08 | 8.96E−07 | 4.73E−09 | 1.78E−07 | 1.32E−06 | 3.01E−05 |
| P | GO: 0006119 | 46 | oxidative phosphorylation | 7.03E−07 | 2.04E−05 | 9.01E−07 | 2.31E−05 | 1.57E−04 | 1.24E−03 |
| P | GO: 0006118 | 31 | electron transport | 1.22E−04 | 1.03E−03 | 1.01E−04 | 9.28E−04 | 4.29E−03 | 1.65E−02 |

*C, Cellular component; F, molecular function; and P, biological process genes in both the tor1Δ and sch9Δ mutants were confirmed by quantitative RT-PCR and/or Northern blot. Based on the pair-wise comparison of the long-lived mutants, the up- and down-regulation of genes in these long-lived mutants are significantly overlapping, suggesting that the Ras, Tor, and Sch9-centered longevity regulatory network controls a common set of down-stream genes (Table 1). To identify features common to the three long-lived mutants we performed a gene ontology (GO) analysis of the microarray data by Wilcoxon rank test.

Gene ontology (GO) analysis of expression profiles of long-lived mutants. Significantly up- or down-regulated categories were shown (p<0.01). q-value was also calculated to correct the multi-testing error.

Metabolic Changes Associated with Longevity-Extension

Gene expression profile comparison between long-lived mutants and wild type cells reveals a consistent down-regulation of the genes encoding mitochondrial proteins, including those that function in the TCA cycle, oxidative phosphorylation, mitochondrial ribosomal proteins, as well as proteins targeted to mitochondria. The expression of glycolytic/fermentative genes, but not of gluconeogenic genes, was instead up-regulated. Interestingly, several genes coding for high-affinity glucose transporters or putative glucose transporters, known to be inhibited by high glucose concentrations (Ozcan and Johnston, 1999), were up-regulated indicating that the long-lived mutants may have entered a starvation-like mode in which glucose uptake is maximized. Considering that the extracellular glucose was exhausted in mutants as well as wild type cells by day 1-2, the major substrate available for fermentation by day 2.5 is probably glycogen, which is normally accumulated by yeast in the late phases of exponential growth (Werner-Washburne et al., 1993).

Genes involved in stationary phase survival, sporulation, meiosis, and stress response (FMP45, GRE1, IME1, RPI1, SPS100, and TAH1) were among the most upregulated genes in all three long-lived mutants. To test their contribution to life span extension and stress resistance in long-lived mutants, we originated a set of double mutants carrying the deletion of SCH9, RAS2 or TOR1 in combination with that of one of the most up-regulated genes. Whereas the deletion of either FMP45 or YDL218W slightly reduced the mean life span of the sch9Δ mutants (FIG. 5B), they have no effect on ras2Δ mutants. The deletion of IME1 or RPI1 did not affect either the stress resistance or the life span extension caused by the lack of Sch9 (FIG. 5B). Deletion of YLR012C, the most down-regulated gene, did not affect significantly the life span or the stress resistance of the cell.

Several genes coding for proteins that function in the ergosterol biosynthesis were up-regulated in the long-lived mutants. Ergosterol is the predominant sterol in yeast and is structurally closely related to cholesterol. Besides being a structural component of the cellular membrane, ergosterol affects phospholipid synthesis, lipid rafts formation, signal transduction, as well as aerobic energy metabolism (Parks et al., 1995). The deletion of either HMG1 or ERG28 caused a significant decrease in both heat and oxidative stress resistance in the sch9Δ mutants. However, the deletion of ERG5, the most up-regulated ergosterol biosynthesis gene in our microarray analysis, did not reverse longevity extension or reduced stress resistance associated with the sch9Δ mutants. Notably, the ergosterol biosynthetic genes that were upregulated in all three long-lived mutants are those involved in converting squalene to ergosterol, which require molecular oxygen and often involve oxidation of NADPH to $NADP^+$. The upregulation may reflect a hypoxic environment during the post-diauxic phase survival of these long-lived mutants and suggests a link between redox state of the cell and survival. Taken together, these results indicate that the deletion of many single genes among the most up-regulated in long-lived mutants has little effect on life span.

Increased Expression of Glycerol Biosynthetic Genes in Long-Lived Mutants

Figure 6:
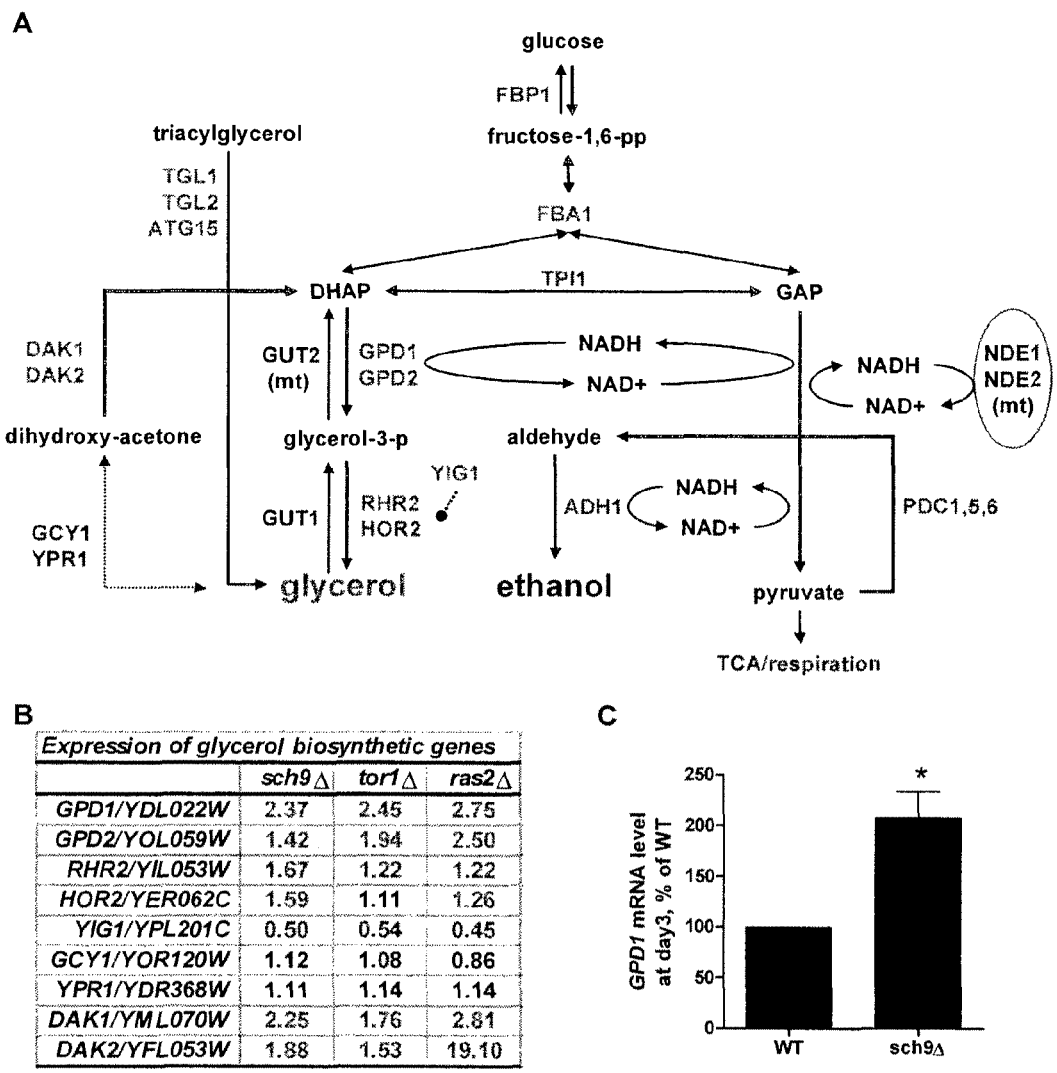
FIG. 6. (A) Schematic representation of glycerol metabolism. For illustration purpose, genes upregulated more than 20% compared to wild type in all three long-lived mutants are labeled in red; those down-regulated in green. (B) Fold change in expression levels of glycerol biosynthetic genes in sch9Δ, tor1Δ, and ras2Δ mutants compared to wild type (DBY746) at day 2.5. (C) Real time quantitative PCR analysis of GPD1 mRNA level in wild type (DBY746) and sch9Δ cells at day 3. Data represent mean and SEM, n=4. * p<0.05, t-test, two-tailed, sch9Δ vs. WT.

In addition to the lower expression of TCA cycle and respiratory genes and higher expression of glycolytic/fermentative genes, we also observed an up-regulation of the genes implicated in the metabolism of glycerol, a byproduct of the overflow metabolism when there is enhanced glycolytic flux and limited respiration capacity (FIGS. 6A and 6B). Significant up-regulation of genes involved in glycerol metabolism (21 genes) was observed in sch9Δ and ras2Δ mutants (p-value of 0.0058 and 0.0142, Wilcoxon rank test, one-sided, respectively). In yeast, glycerol is produced from either triacylglycerol or dihydroxy-acetone-phosphate (DHAP), a glycolysis intermediate (FIG. 6A). Whereas the genes encoding the lipases responsible for the hydrolysis of triacylglycerol were slightly up-regulated, GPD1 and GPD2, encoding the key enzymes required for glycerol production from DHAP, showed higher levels of expression in all the long-lived mutants (FIGS. 6B and 6C), suggesting that part of the glucose utilized by these mutants is redirected towards glycerol biosynthesis.

In fact, high level of intracellular glycerol was observed in the sch9Δ mutants compared to that in wild type cells at day 3 (FIG. 7A). In wild type cells the level of extracellular glycerol reached a peak at day 2 but was mostly depleted by day 3. In the sch9Δ culture, however, a much elevated level of glycerol was measured in the medium up to day 9 (FIG. 7B). By contrast, ethanol produced during the exponential growth, and most likely in the post-diauxic phase as well, was depleted early in sch9Δ mutants but not in wild type cells (FIGS. 7C and 7D) (Fabrizio et al., 2005), suggesting a metabolic switch from biosynthesis and release of ethanol in wild type cells to that of glycerol in sch9Δ mutants. Glycerol accumulation could be accompanied by the depletion of other carbon sources as well. Nile red staining of the lipid body indicated that the levels of triacylglycerol and other neutral lipids in sch9Δ mutants were consistently lower compared to that in wild type cells across all ages (FIG. 7E), which is in agreement with a modest but consistent increase of mRNA levels of lipolytic enzymes converting lipids to glycerol. Accumulation of extracellular glycerol also occurred for tor1Δ and ras2Δ mutants, but was lower than that observed for sch9Δ mutants.

Glycerol Biosynthesis Genes are Required for Life Span Extension in Sch9Δ

To further examine the role of glycerol biosynthesis in life span regulation, we generated stains lacking Rhr2, the yeast DL-glycerol-3-phosphatase, in the sch9Δ background. The rhr2Δ sch9Δ double mutant failed to accumulate glycerol extracellularly (FIG. 8A). Deletion of RHR2 abolished the life span extension as well as the resistance to heat and oxidative stresses associated with the lack of SCH9 in the DBY746 genetic background (FIGS. 8B and 8C). Utilizing the yeast KO collection (BY4741 genetic background), we deleted SCH9 in strains lacking key glycerol biosynthetic genes. Deficiency in either of the NAD-dependent glycerol 3-phosphate dehydrogenase genes, GPD1 or GPD2, did not cause a significant life span change in wild type BY4741 cells. However, the deletion of either GPD1 or GPD2, led to the reversion of the longevity extension associated with Sch9 deficiency (FIG. 5D). Similarly, the deletion of RHR2 abolished the life span extension in the sch9Δ mutant (FIG. 5D). By contrast, lack of Hor2, a redundant isoenzyme of DL-glycerol-3-phosphatase, did not affect the life span of the sch9Δ mutant. The difference between these two isoenzymes may be explained by the fact that Rhr2 is the predominant isoenzyme in the cell (Norbeck et al., 1996). In agreement with the major role of Rhr2, the mRNA level of YIG1, coding for an inhibitor of Rhr2 (Granath et al., 2005), was down-regulated in all long-lived mutants (FIG. 6B). Notably, the life span of rhr2Δ mutants in the BY4741 genetic background was similar to that of wild type cells although some rhr2Δ cultures showed regrowth/gasping (Fabrizio et al., 2004).

Cells lacking both Rhr2 and Hor2 have been shown to be hypersensitive to the superoxide anion generator, paraquat, suggesting a role for glycerol biosynthesis in cellular protection beyond osmotic stress (Pahlman et al., 2001). We tested the role of glycerol biosynthetic genes in the stress resistance of sch9Δ mutants. Hypersensitivity to heat and peroxide-induced oxidative stress was observed in the RHR2-null strain, but not in gpd1Δ, gpd2Δ, or hor2Δ mutants in the BY4741 background (FIG. 8E). Furthermore, cells lack Yig1, the Rhr2 inhibitor, were slightly more resistant to stress compared to wild type cells (FIG. 8E). The stress resistance phenotype of sch9Δ mutants was partially reversed by deletion of GPD1, GPD2, or RHR2 (FIG. 8E). There appears to be redundancy in glycerol-mediated response to stress such that deficiency of one enzyme can be compensated by activation of others in the glycerol biosynthesis pathway. Deletion of SCH9 greatly enhanced stress resistance to heat and $H_2O_2$ of rhr2Δ mutant, possibly due to the upregulation of the Hor2 level. Since glycerol phosphatases (Rhr2 and Hor2) are not the rate-limiting enzymes for glycerol production (Pahlman et al., 2001), upregulations of Gpd1 and Gpd2 may also contribute to the rescue of the rhr2Δ stress sensitive phenotype in cells lacking SCH9. A similar redundancy exists between Gpd1 and Gpd2. Although little or no effect was seen in either of the single deletion mutants, gpd1/2Δ double knockout strain is hypersensitive to heat and hydrogen peroxide treatment. The triple sch9Δ gpd1Δ gpd2Δ mutant showed severe growth defects and low saturation density in the liquid culture, which prevented us from utilizing this mutant for epistatic studies. Taken together, these results underscore the importance of glycerol biosynthesis in promoting cellular protection and life span extension in the SCH9 deficient mutants.

Mechanisms of Glycerol-Dependent Life Span Extension

Glycerol can protect against stress in part because of its function as a chemical chaperone (Meng et al., 2001; Deocaris, 2006; Wojda, 2003). To test the role of glycerol in protecting against heat-induced protein misfolding, we examined the activity loss and recovery of a heat sensitive bacterial luciferase (Parsell et al., 1994) in wild type and sch9Δ cells. Whereas exposing wild type cells to heat stress (55° C. for 1 hour) led to a ~80% reduction of luciferase activity, only a 20-40% loss of activity was observed in sch9Δ mutants (FIG. 9A), which is consistent with the enhanced stress resistance phenotype of sch9Δ (FIG. 4). However, pretreatment of wild type cells with low concentration of glycerol had no protective effect on the heat-induced loss and the recovery of luciferase activity (FIG. 9B), indicating the heat resistance phenotype of sch9Δ does not depend on extracellular glycerol. Similar results were obtained in the BY4741 genetic background.

Figure 9:
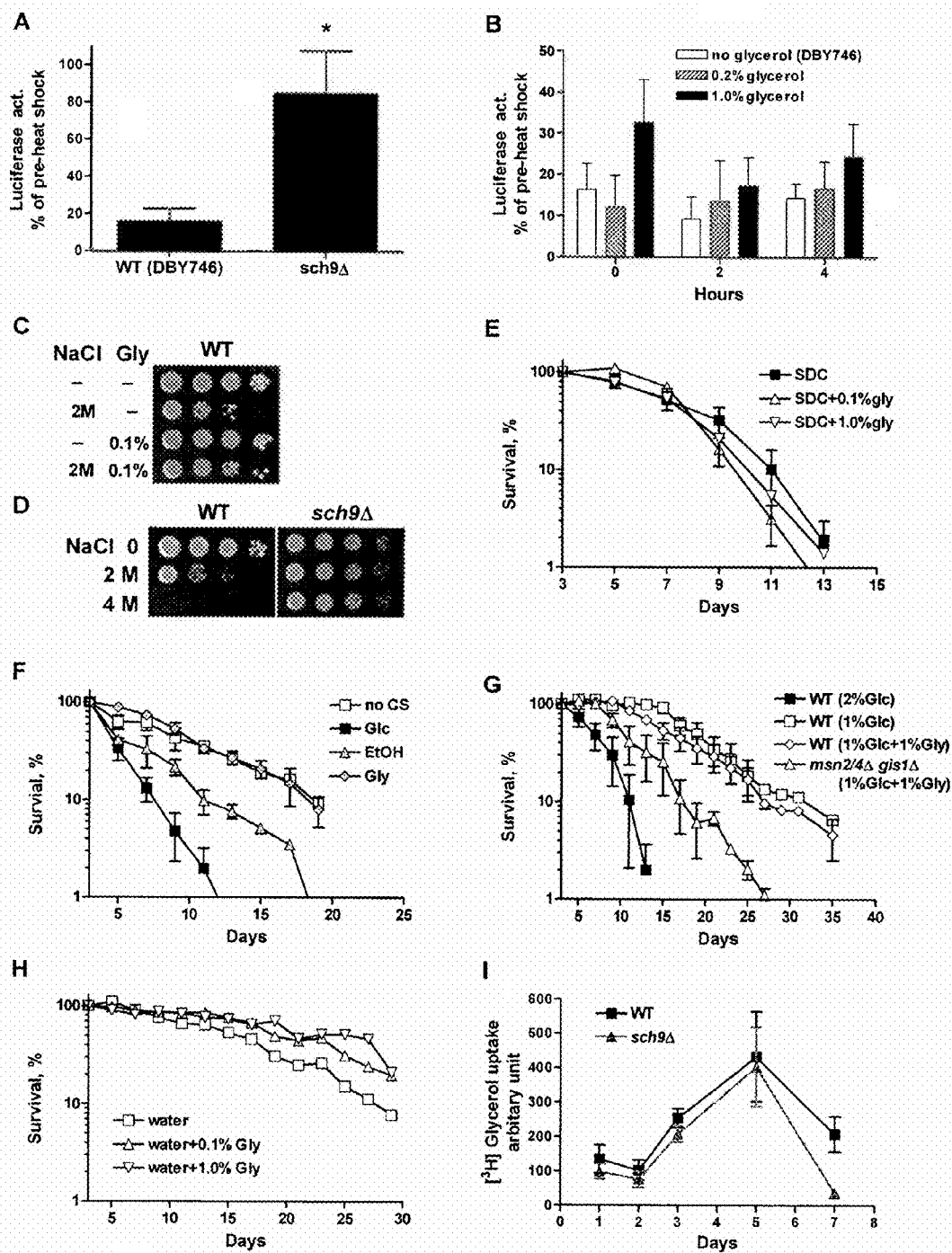
FIG. 9. Effect of glycerol on stress resistance and life span. (A) Day 3 wild type (DBY746) and sch9Δ mutants expressing bacterial heat-sensitive luciferase were subject to heat stress (42° C. for 60 min). Data represent mean and SEM, n=3. * p<0.05, unpaired t-test, two tailed. (B) Recovery of luciferase activity after heat stress (42° C. for 60 min) in wild type cells pre-treated with glycerol (with concentrations indicated) for 30 min. Data represent mean and SEM, n=3. (C) Day 3 wild type cells grown in SDC were washed 3 times with water and exposed to high concentrations of NaCl (2 M) with or without glycerol for 24 hours. The cells were then washed 3 times to remove the salt, serially diluted, and spotted on to YPD plate. (D) Day 3 wild type and sch9Δ mutants were exposed to high concentration of NaCl (2 and 4 M) for 24 hours. (E) Chronological survival of wild type cells grown in SDC supplemented with glycerol as indicated. Data represent mean and SEM, n=3. (F) in situ viability assay. Day 1 SDC wild type cultures were diluted and plated onto SC-Trp plates (no carbon source) or onto plates supplemented with glucose (Glc, 2%), ethanol (EtOH, 0.8%) or glycerol (Gly, 3%) as carbon source. Every two days, tryptophan (or with additional glucose) was added to the plates. Colony formation was monitored 2 days after the addition of tryptophan. Data represent mean and SEM, n=3. (G) Chronological survival of wild type (DBY746) and msn2Δ msn4Δ gis1Δ mutants grown in normal (SC+2% glucose), calorie-restricted (SC+1% glucose), or glucose/glycerol (SC+1%+1%) medium. Data represent mean and SEM of 4 cultures analyzed. (H) Day 3 wild type cells grown in SDC medium were washed three times with water and incubated in water (CR/extreme starvation) with or without glycerol (0.1% or 1%). Plot shows a representative experiment (mean of duplicates) repeated three times with similar results. (I) Yeast grown in SDC was sampled (1 ml) at indicated time points. [1,2,3-$^3$H] Glycerol (ARC, Inc) was added to the aliquot and incubated at 30° C. with shaking for 24 hours. Cells were then washed three times with water. The cellular [$^3$H]-content was determined by scintillation counting (Wallac 1410, Pharmacia) and normalized to cell number (viability by CFU). Data represent mean and SEM of 4 cultures analyzed.

Intracellular accumulation of glycerol also contributes to protection against osmotic stress (Albertyn et al., 1994; Wojda et al., 2003). Addition of 0.1% of glycerol to the medium slightly enhanced the resistance to osmotic stress of wild type yeast (FIG. 9C). When exposed to high concentration of NaCl, the sch9Δ and ras2Δ mutants exhibited enhanced resistance to hyperosmolarity compared to the tor1Δ mutant, which in turn was better protected than wild type cells (FIG. 9D), suggesting that increased resistance against hyperosmolarity may be part of the general stress response shared by all long-lived mutants. These data are also consistent with the reports that high osmolarity growth conditions extend both RLS and CLS in yeast (Kaeberlein et al., 2002; Murakami et al., 2008). With regard to life span, however, extracellular supplementation of glycerol (0.1% and 1%) to the wild type yeast culture at day 3, when the glycerol level is high in the long-lived sch9Δ mutants (FIG. 7B), did not show any beneficial effect (FIG. 9E).

Glycerol Provides a Carbon Source without Affecting the Anti-Aging Effect of Calorie-Restriction Ethanol, as a carbon source, elicits pro-aging signaling and promotes cell death. Removing ethanol either by evaporation or by switching yeast cells from expired medium to water, which represents a condition of extreme calorie restriction/starvation, extends yeast chronological life span (Fabrizio et al., 2005). The metabolic switch to ethanol utilization and glycerol biosynthesis removes the detrimental effect of pro-aging carbon sources (glucose and ethanol) and creates an environment that mimics calorie restriction in the sch9Δ mutant culture (FIG. 7D). To elucidate the role of different carbon sources on yeast survival, we used an in situ assay to monitor cell survival on plate, which allowed us: a) to study the effect of different carbon sources in the presence of all the other nutrients, b) to control the exact amount of carbon source to which the cells are exposed over the whole experiment, similarly to the experimental conditions used for the RLS studies of calorie restriction.

One day old tryptophan auxotrophic cells were plated on SC plates lacking tryptophan (SC-Trp). Every two days, tryptophan was added to one of the set of plates generated on the same day to allow growth and monitor survival. We monitored colony formation to determine the viability of the cells. The survival curve of approximately 200 wild type DBY746 cells plated onto SC plates supplemented with 2% glucose is reminiscent of that in the standard liquid medium paradigm (FIG. 9F). Removal of carbon source from the SC-Trp plates caused a 70% increase in mean life span, which was partially reversed by the presence of low concentration of ethanol (FIG. 9F) in agreement of our earlier findings (Fabrizio et al., 2005). Substitution of glucose with high level of glycerol (3%) did not trigger the pro-aging signaling as seen with glucose or ethanol (FIG. 9F). Thus, the metabolic switch to glycerol biosynthesis in the long-lived sch9Δ mutants may represent a genetically induced "carbon source substitution" that can be as effective as that of calorie restriction.

Life Span Extension after the Switch to Glycerol Medium Depends on CR-Transcription Factors Calorie restriction-induced cellular protection and life span extension in yeast depends on the protein kinase Rim15 and its downstream stress response transcription factors Msn2/4 and Gis1, all of which are negatively regulated by Sch9, Tor, and Ras (Wei et al., 2008). When yeast were grown in isocaloric medium containing either glucose (2%) or glucose/glycerol (1% each), a 1.5-fold increase in mean life span was observed in yeast cultured in glucose/glycerol medium (FIG. 9G). This pro-longevity effect of the glucose/glycerol diet was mostly dependent, as is that of calorie restriction, on the stress response transcriptional factors (FIG. 9G).

Glycerol is Taken Up by sch9Δ Mutants.

The metabolic switch in the sch9Δ mutants not only removes the pro-aging/death signaling from glucose/ethanol or other carbon sources but also produces a carbon source for long-term survival. We switched wild type cells from the ethanol-containing medium to water containing 0.1% glycerol. A small extension of life span was observed in addition to that of extreme calorie restriction (FIG. 9H), suggesting that glycerol may provide nutritional support or additional protection under the starvation condition. In fact, we show that yeast cells actively uptake the exogenous $[1,2,3-^3H]$ glycerol during the post-diauxic phase, entered by S. cerevisiae after most of the extracellular glucose is depleted (FIG. 9I). The utilization of glycerol is also supported by our microarray analysis, which shows that the genes involved in the catabolic metabolism of glycerol are up-regulated under the extreme calorie restriction/starvation (water) condition in wild type cells.

Figure 10:
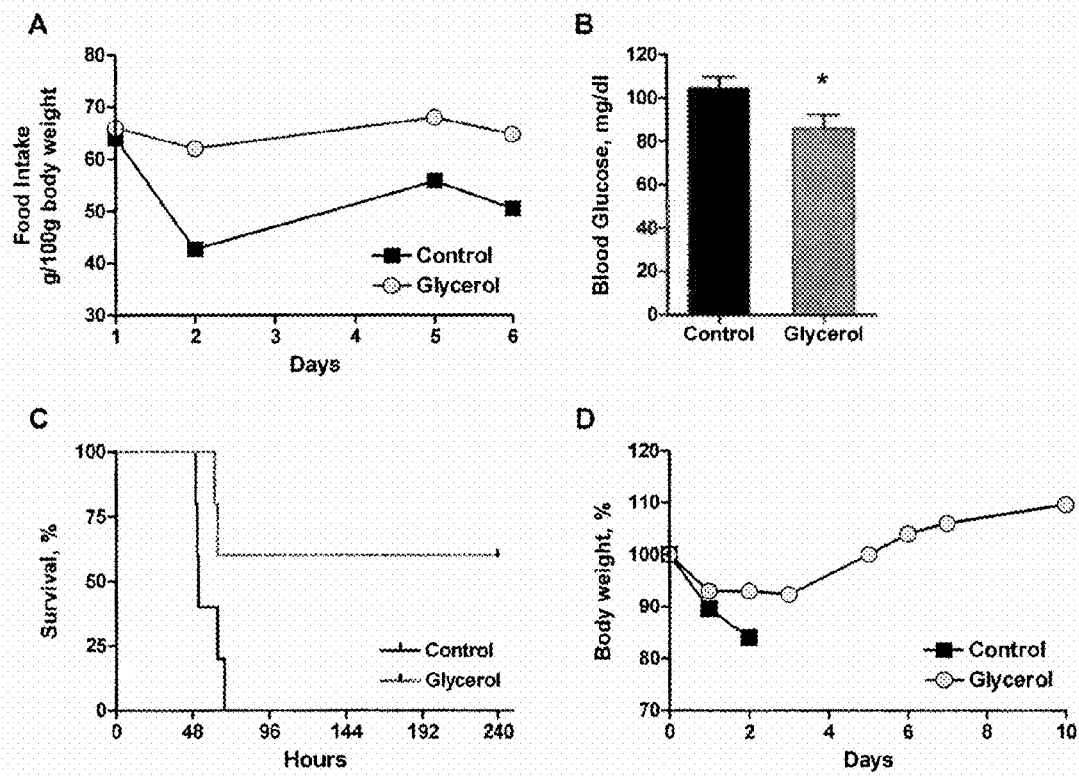
FIG. 10. Dietary substitution of sugar with glycerol protects mice from paraquat toxicity. Two groups of five mice each were ad libitum fed with either the control or glycerol diet for six days. (A) Food intake per 100 g body weight was slightly higher in the group fed with the glycerol diet. (B) Blood glucose levels were measured prior to paraquat injection (6 days after the initiation of diet. * p=0.05, unpaired t-test, two tailed.) (C) Survival curves after intraperitoneal injection of 50 mg/kg paraquat (7.5 mg/ml in PBS). (D) Body weight of mice after the paraquat treatment.

Substitution of Glycerol as Dietary Carbon Source Enhances Stress Resistance in Mice Calorie restriction enhances stress resistance and extends life span in model organism ranging from yeast to mammals (Longo, 2003; Kennedy et al., 2007; Masoro, 2005). In view of the beneficial effects of carbon source substitution with glycerol in life span and stress resistance in yeast, we studied the effect of CSC in mice. Two groups of five mice each were fed ad libitum for six days with two isocaloric diets, the control diet (Teklad 8604 chow supplemented with 40% starch/sucrose/maltose dextrin) or the glycerol diet (supplemented with 40% glycerol). Although the mice on the glycerol diet ate slightly more than those on the control diet, they showed an 18% reduction in blood glucose level by day 6 (FIGS. 10A and 10B). Both groups of mice were then given a single dose of 50 mg/kg paraquat intraperitoneally and put back on normal diet (8604 chow). Paraquat is known to cause S-phase arrest of liver and lung cells Matsubara et al., 1996) and lead to death (Migliaccio et al., 1999). All mice in the control group were dead by day 3, whereas three out of five glycerol-fed mice fully protected from the paraquat toxicity (FIG. 10C, p<0.05) and regained normal body weight five days after paraquat treatment (FIG. 10D). These results indicate that dietary carbon source substitution with glycerol enhances oxidative stress resistance in vivo and has the potential to mimic calorie restriction in higher eukaryotes.

Discussion

Model organisms such as yeast, worms, and flies have been instrumental in the discovery of life span regulatory pathways that have a common evolutionary origin. Among these, the insulin/IGF-I-like pathways control longevity in organisms as phylogenetically distant as yeast and mice. Akt, Tor, and Ras function in the mammalian IGF-I signaling pathway and have been implicated in life span regulation in different model organisms (Kennedy et al., 2007; Longo and Finch, 2003). In this study, we show that longevity regulatory pathways control the shift from respiration to glycolysis and glycerol biosynthesis. This metabolic switch, which leads to the removal of pro-aging carbon sources and glycerol accumulation, creates an environment in the sch9Δ culture that mimics calorie restriction without removing the carbon source.

The genetic and genomic data revealed two parallel longevity signaling pathways controlled by Sch9 and Ras, in agreement with our previous work (Fabrizio et al., 2001). The beneficial effects of reduced activities of both pathways is additive (FIGS. 4D and 4G), and the sch9Δ ras2Δ double mutant is one of the longest lived genetic mutants (Partridge and Gems, 2002). In agreement with the genetic data, the gene expression profile of the day 2.5-old ras2Δ mutant shows that approximately 67% of the genes differentially expressed are not significantly changed in the other two mutants (FIG. 5A). Our genetic analysis of the interactions between the Tor pathway and the other two life-span regulatory pathways indicates a stronger overlap between the Tor1 and Sch9 pathways in the regulation of stress resistance, longevity, and age-dependent genomic instability. It also suggests that TORC1 functions upstream of Sch9 in the regulation of these readouts in agreement with what has been proposed by others (Jorgensen et al., 2004) and with the demonstration of the direct phosphorylation of Sch9 by TORC1 (Urban et al., 2007). Our microarray analysis indicates similarities but also differences between the set of genes controlled by Tor and Ras. On the one hand, TOR1 deletion further increased the heat-shock resistance of ras2Δ mutants, and on the other hand no additional life span extension was observed. Furthermore, the overexpression of constitutively active Ras2 abolished CLS extension associated with deficiency of TOR1, suggesting an overlapping of the two pathways and possibly an upstream role of TORC1.

Despite the higher degree of differential expression profile observed in ras2Δ mutants, there are remarkable similarities in the expression pattern of genes involved in key metabolic pathways in all three long-lived mutants. The genome-wide association (transcription factor binding motif enrichment test) and the genetic analyses indicate that longevity modulation by the Tor/Sch9 and Ras signaling depends on the protein kinase Rim15 and its downstream stress response transcription factors, Msn2/4 and Gis1 (Cheng et al., 2007; Wei et al., 2008). The most striking result is that genes involved in glycolysis/fermentation are consistently upregulated, while mitochondrial related genes are down-regulated, in all three long-lived mutants, suggesting a cellular state that favors glycolysis and diminished mitochondrial functions including TCA cycle and oxidative phosphorylation. Part of our results may appear to contradict recent results showing that respiration is upregulated in the tor1Δ mutant (Bonawitz et al., 2007). This discrepancy may be explained by the difference in the time point of observation. Bonawitz and colleagues measured higher respiration rates in exponentially growing or day 1 tor1Δ cultures relative to wild type yeast. By day 2 this difference was no longer observed (Bonawitz et al., 2007). The role of respiration in replicative life span regulation is still unclear. On the one hand, increased respiration has been shown to mediate the beneficial effect of CR (0.5% glucose) (Lin et al., 2002); on the other hand, growth on lower glucose-containing medium (0.05% glucose) can extend the replicative life span of respiratory-deficient yeast (Kaeberlein et al., 2005a). Moreover, the studies from Jazwinski's group indicated that respiration does not directly affect replicative longevity (Kirchman et al., 1999). The different effect of respiration on life span may also be contributed to the experimental systems used for life span studies. The replicative life span analysis is mostly carried out on the solid rich YPD medium, where cells are constantly exposed to glucose and other nutrients. The energy required for growth is mainly derived from fermentation. In contrast, our chronological longevity studies are performed by monitoring population survival in a non-dividing phase in which fermentation is minimized (Fabrizio and Longo, 2003).

Figure 7:
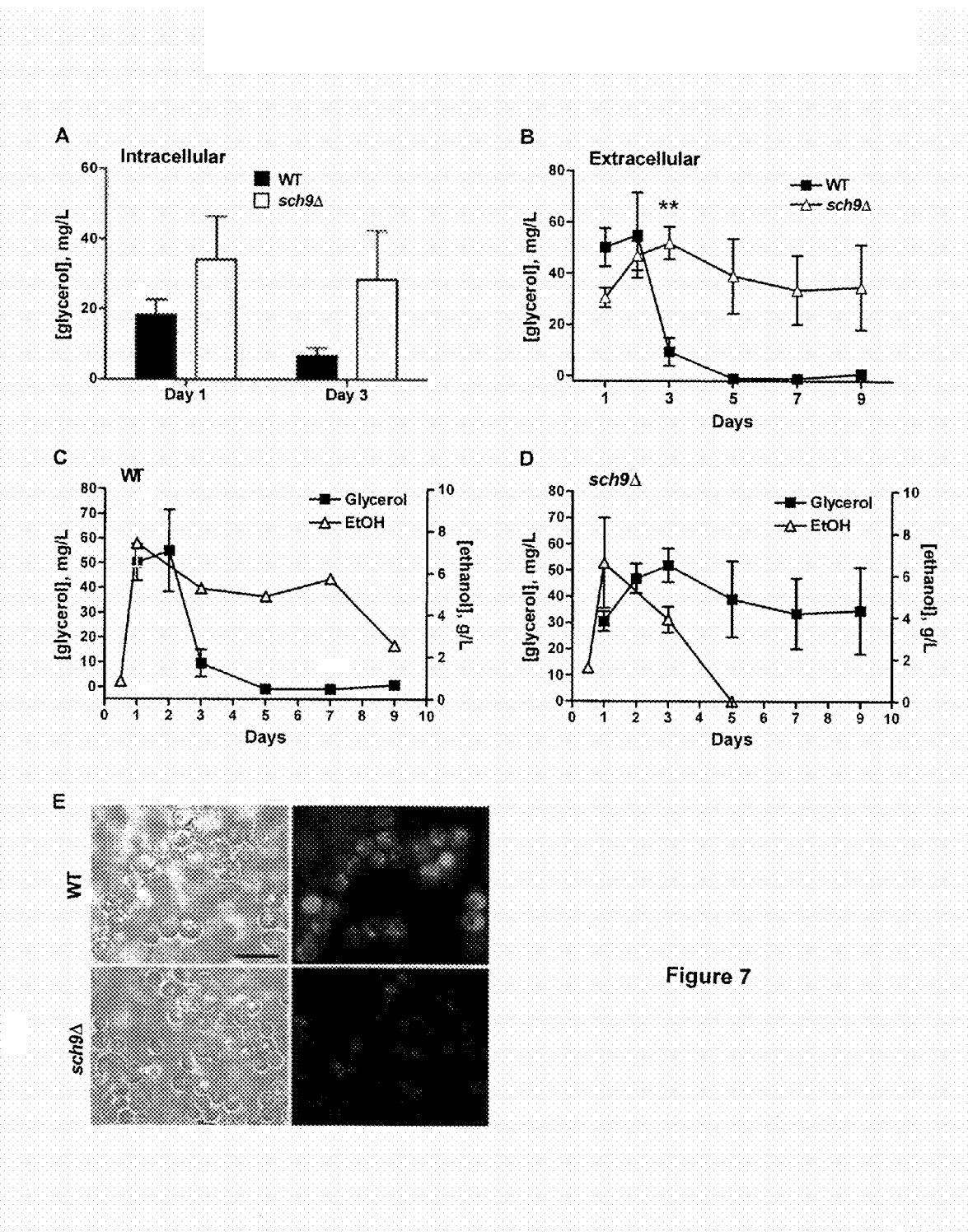
FIG. 7. Sch9 deficient mutants metabolize ethanol and accumulate glycerol. (A) Intracellular glycerol contents of wild type (DBY746) and cells lacking Sch9 were measured on day 1 and day 3. Data represent mean and SEM of 5 cultures analyzed. (B) Glycerol concentration in the medium of wild type and sch9Δ cultures. Data represent mean and SEM of 5-7 cultures analyzed. ** p<0.01, unpaired t-test, two-tailed, sch9Δ vs. WT. (C-D) Glycerol and ethanol concentrations in the medium of wild type (C) and sch9Δ (D) cultures. Data represent mean and SEM of 3-5 cultures analyzed. (E) Nile red staining of neutral lipids of day 1 wild type and sch9Δ mutants. Nile red staining is shown on the right, and phase contrast left. Bar, 10 µm.

The gene expression profiles of long-lived mutants showed induction of the expression of key genes required for glycerol biosynthesis. High levels of extracellular and intracellular glycerol were detected in the sch9Δ culture and triglyceride catabolism appeared to contribute to glycerol generation (FIG. 7). This shift towards the production of glycerol represents a fundamental metabolic change in the physiology of the long-lived mutants. Interestingly, mutants lacking Sir2, another gene implicated in CR-dependent and -independent life span regulation (Kaeberlein et al., 2005a; Kaeberlein et al., 1999; Lin et al., 2000), also deplete the pro-aging carbon source ethanol (Fabrizio et al., 2005). Expression profile analysis of the sir2Δ mutant, like the sch9Δ mutant, shows upregulation of glycerol biosynthetic genes, suggesting a role of glycerol biosynthesis in the Sir2-dependent life span regulation (Fabrizio et al., 2005).

Figure 8:
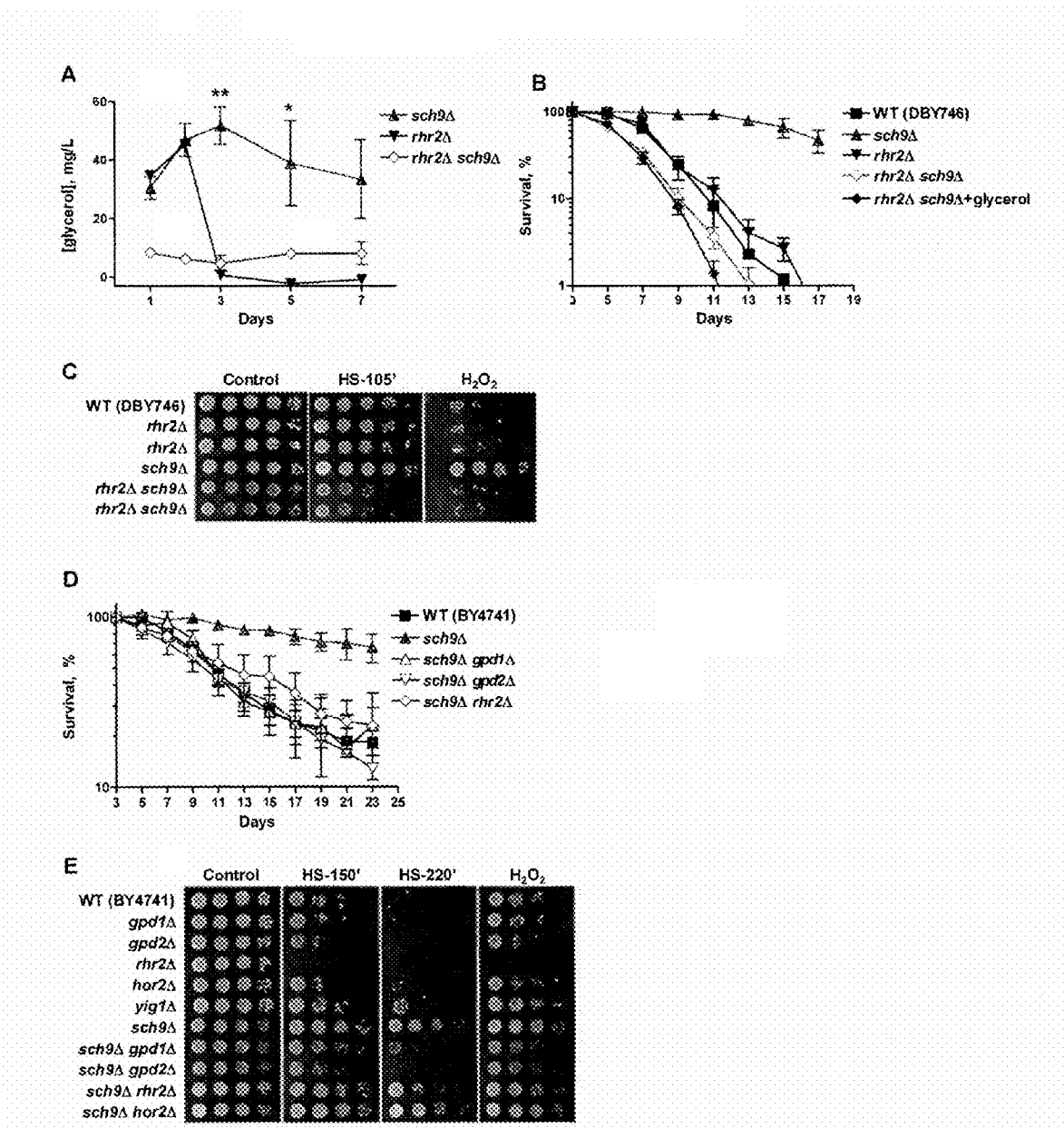
FIG. 8. Deletion of glycerol biosynthesis genes reverse life span extension and stress resistance associated with deficiency in Sch9. (A) Glycerol concentration in the medium. Data present mean and SEM of 4 cultures analyzed. * p<0.05, ** p<0.01, unpaired t-test, two tailed, sch9Δ vs. rhr2Δ sch9Δ. (B) Life span of wild type (DBY746), sch9Δ, rhr2Δ, and Sch9-deficient mutants lacking Rhr2. Glycerol (1%, final concentration) was added to the one day-old rhr2Δ sch9Δ culture. Data represent mean and SEM of 4-5 cultures analyzed. (C) Day 3 cells were exposed to heat shock (55° C. for 105 min) or $H_2O_2$ (150 mM for 60 min). Strains shown are wild type (DBY746), rhr2Δ, sch9Δ, rhr2Δ sch9Δ. (D) Life span of wild type (BY4741), sch9Δ, and Sch9-deficient mutants lacking Gpd1, Gpd2, or Rhr2. Data represent mean and SEM of 3 experiments. (E) Heat shock (55° C.) and oxidative stress ($H_2O_2$, 500 mM, 60 min) resistance of day 3 mutants lacking glycerol biosynthesis genes.

Genetic analysis performed by deleting genes required for glycerol biosynthesis in the sch9Δ mutant indicates that glycerol production is required for life span regulation and stress resistance (FIG. 8). Increased glycerol biosynthesis may contribute to life span regulation through several distinct mechanisms. First, cells lacking Sch9 utilize glucose and ethanol and accumulate glycerol, a non-pro-aging carbon source, which effectively leads to a "self-imposed" CSS. CR, achieved by lowering glucose in growth medium or removing ethanol extends the yeast CLS (Fabrizio et al., 2005; Smith et al., 2007; Wei et al., 2008). Conversely, addition of low concentration of ethanol reveres life span extension induced by CR or deletion of SCH9 (Fabrizio et al., 2005). Here we show that cells lacking Sch9 deplete pro-aging carbon sources and activate glycerol biosynthesis. In addition to acting as a "phantom carbon source" that does not promote aging as glucose or ethanol, glycerol caused a minor but further enhancement of survival of cells under starvation conditions, suggesting that it provides nutritional support, which was confirmed by its uptake by non-dividing cells (FIGS. 9H and 9I). Second, production and accumulation of glycerol may contribute to cellular protection since glycerol enhances resistance to osmotic stress and functions as molecular chaperone stabilizing/renaturing the newly synthesized or heat-inactivated proteins. Third, glycerol production may affect aging through the modulation of the redox balance of the cell, since its production contributes to the maintenance the of NAD:NADH ratio (Ansell et al., 1997; Bakker et al., 2001; Rigoulet et al., 2004). Easlon et al. have recently shown that overexpression of the malate-aspartate NADH shuttle components extends yeast replicative life span (Easlon et al., 2008). The latter two mechanisms, however, are less likely to contribute significantly to longevity promotion, as addition of exogenous glycerol to the culture had little or no effect on heat-induced protein inactivation (FIG. 9B) or chronological survival in wild type cells (FIG. 9E). Additionally, we overexpressed in wild type cells the bacterial NADH oxidase (NOX) or alternative oxidase (AOX), both of which increase NADH oxidation in yeast (Vemuri et al., 2007), did not significant alter the life span.

Our results in mice indicate that the replacement of part of the glucose-based carbohydrates in the diet with glycerol is sufficient to reduce blood glucose concentration and increase the resistance of mice to a lethal dose of paraquat. Thus, the self-generated CSS observed in yeast suggest that substitution of glucose with other carbon sources in the diet has potential applications for mammals. In light of the conservation of the aging pathways and the role of calorie restriction in extending life span of a wide range of species, it will be important to investigate further the possibility of an anti-aging role for glycerol in higher eukaryotes.

Experimental Procedures
Yeast Strains and Growth Conditions

All the strains used for the DNA micorarray analysis were originated in DBY746 (MATα, leu2-3, 112, his3Δ, trp1-289, ura3-52, GAL$^+$) by one-step gene replacement as described previously (Brachmann et al., 1998). Double deletion mutants were produced in the DBY746 and BY4741 (MATα, his3Δ1, leu2Δ0, met15Δ0, ura3Δ0). Strains overexpressing SCH9, or ras2$^{val19}$ were generated by transforming DBY746 with plasmids pHA-SCH9 (a gift from Dr. Morano University of Texas Medical School) or pMW101 (plasmid RS416 carrying Cla I-ras2$^{val19}$-Hind III fragment of pMF100, a gift from Dr. Broach, Princeton University), respectively. Strains expressing a heat sensitive bacterial luciferase (Parsell, 1994) was generated by transforming yeast with plasmid pGPD-luxAB (Addgene.com). Yeast chronological life span was measured as described previously (Fabrizio and Longo, 2003). Briefly, yeast were grown in SDC containing 2% glucose, and supplemented with amino acids, adenine and uracil as described (Fabrizio and Longo, 2003). Yeast viability was measured by monitoring Colony Forming Units (CFUs) every 48 hours. The number of CFUs at day 3 was considered to be the initial survival (100%) and was used to determine the age-dependent mortality. For viability assay on plate, day 1 SDC cultures of tryptophan auxotrophic strains were diluted and plated on to SC-Trp plates (~200 cells/plate) with no carbon source, or supplemented with glucose (2%) or glycerol (3%). Plates were incubated at 30° C. for the duration of the experiment. Every two days 0.5 ml of 2 mg/ml tryptophan was added to the plates. For plates without glucose, 1 ml of 5% glucose was added to the plates in additional to tryptophan. Colony formation was monitored after 2-3 days incubation at 30° C.

DNA Microarray Analysis and Data Processing

Day 2.5 yeast from wild type and mutants cultures (n=3) were harvested and total RNA was extracted by the acid phenol method. The cRNA was hybridized to Affymetrix GeneChip Yeast 2.0 array to obtain the measurement of gene expression. The Bioconductor Affy Package was adopted to process the microarray data (Bioconductor). The "Invariant Set" approach was used for normalization at the probe level, and the "Model based" method to summarize and obtain expression for each probe set (Li and Hong, 2001). High consistency was achieved between the replicates from the same strain, with the Pearson correlate on coefficients greater than 0.96 at the gene level.

GO Analysis

The Gene Ontology GO (see the website genome-ftp.stanford.edu/pub/go/ontology/) data were organized as a directed acyclic graph (DAG), in which each node corresponded to a set of genes with specific annotations. In our analysis, only the GO categories that were well annotated and contain enough number of genes (≥30 genes) for statistical analysis were included, which were defined as terminal informative GO (TIGO) categories: 44 cellular component, 53 molecular function, and 109 biological process. Wilcoxon rank test was performed to examine whether a TIGO category was significantly up- or down-regulated. Finally, q-values for each test were calculated to correct the multiple testing errors using the "qvalue" package (Storey and Tibshirani, 2003).

Stress Resistance Assays

Heat shock resistance was measured by spotting serial dilutions of cells removed from day 3 post-diauxic phase cultures onto YPD plates and incubating at 55° C. (heat-shocked) and at 30° C. (control) for 60-150 min. After the heat-shock, plates were transferred to 30° C. and incubated for 2-3 days. For oxidative stress resistance assays, day 3 cells were diluted to an OD$_{600}$ of 1 in K-phosphate buffer, pH6, and treated with 100-200 mM of hydrogen peroxide for 60 minutes. Alternatively, cells were treated with 250 µM of menadione for 30 min in K-phosphate buffer, pH7.4. Serial dilutions of control or treated cells were spotted onto YPD plates and incubated at 30° C. for 2-3 days. For osmotic stress resistance assay, day 3 cells were washed twice with water and resuspended in salt buffer (2 or 4 M NaCl). After incubating at 30° C. for 24 h with shacking, cells were washed with water to eliminate salt, serially diluted, and then plated on to YPD plates. Plates were incubated 2-3 days at 30° C.

Nile Red Staining

Cells (1 ml SDC culture) were washed once with PBS and resuspended in 1 ml PBS. 10 µl of Nile Red (0.1 mg/ml in acetone) was added to the cell suspension, and incubated at room temperature, in the dark, for 5 min. Cells were washed once with PBS and imaged with a Leica fluorescent microscope.

Glycerol Measurement

For intracellular glycerol content, cells were washed three times with water. Cell pellest from 1 ml culture were resuspended in 0.5 ml of Tris buffer (0.1 M, pH7.4), and then boiled for 5 min followed by a 30 sec spin to remove cell debris. The supernatant from the cell extract or the medium cleared of cells was used to determine intracellular or extracellular glycerol level, respectively. Glycerol concentration was measured using an UV-based glycerol assay kit (Boehringer Mannheim/R-Biopharm). The manufacturer recommended protocol was modified to adapt the assay to a 96-well plate format. Each sample was assayed in duplicates and data were fitted to standard curve generated by serial dilutions of stock glycerol.

Luciferase Assay

Heat inactivation of luciferase was measured as previously described (Parsell, 1994). Briefly, yeast expressing heat-sensitive bacterial luciferase were subject to heat shock (42° C. for 60 min). Ten minutes before the end of heat shock, cycloheximide (20 uM final) was added to the culture. The culture was sampled and mixed with the luciferase substrate decanol (Sigma) and signal was immediately measured in a luminometer (Luminoskan Ascent, Thermo Scientific).

Paraquat Toxicity in Mice

Six-week old A/J mice, weighing 18-24 g, were put on two diet for 6 days: the control diet (Teklad 8604 chow supplemented with 40% starch/sucrose/maltose dextrin) or with glycerol diet (Teklad 8604 chow supplemented with 40% glycerol). Blood glucose level was measured using Precision Xtra test strip (Abbott Laboratories). Paraquat (7.5 mg/ml, in phosphate buffered saline) was injected intraperitoneally (50 mg/kg). Immediately following paraquat administration, mice were kept on normal diet (Diet 8604, Harlan Teklad). Mice were monitored every 2 hours for 4 days and body weight was recorded once daily throughout the experiment. Mice were sacrificed when they showed signs of stress or pain and determined to have no chance of recovery.

REFERENCES

Albertyn, J., Hohmann, S., and Prior, B. A. (1994). Characterization of the osmotic-stress response in *Saccharomyces cerevisiae*: osmotic stress and glucose repression regulate glycerol-3-phosphate dehydrogenase independently. Curr Genet 25, 12-18.

Ansell, R., Granath, K., Hohmann, S., Thevelein, J. M., and Adler, L. (1997). The two isoenzymes for yeast NAD+-dependent glycerol 3-phosphate dehydrogenase encoded by GPD1 and GPD2 have distinct roles in osmoadaptation and redox regulation. Embo J 16, 2179-2187.

Bakker, B. M., Overkamp, K. M., van Maris, A. J., Kotter, P., Luttik, M. A., van Dijken, J. P., and Pronk, J. T. (2001). Stoichiometry and compartmentation of NADH metabolism in *Saccharomyces cerevisiae*. FEMS Microbiol Rev 25, 15-37.

Bonawitz, N. D., Chatenay-Lapointe, M., Pan, Y., and Shadel, G. S. (2007). Reduced TOR signaling extends chronological life span via increased respiration and upregulation of mitochondrial gene expression. Cell Metab 5, 265-277.

Brachmann, C. B., Davies, A., Cost, G. J., Caputo, E., Li, J., Hieter, P., and Boeke, J. D. (1998). Designer deletion strains derived from *Saccharomyces cerevisiae* S288C: a useful set of strains and plasmids for PCR-mediated gene disruption and other applications. Yeast 14, 115-132.

Cheng, C., Fabrizio, P., Ge, H., Longo, V. D., and Li, L. M. (2007). Inference of transcription modification in long-live yeast strains from their expression profiles. BMC Genomics 8, 219.

Easlon, E., Tsang, F., Skinner, C., Wang, C., and Lin, S. J. (2008). The malate-aspartate NADH shuttle components are novel metabolic longevity regulators required for calorie restriction-mediated life span extension in yeast. Genes Dev 22, 931-944.

Fabrizio, P., Battistella, L., Vardavas, R., Gattazzo, C., Liou, L. L., Diaspro, A., Dossen, J. W., Gralla, E. B., and Longo, V. D. (2004). Superoxide is a mediator of an altruistic aging program in *Saccharomyces cerevisiae*. J Cell Biol 166, 1055-1067.

Fabrizio, P., Gattazzo, C., Battistella, L., Wei, M., Cheng, C., McGrew, K., and Longo, V. D. (2005). Sir2 blocks extreme life-span extension. Cell 123, 655-667.

Fabrizio, P., Liou, L. L., Moy, V. N., Diaspro, A., Valentine, J. S., Gralla, E. B., and Longo, V. D. (2003). SOD2 functions downstream of Sch9 to extend longevity in yeast. Genetics 163, 35-46.

Fabrizio, P., and Longo, V. D. (2003). The chronological life span of *Saccharomyces cerevisiae*. Aging Cell 2, 73-81.

Fabrizio, P., Pozza, F., Pletcher, S. D., Gendron, C. M., and Longo, V. D. (2001). Regulation of longevity and stress resistance by Sch9 in yeast. Science 292, 288-290.

Granath, K., Modig, T., Forsmark, A., Adler, L., and Liden, G. (2005). The YIG1 (YPL201c) encoded protein is involved in regulating anaerobic glycerol metabolism in *Saccharomyces cerevisiae*. Yeast 22, 1257-1268.

Gray, J. V., Petsko, G. A., Johnston, G. C., Ringe, D., Singer, R. A., and Werner-Washburne, M. (2004). "Sleeping beauty": quiescence in *Saccharomyces cerevisiae*. Microbiol Mol Biol Rev 68, 187-206.

Hansen, M., Taubert, S., Crawford, D., Libina, N., Lee, S. J., and Kenyon, C. (2007). Lifespan extension by conditions that inhibit translation in *Caenorhabditis elegans*. Aging Cell 6, 95-110.

Holzenberger, M. (2004). The GH/IGF-I axis and longevity. Eur J Endocrinol 151 Suppl 1, S23-27.

Jia, K., Chen, D., and Riddle, D. L. (2004). The TOR pathway interacts with the insulin signaling pathway to regulate *C. elegans* larval development, metabolism and life span. Development 131, 3897-3906.

Jorgensen, P., Rupes, I., Sharom, J. R., Schneper, L., Broach, J. R., and Tyers, M. (2004). A dynamic transcriptional network communicates growth potential to ribosome synthesis and critical cell size. Genes Dev 18, 2491-2505.

Kaeberlein, M., Andalis, A. A., Fink, G. R., and Guarente, L. (2002). High osmolarity extends life span in *Saccharomyces cerevisiae* by a mechanism related to calorie restriction. Mol Cell Biol 22, 8056-8066.

Kaeberlein, M., Hu, D., Kerr, E. O., Tsuchiya, M., Westman, E. A., Dang, N., Fields, S., and Kennedy, B. K. (2005a). Increased life span due to calorie restriction in respiratory-deficient yeast. PLoS Genet 1, e69.

Kaeberlein, M., and Kennedy, B. K. (2005). Large-scale identification in yeast of conserved ageing genes. Mech Ageing Dev 126, 17-21.

Kaeberlein, M., McVey, M., and Guarente, L. (1999). The SIR2/3/4 complex and SIR2 alone promote longevity in *Saccharomyces cerevisiae* by two different mechanisms. Genes Dev 13, 2570-2580.

Kaeberlein, M., Powers, R. W., 3rd, Steffen, K. K., Westman, E. A., Hu, D., Dang, N., Kerr, E. O., Kirkland, K. T., Fields, S., and Kennedy, B. K. (2005b). Regulation of yeast replicative life span by TOR and Sch9 in response to nutrients. Science 310, 1193-1196.

Kapahi, P., Zid, B. M., Harper, T., Koslover, D., Sapin, V., and Benzer, S. (2004). Regulation of lifespan in *Drosophila* by modulation of genes in the TOR signaling pathway. Curr Biol 14, 885-890.

Kennedy, B. K., Austriaco, N. R., Jr., and Guarente, L. (1994). Daughter cells of *Saccharomyces cerevisiae* from old mothers display a reduced life span. J Cell Biol 127, 1985-1993.

Kennedy, B. K., Steffen, K. K., and Kaeberlein, M. (2007). Ruminations on dietary restriction and aging. Cell Mol Life Sci 64, 1323-1328.

Kenyon, C. (2001). A conserved regulatory system for aging. Cell 105, 165-168.

Kirchman, P. A., Kim, S., Lai, C. Y., and Jazwinski, S. M. (1999). Interorganelle signaling is a determinant of longevity in *Saccharomyces cerevisiae*. Genetics 152, 179-190.

Li, H., and Hong, F. (2001). Cluster-Rasch models for microarray gene expression data. Genome Biol 2, RESEARCH0031.

Lillie, S. H., and Pringle, J. R. (1980). Reserve carbohydrate metabolism in *Saccharomyces cerevisiae*: responses to nutrient limitation. J Bacteriol 143, 1384-1394.

Lin, S. J., Defossez, P. A., and Guarente, L. (2000). Requirement of NAD and SIR2 for life-span extension by calorie restriction in *Saccharomyces cerevisiae*. Science 289, 2126-2128.

Lin, S. J., Kaeberlein, M., Andalis, A. A., Sturtz, L. A., Defossez, P. A., Culotta, V. C., Fink, G. R., and Guarente, L. (2002). Calorie restriction extends *Saccharomyces cerevisiae* lifespan by increasing respiration. Nature 418, 344-348.

Loewith, R., Jacinto, E., Wullschleger, S., Lorberg, A., Crespo, J. L., Bonenfant, D., Oppliger, W., Jenoe, P., and Hall, M. N. (2002). Two TOR complexes, only one of which is rapamycin sensitive, have distinct roles in cell growth control. Mol Cell 10, 457-468.

Longo, V. D. (2004). Ras: the other pro-aging pathway. Sci Aging Knowledge Environ 2004, pe36.

Longo, V. D., and Fabrizio, P. (2002). Regulation of longevity and stress resistance: a molecular strategy conserved from yeast to humans? Cell Mol Life Sci 59, 903-908.

Longo, V. D., and Finch, C. E. (2003). Evolutionary medicine: from dwarf model systems to healthy centenarians? Science 299, 1342-1346.

Masoro, E. J. (2005). Overview of caloric restriction and ageing. Mech Ageing Dev 126, 913-922.

Matsubara, M., Yamagami, K., Kitazawa, Y., Kawamoto, K., and Tanaka, T. (1996). Paraquat causes S-phase arrest of rat liver and lung cells in vivo. Arch Toxicol 70, 514-518.

Meng, F., Park, Y., and Zhou, H. (2001). Role of proline, glycerol, and heparin as protein folding aids during refolding of rabbit muscle creatine kinase. Int J Biochem Cell Biol 33, 701-709.

Migliaccio, E., Giorgio, M., Mele, S., Pelicci, G., Reboldi, P., Pandolfi, P. P., Lanfrancone, L., and Pelicci, P. G. (1999). The p66shc adaptor protein controls oxidative stress response and life span in mammals. Nature 402, 309-313.

Mortimer, R. K., and Johnston, J. R. (1959). Life span of individual yeast cells. Nature 183, 1751-1752.

Murakami, C. J., Burtner, C. R., Kennedy, B. K., and Kaeberlein, M. (2008). A method for high-throughput quantitative analysis of yeast chronological life span. J Gerontol A Biol Sci Med Sci 63, 113-121.

Norbeck, J., Pahlman, A. K., Akhtar, N., Blomberg, A., and Adler, L. (1996). Purification and characterization of two isoenzymes of DL-glycerol-3-phosphatase from *Saccharomyces cerevisiae*. Identification of the corresponding GPP1 and GPP2 genes and evidence for osmotic regulation of Gpp2p expression by the osmosensing mitogen-activated protein kinase signal transduction pathway. J Biol Chem 271, 13875-13881.

Ozcan, S., and Johnston, M. (1999). Function and regulation of yeast hexose transporters. Microbiol Mol Biol Rev 63, 554-569.

Pahlman, A. K., Granath, K., Ansell, R., Hohmann, S., and Adler, L. (2001). The yeast glycerol 3-phosphatases Gpp1p and Gpp2p are required for glycerol biosynthesis and differentially involved in the cellular responses to osmotic, anaerobic, and oxidative stress. J Biol Chem 276, 3555-3563.

Paradis, S., Ailion, M., Toker, A., Thomas, J. H., and Ruvkun, G. (1999). A PDK1 homolog is necessary and sufficient to transduce AGE-1 PI3 kinase signals that regulate diapause in *Caenorhabditis elegans*. Genes Dev 13, 1438-1452.

Parks, L. W., Smith, S. J., and Crowley, J. H. (1995). Biochemical and physiological effects of sterol alterations in yeast—a review. Lipids 30, 227-230.

Parsell, D. A., Kowal, A. S., Singer, M. A., and Lindquist, S. (1994). Protein disaggregation mediated by heat-shock protein Hsp104. Nature 372, 475-478.

Partridge, L., and Gems, D. (2002). Mechanisms of ageing: public or private? Nat Rev Genet 3, 165-175.

Powers, R. W., 3rd, Kaeberlein, M., Caldwell, S. D., Kennedy, B. K., and Fields, S. (2006). Extension of chronological life span in yeast by decreased TOR pathway signaling. Genes Dev 20, 174-184.

Rigoulet, M., Aguilaniu, H., Averet, N., Bunoust, O., Camougrand, N., Grandier-Vazeille, X., Larsson, C., Pahlman, I. L., Manon, S., and Gustafsson, L. (2004). Organization and regulation of the cytosolic NADH metabolism in the yeast *Saccharomyces cerevisiae*. Mol Cell Biochem 256-257, 73-81.

Smith, D. L., Jr., McClure, J. M., Matecic, M., and Smith, J. S. (2007). Calorie restriction extends the chronological lifespan of *Saccharomyces cerevisiae* independently of the Sirtuins. Aging Cell 6, 649-662.

Storey, J. D., and Tibshirani, R. (2003). Statistical significance for genomewide studies. Proc Natl Acad Sci USA 100, 9440-9445.

Urban, J., Soulard, A., Huber, A., Lippman, S., Mukhopadhyay, D., Deloche, O., Wanke, V., Anrather, D., Ammerer, G., Riezman, H., et al. (2007). Sch9 is a major target of TORC1 in *Saccharomyces cerevisiae*. Mol Cell 26, 663-674.

Vellai, T., Takacs-Vellai, K., Zhang, Y., Kovacs, A. L., Orosz, L., and Muller, F. (2003). Genetics: influence of TOR kinase on lifespan in *C. elegans*. Nature 426, 620.

Vemuri, G. N., Eiteman, M. A., McEwen, J. E., Olsson, L., and Nielsen, J. (2007). Increasing NADH oxidation reduces overflow metabolism in *Saccharomyces cerevisiae*. Proc Natl Acad Sci USA 104, 2402-2407.

Wei, M., Fabrizio, P., Hu, J., Ge, H., Cheng, C., Li, L., and Longo, V. D. (2008). Life span extension by calorie restriction depends on Rim15 and transcription factors downstream of Ras/PKA, Tor, and Sch9. PLoS Genet 4, e13.

Werner-Washburne, M., Braun, E., Johnston, G. C., and Singer, R. A. (1993). Stationary phase in the yeast *Saccharomyces cerevisiae*. Microbiol Rev 57, 383-401.

Wojda, I., Alonso-Monge, R., Bebelman, J. P., Mager, W. H., and Siderius, M. (2003). Response to high osmotic conditions and elevated temperature in *Saccharomyces cerevisiae* is controlled by intracellular glycerol and involves coordinate activity of MAP kinase pathways. Microbiology 149, 1193-1204.

Zurita-Martinez, S. A., and Cardenas, M. E. (2005). Tor and cyclic AMP-protein kinase A: two parallel pathways regulating expression of genes required for cell growth. Eukaryot Cell 4, 63-71.

EXAMPLE III

Abstract

Starvation is well known to switch organisms ranging from *E. coli* to mice to a mode that renders them remarkably resistant to a variety of insults including oxidative damage. Previous studies demonstrated that a 48-hour fast was effective in protecting mice but not cancer cells against chemotherapy (Differential Stress Resistance) in agreement with the role of oncogenes in the negative regulation of protective systems. Patients are generally advised by the oncologist to eat normally prior to chemotherapy since fasting is considered by many to be potentially harmful to patients receiving chemotherapy, in part because a significant portion of patients have lost weight or have been weakened by prior chemotherapy cycles. Here we describe 10 cases of patients diagnosed with a variety of malignancies that have voluntarily fasted prior to (48-140 hours) and following (24-56 hours) chemotherapy treatments. None of the 10 patients, who received an average of 4 cycles of chemotherapy in combination with fasting, reported any significant side effects caused by the fasting itself other than hunger. Self-reported side-effects based on the common toxicity criteria (CTC) in five patients that received chemotherapy with or without fasting indicates that fasting may protect against fatigue, weakness and gastrointestinal side effects. In all the patients for whom it was possible to monitor cancer progression, fasting did not prevent the chemotherapy-dependent reduction in tumor markers or in mass size. Although controlled clinical trials are required to determine the role of fasting in the enhancement of therapeutic index, the 10 cases presented here indicate that fasting in combination with chemotherapy appears to be safe and has the potential to be highly beneficial.

Introduction

Chemotherapy can extend survival in patients diagnosed with a wide range of malignancies but its toxicity to normal cells and tissue limits dose intensity, frequency, and efficacy. For instance, the use of doxorubicin or cisplatin can effectively treat many malignancies, but the drug-induced cardiotoxicity and nephrotoxicity, respectively, limit their full potential. Therefore, reduction of undesired toxicity by selective protection of normal cells without compromising the toxicity to malignant cells represents a promising strategy to enhance cancer treatment.

Recently, a fasting-based intervention capable of differentially protecting normal but not cancer cells against high-dose chemotherapy in cell culture and in neuroblastoma-bearing mice was reported (Raffaghello 2008 PNAS). In the neuroblastoma xenograft mouse model, mice were allowed to consume only water for 48 hours prior to high-dose etoposide treatment. Fasting was highly effective in protecting mice treated with high dose etoposide, which caused 50% lethality in ad lib fed mice, yet caused a major delay in the neuroblastoma metastases-dependent death (Raffaghello 2008 PNAS).

Here we present 10 cases for patients diagnosed with various types of cancers, who voluntarily fasted prior to and following chemotherapy. Although properly controlled clinical trials are necessary to determine the efficacy of fasting in differential protection of normal and cancer cells the results presented here based on patient self-reported health outcomes and blood readouts suggest that fasting was safe and may have reduced multiple side effects caused by chemotherapy without preventing the killing of cancer cells.

Results

Ten cancer patients, 7 females and 3 males of a median age of 61 years (range 44-78) receiving chemotherapy are presented in this case series. 4 suffered from breast cancer, 2 from prostate cancer, and 4 from either ovarian, uterine, non small cell carcinoma of the lung, or esophageal adenocarcinoma. All these patients had voluntarily fasted for a total of 48 to 140 hours prior to and 24 to 40 hours following chemotherapy under the supervision of their treating oncologists. All patients tolerated fasting well. Hunger, and decrease in blood pressure were common symptoms cited by the patients after the prolonged fasting periods.

Figure 11A:
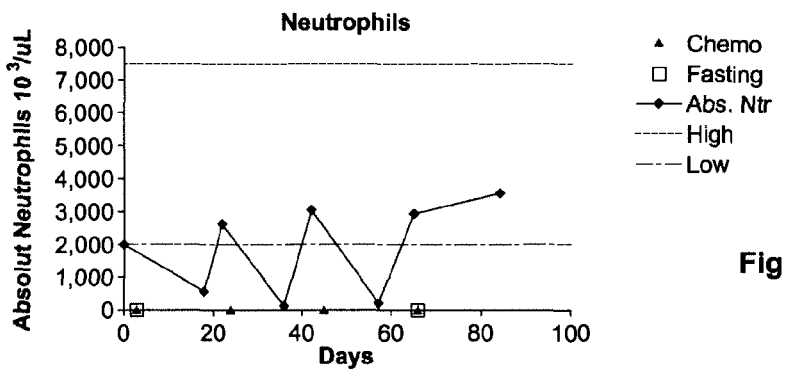
FIG. 11. Laboratory values of blood cell counts for case 1. (A) Neutrophils; (B) Lymphocytes; (C) White blood cells, WBC; (D) Red blood cells, RBC; (E) Platelets; (F) Haemoglobin, Hgb; (G) Haematocrit, Hct; (H) Body weight.
Figure 11B:
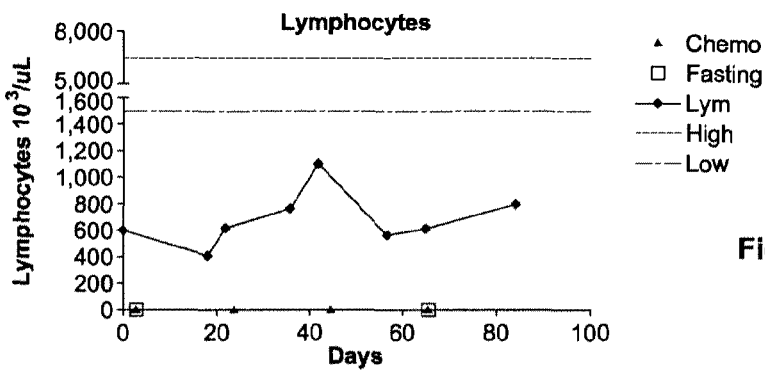
Figure 11C:
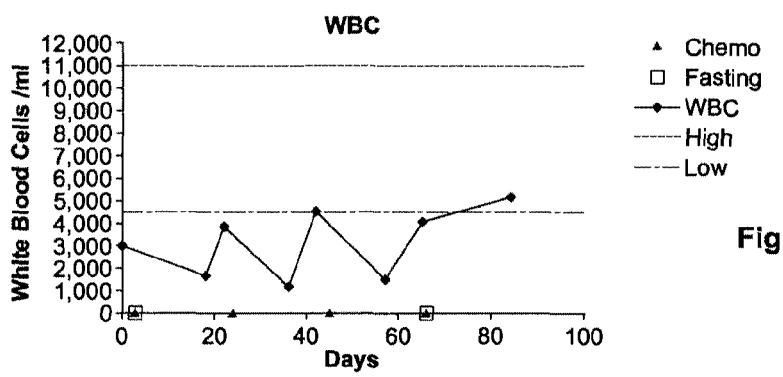
Figure 11D:
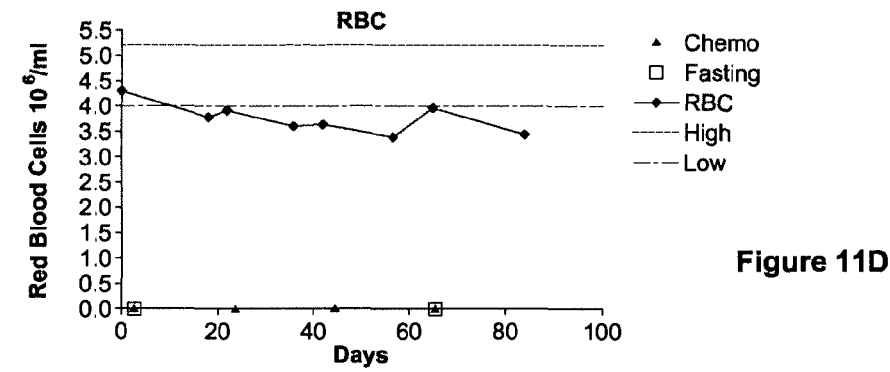
Figure 11E:
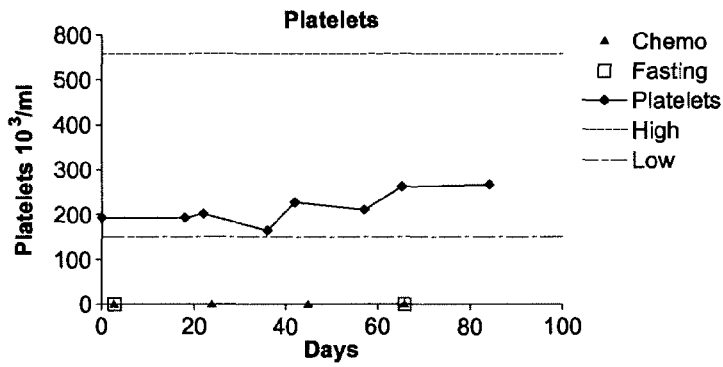
Figure 11F:
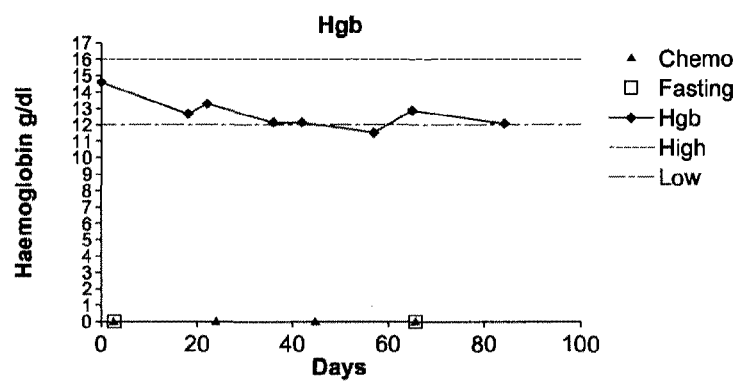
Figure 11G:
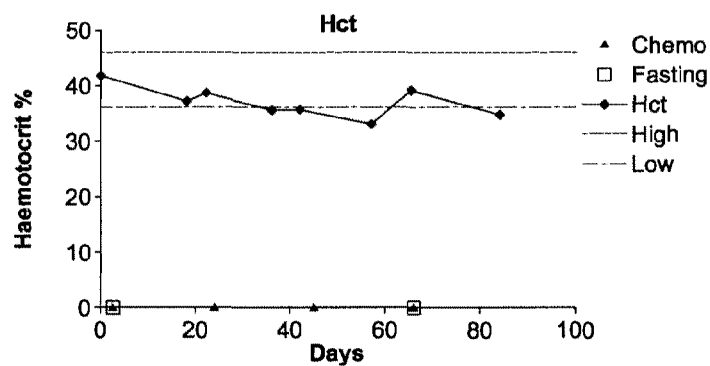
Figure 11H:
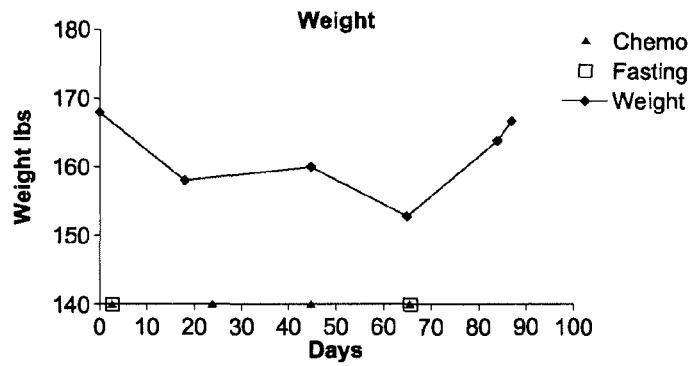
Figure 12:
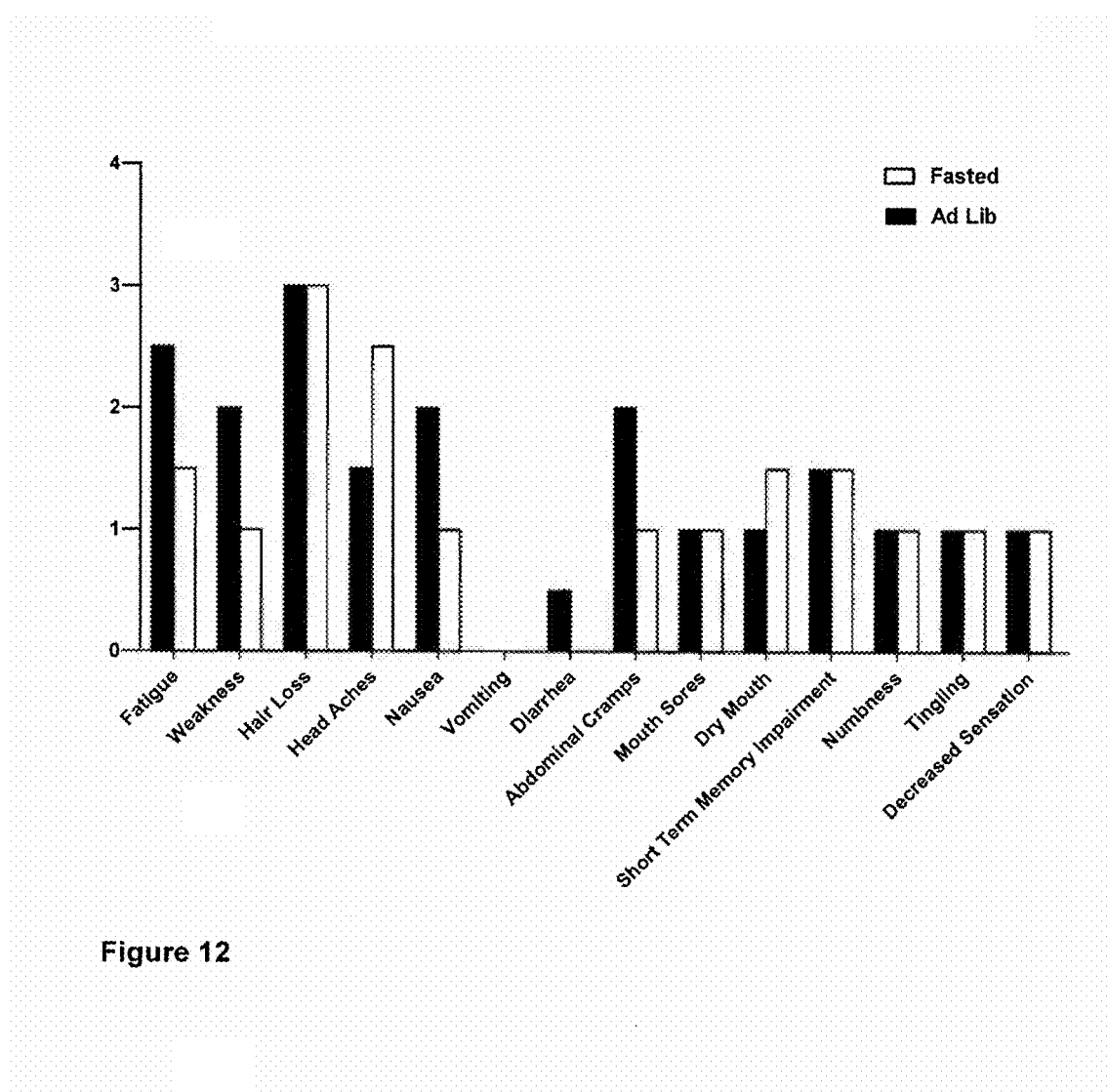
FIG. 12. Self-reported side-effects after chemotherapy for case 1.

Case 1:

A 51 years old woman with stage IIA breast cancer for whom adjuvant chemotherapy with docetaxel (DTX) and cyclophosphamide (CP) was recommended. She fasted prior to her first chemotherapy cycle. The fasting regimen consisted of a complete caloric deprivation for 120 hours prior to chemotherapy and 60 hours following it (180 hours total), during which she consumed only water and vitamins. The patient completed this prolonged fasting without major inconvenience and lost 7 pounds which were recovered within days after breaking the fast (FIG. 11H). During the three days post to the first chemodrug administration, the patient experienced mild fatigue, dry mouth and hiccups; nevertheless she was able to carry her daily activities (working up to 12 hours a day). In contrast, in the subsequent chemo-treatment cycles (second and third), she received chemotherapy without fasting and complained of moderate-severe nausea, vomiting, abdominal cramps, diarrhea and fatigue (FIG. 12). These severe side effects forced her to withdraw from her regular work schedule. For the $4^{th}$ and last cycle, she opted to fast once again, although with a different regimen. This regimen consisted of fasting 120 hours prior to and 24 hours post chemotherapy. Notably her self-reported side effects were lower despite the expected cumulative damage from her previous treatments. In agreement with the patient self report on the toxicity, the blood analysis readouts support that fasting may have a beneficial effect in protecting blood cells. After the $4^{th}$ chemotherapy cycle which followed a total of 140-hour fast the neutrophil, wbc, and platelet counts reached the highest level since the beginning of the chemotherapy 80 days earlier (FIGS. 11A, C and E). Notably, the counts at the anticipated nadir were not available. Overall, the blood cell counts and self-reported surveys suggest that fasting was safe and may conferred protection against the toxic side effects of chemotherapy to this patient.

Figure 13:
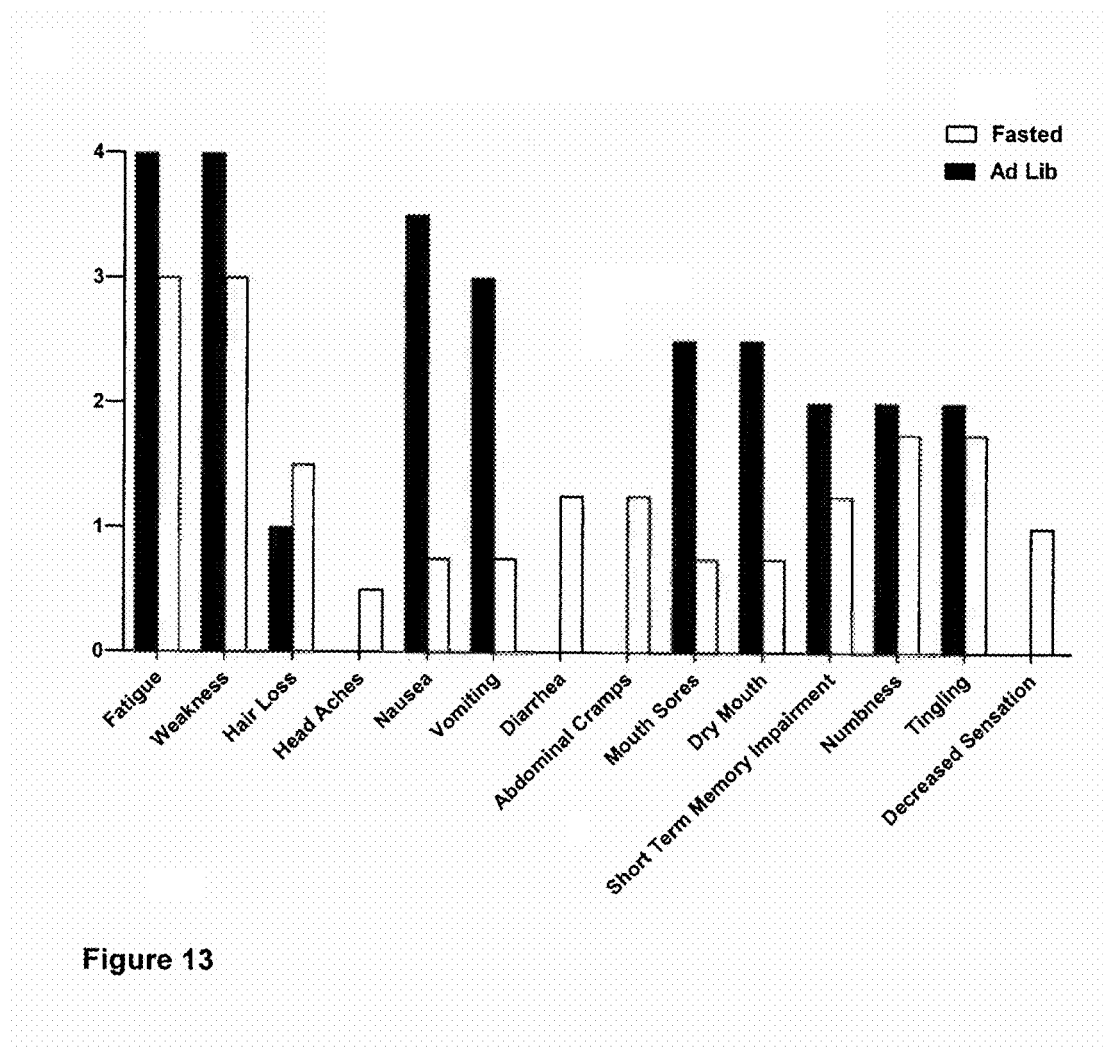
FIG. 13. Self-reported side-effects after chemotherapy for case 2.

Case 2:

A 68-year-old Caucasian male who was diagnosed in February 2008 with esophageal cancer. By the time of diagnosis, metastasis to the left adrenal gland was found on a CT-PET scan, consistent with stage 1V disease. The initial chemotherapy agents were 5-fluorouracil (5-FU) and Cisplatin (CDDP). Concurrently with this chemotherapy regimen, he also received localized radiation for the first two cycles. Throughout this period the patient experienced severe side effects including extreme weakness, remarkable fatigue, diarrhea, vomiting and peripheral neuropathy (FIG. 13). Additionally, the patient complained of intense dysphagia secondary to severe mucositis, most likely caused by the radiation treatment, and consequently underwent a percutaneous endoscopic gastrostomy (PEG) which was removed seven days later. During the third cycle, 5-FU administration had to be withdrawn due to severe nausea and refractory vomiting (FIG. 13). In spite of the aggressive approach with chemotherapy and radiation, his disease progressed. Development of new metastases to the right adrenal gland, lower lobe of the right lung, left sacrum, and coracoid process were shown by a CT-PET performed in August 2008 which prompted augmentation of his chemotherapy regimen ($4^{th}$ cycle), to include carboplatin (CBDCA) in combination with docetaxel and 5-Fu (5 FU was administered for 96 hours). The patient incorporated a 72-hour prior and 51-hour post chemotherapy fasting during the $4^{th}$ cycle. The rationale for the 51 hour post chemotherapy fasting was to protect against the continues administration of 5-FU. The patient lost approximately 7 pounds, 4 of which were regained during the first few days of resuming normal diet. Although three chemotherapeutic agents were used in combination during this cycle, self-reported side effects included only moderate fatigue. Prior to his $5^{th}$ cycle he opted to fast again. Instead of receiving the 5-FU infusion for 96 hours, as he did previously, same dose of 5-FU was administered within 48 hours, and the fasting regimen was also modified to 48 hours prior to and 56 hours post drug administration. Interestingly, there were not only very low self-reported side effects, but also an encouraging clinical response in which the CT-PET scans displayed a decrease in the main esophageal mass, the adrenal glands, and the nodule in the right lower lobe of the lung. For the $6^{th}$, $7^{th}$, $8^{th}$ cycle, where the patient fasted prior to and following chemotherapy treatments (see above), only mild side effects were reported. This was a very aggressive cancer and despite of the well tolerated chemotherapy the patient's disease progressed and the patient deceased in February 2009.

Figure 14A:
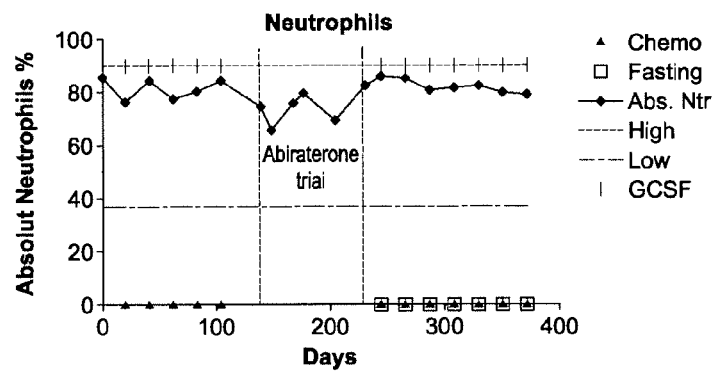
FIG. 14. Laboratory values of blood cell counts for case 3. (A) Neutrophils; (B) Lymphocytes; (C) White blood cells, WBC; (D) Red blood cells, RBC; (E) Platelets; (F) Haemoglobin, Hgb; (G) Haematocrit, Hct; (H) Prostate specific antigen (PSA) level.
Figure 14B:
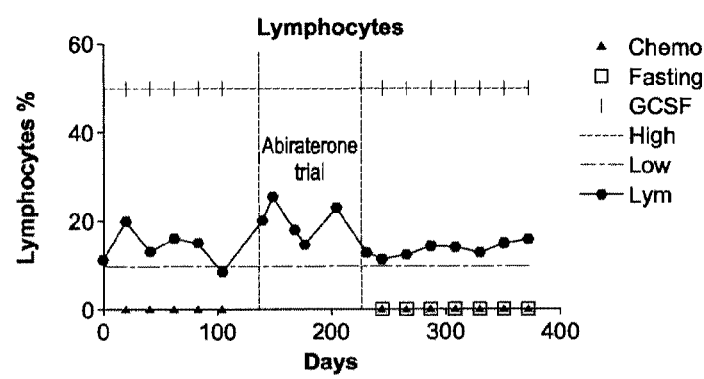
Figure 14C:
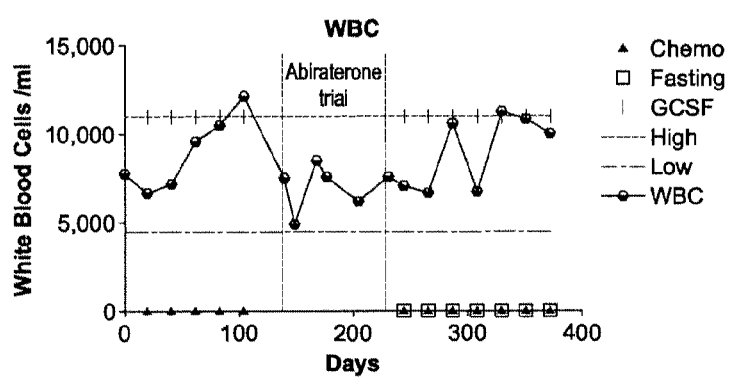
Figure 14D:
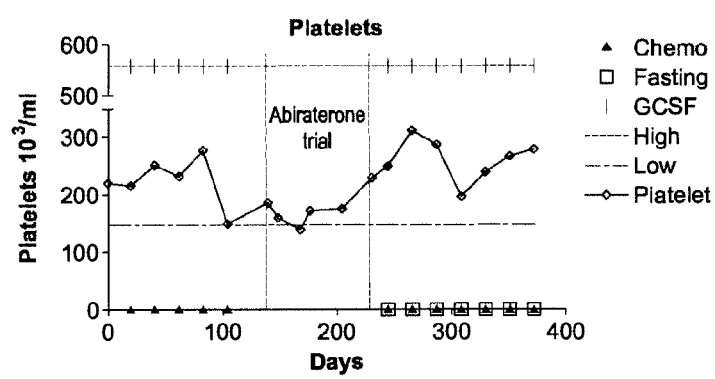
Figure 14E:
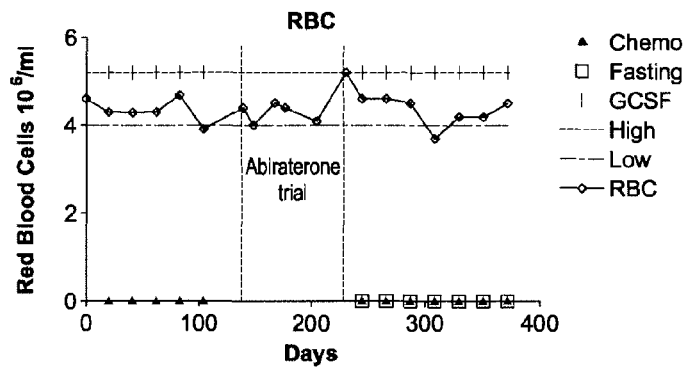
Figure 14F:
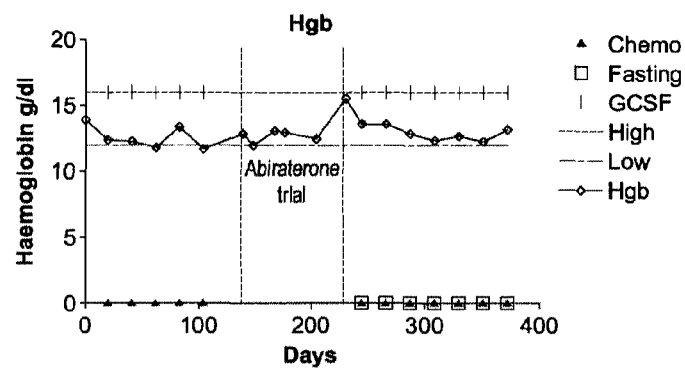
Figure 14G:
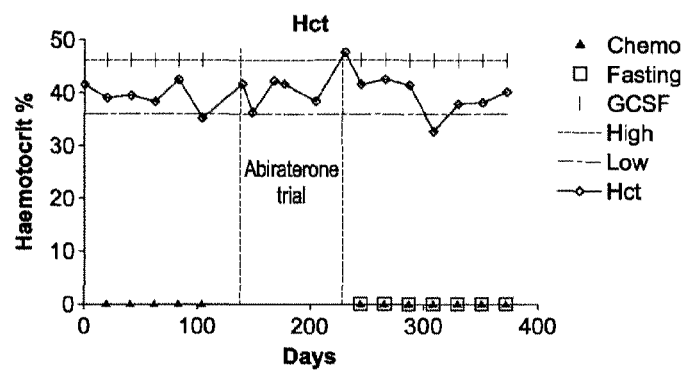
Figure 14H:
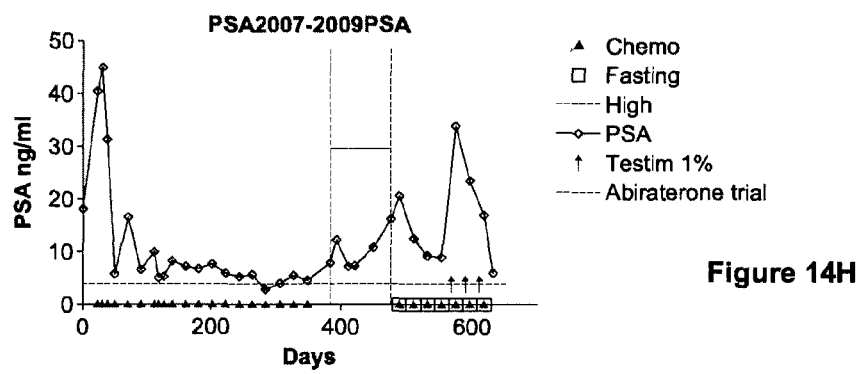
Figure 15:
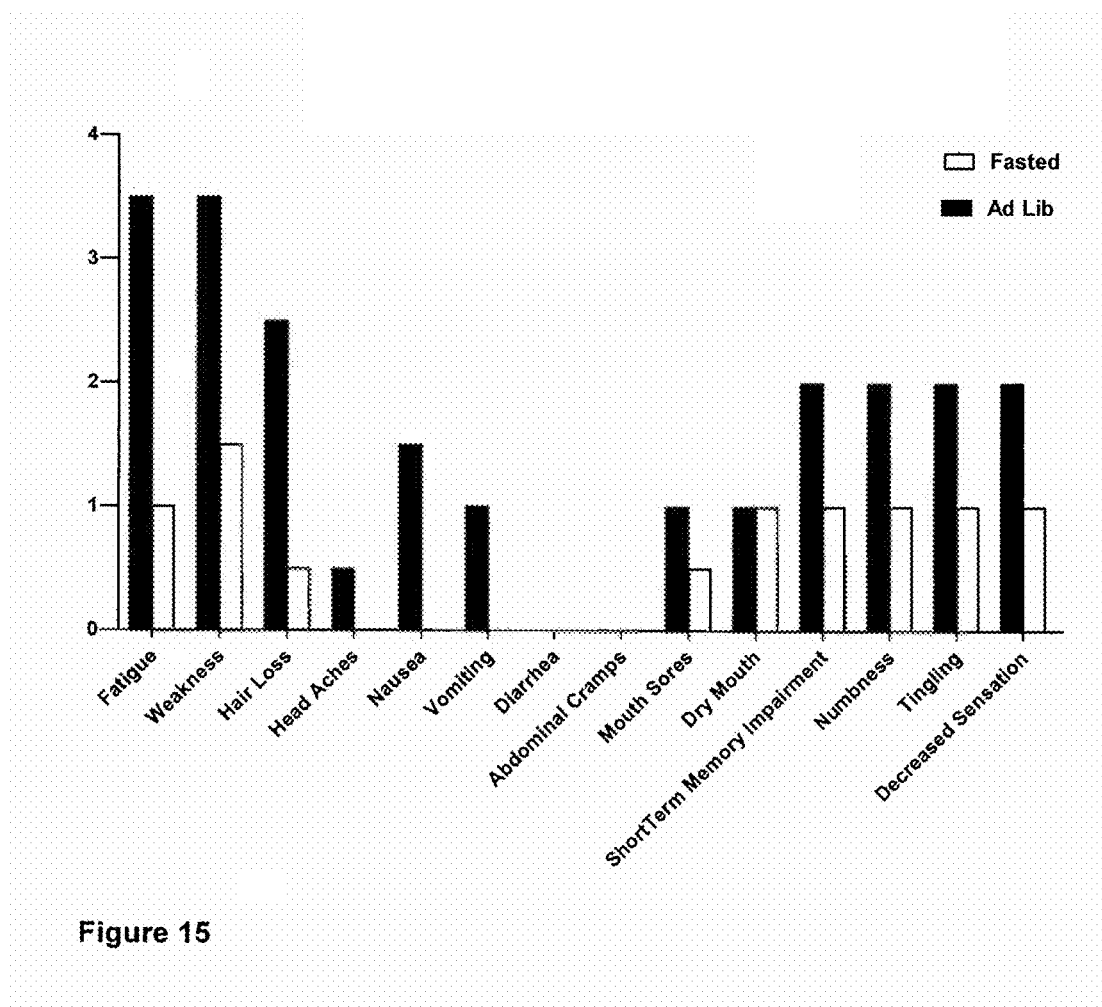
FIG. 15. Self-reported side-effects after chemotherapy for case 3.
Figure 16A:
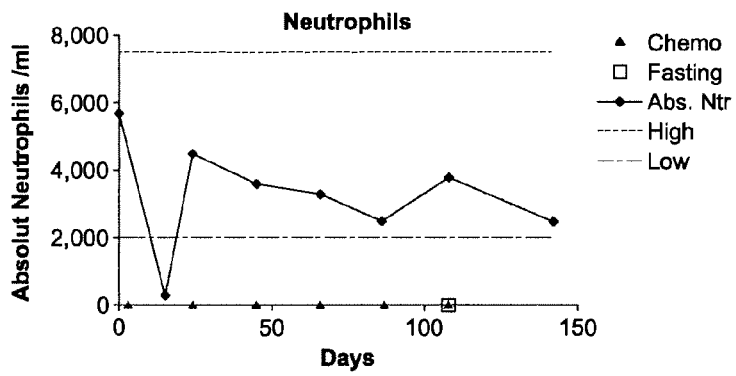
FIG. 16. Laboratory values of blood cell counts for case 4. (A) Neutrophils; (B) Lymphocytes; (C) White blood cells, WBC; (D) Red blood cells, RBC; (E) Platelets; (F) Haemoglobin, Hgb; (G) Haematocrit, Hct.
Figure 16B:
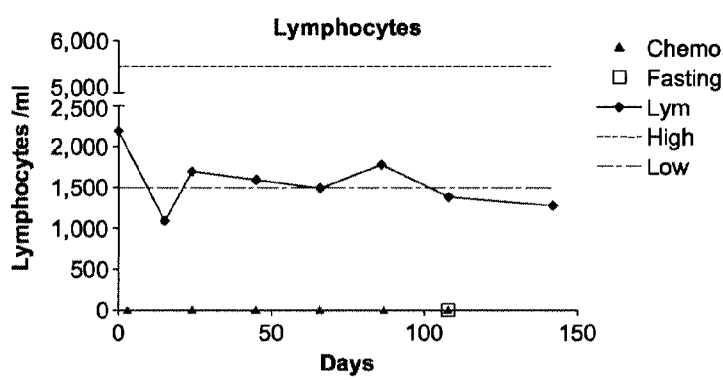
Figure 16C:
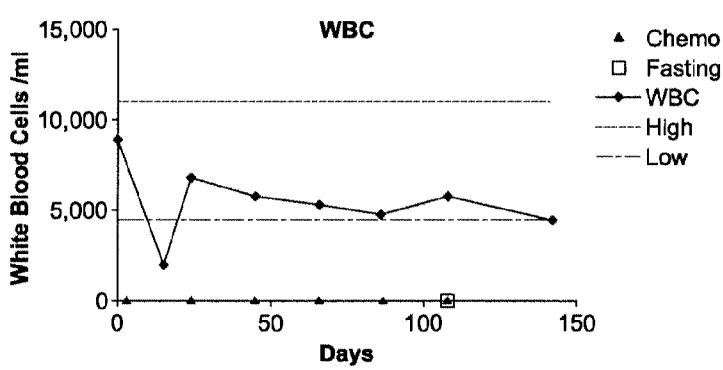
Figure 16D:
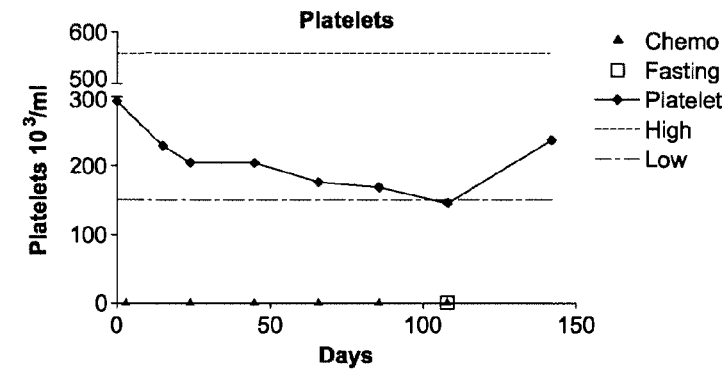
Figure 16E:
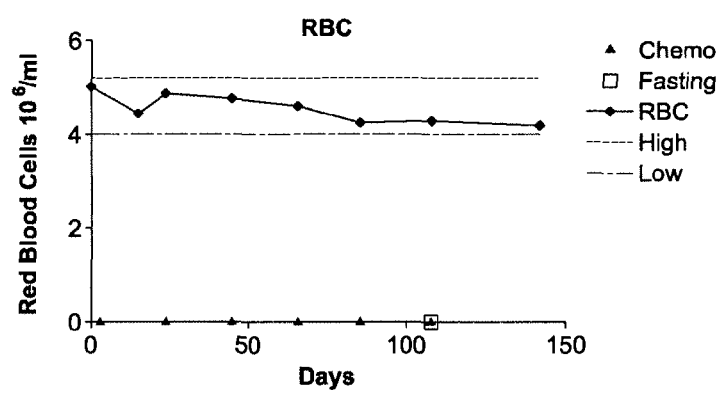
Figure 16F:
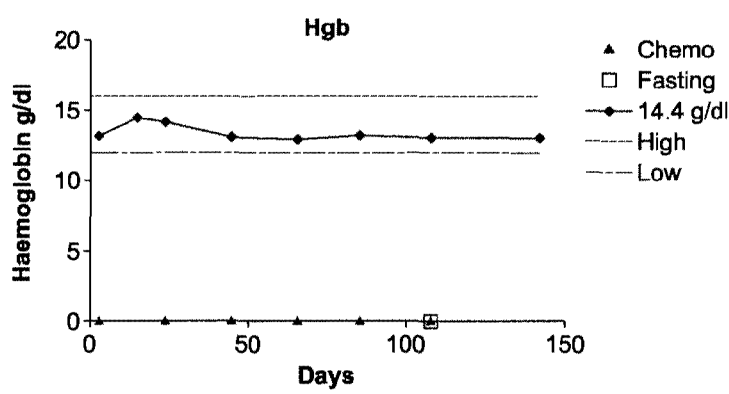
Figure 16G:
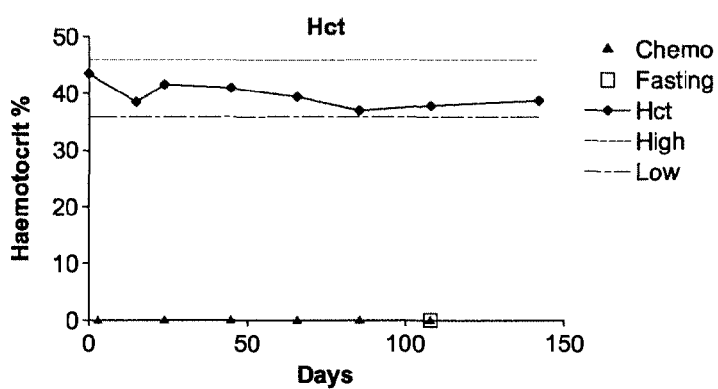

Case 3:

This is a 74-year-old Caucasian man who was diagnosed in July of 2000 with bilateral prostate adenocarcinoma, Gleason score 7 and PSA level of 5.8 ng/ml. A prostatectomy was performed in September of 2000 and PSA level was undetectable until January 2003 when the PSA rose to 1.4 ng/ml. Leuprolide acetate together with bicalutamide and finasteride were prescribed to control the disease. However, administration of these drugs had to be stopped in April 2004 due to severe side effects related to testosterone deprivation. Consequently, different drugs including triptorelin pamoate, nilutamide, thalidomide, cyclophosphamide and ketoconazole were administered to control the disease. However, patient's PSA level reached 9 in January 2007; and new metastases, displayed by bone scan, consistent with stage D2 disease were identified in March 2007. Docetaxel treatment on a weekly basis was initiated in June 2007, but patient's PSA level reached 40.6 ng/ml (FIG. 14H). In August of the same year Avastin was included in the drug regimen. During these cycles the patient experienced significant side effects from chemotherapy including metallic taste, dizziness, forgetfulness, short-term memory impairment and peripheral neuropathy (FIG. 15). Nevertheless, the clinical response was positive and PSA values were normalized (FIG. 14H). In December 2007 a bone scan showed an overall improvement. In 2008, after stopping the chemotherapy treatments, his PSA rose rapidly. Once more, docetaxel was prescribed. From January 2008 to May of the same year, the patient received docetaxel every 21 days. Throughout these cycles he experienced similar side effects as he did previously in 2007, but fatigue and weakness became severe (FIG. 15). In June 2008, Chemotherapy stopped and the patient was enrolled in a phase III clinical trial with Abiraterone, a drug that can selectively block CYP17, a microsomal enzyme that catalyzes a series of reactions critical to nongonadal androgen biosynthesis. During the trial, the patient's PSA levels increased up to 20.9 ng/dl (FIG. 14H). Consequently chemotherapy resumed, but this time, based on studies in fasting and differential stress resistance in animal models (Raffaghello 2008 PNAS), the patient opted to fast prior to chemotherapy. His fasting schedules were 60 hours prior to and 24 post drug administration. The PSA levels dropped promptly upon the renewed fasting/chemotherapies, and notably, the patient reported negligible side effects (FIG. 15). During the last three cycles, besides the fasting the patient applied Testosterone (cream 1%) for five days prior to chemotherapies. The PSA level along with testosterone levels increased dramatically. Nevertheless, 3 cycles of combined chemotherapy with fasting reduced PSA from 34.2 to 6.43 ng/ml (FIG. 14H).

Figure 17:
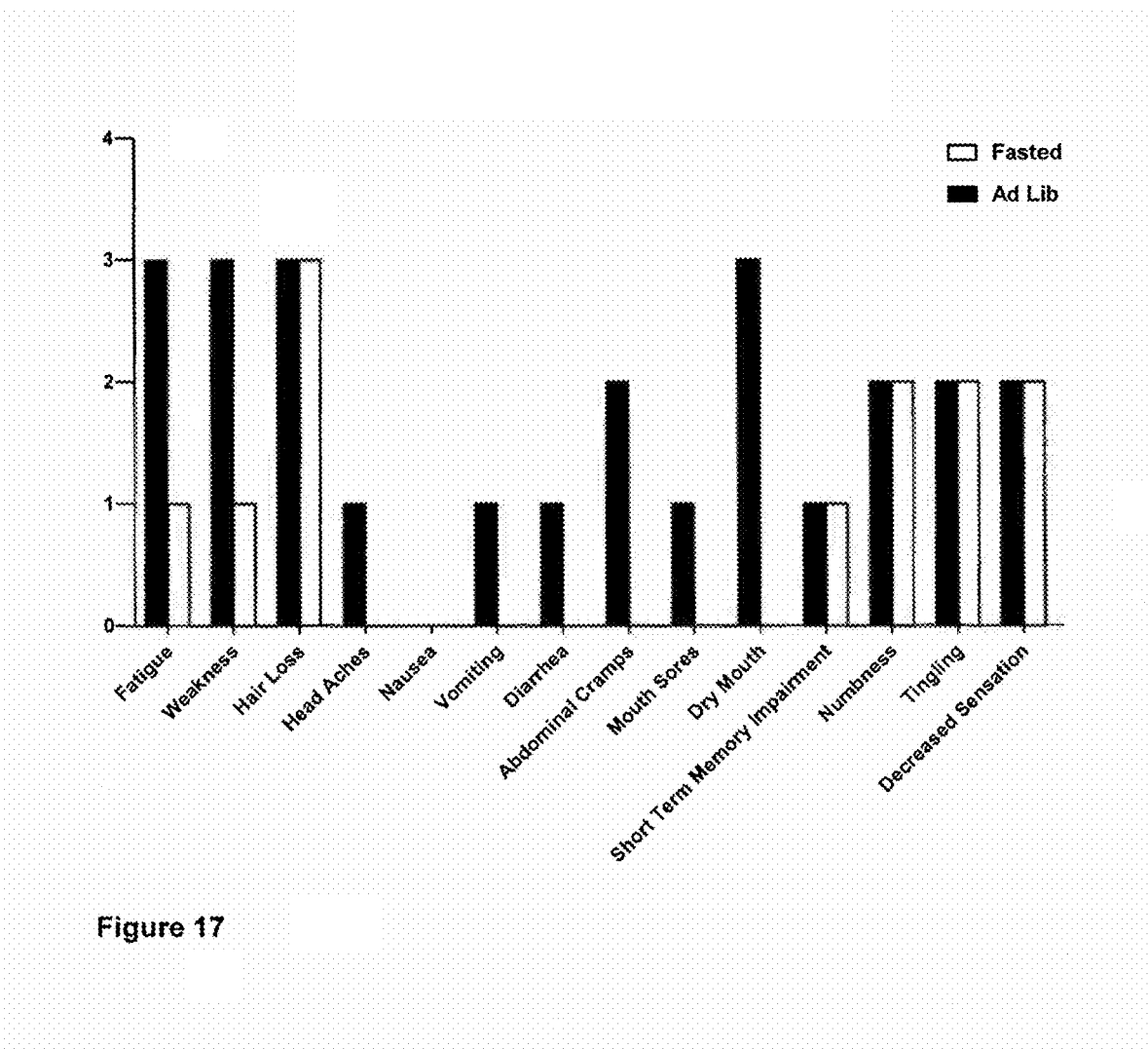
FIG. 17. Self-reported side-effects after chemotherapy for case 4.

Case 4:

A 61-year-old Caucasian female who was diagnosed in June 2008 with poorly differentiated non-small cell carcinoma. The original mass localized in the lower lobe of the left lung proved to be hypermetabolic on a PET scan (June 2008) correlating with the biopsy results. In the same scan, widespread metastatic disease was shown in multiple mediastinal and left perihilar lymph nodes. Metastases to the bones, liver, spleen, and pancreas were also observed. The initial treatment was planned with docetaxel 75 mg/m$^2$ and carboplatin 540 mg/m$^2$. Although she had a regular diet, during the first 5 cycles she lost an average of 4 pounds after each treatment, most likely due to chemotherapy toxicity. The patient reported that it took her approximately three weeks to get back to her original weight. Among the side effects experienced, she complained of severe muscle spasm, lower limb neuropathy, significant fatigue, mouth and tongue sores, easy bruising, bowel discomfort, alternating diarrhea, and constipation (FIG. 17). During the $6^{th}$ cycle which consisted of the same drugs and dosages, the patient fasted for 48-hours-prior and 24-hours-post chemotherapy. During this period the patient lost approximately 6 pounds, which was recovered within 10 days. Besides mild fatigue and constipation which resolved within 2 days, the patient didn't complain of any other side effect that she experienced during the five previous cycles. Furthermore, she reported that after the $6^{th}$ and last cycle, her energy recovered quickly and she was able to walk 3 miles only three days after the drug administration. The last radiologic study performed on February 2009 indicated improvement of the lung lesion (main mass) when compared with its base line PET scan, as well as other organs with positive foci such as the spleen, pancreas and spine.

Figure 18A:
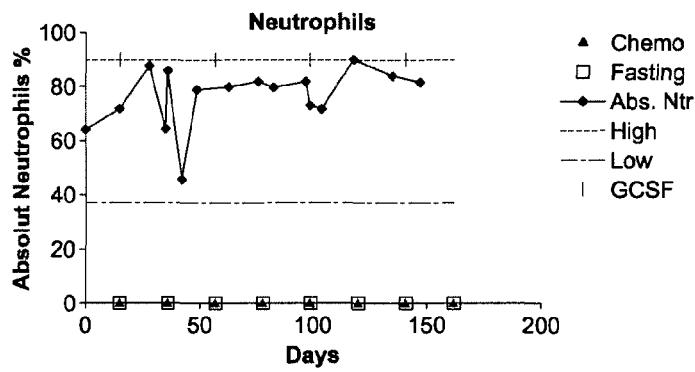
FIG. 18. Laboratory values of blood cell counts for case 5. (A) Neutrophils; (B) Lymphocytes; (C) White blood cells, WBC; (D) Red blood cells, RBC; (E) Platelets; (F) Haemoglobin, Hgb; (G) Haematocrit, Hct; (H) Prostate specific antigen (PSA) level.
Figure 18B:
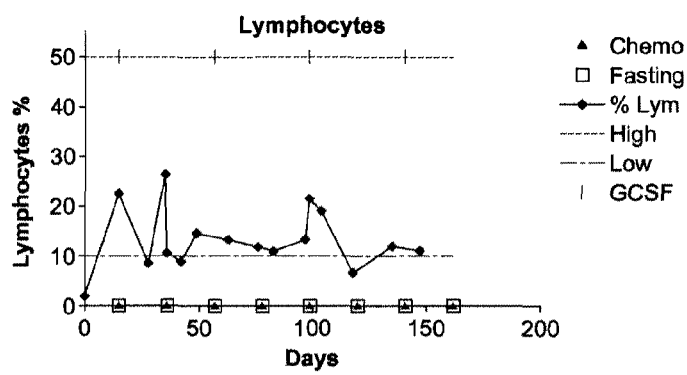
Figure 18C:
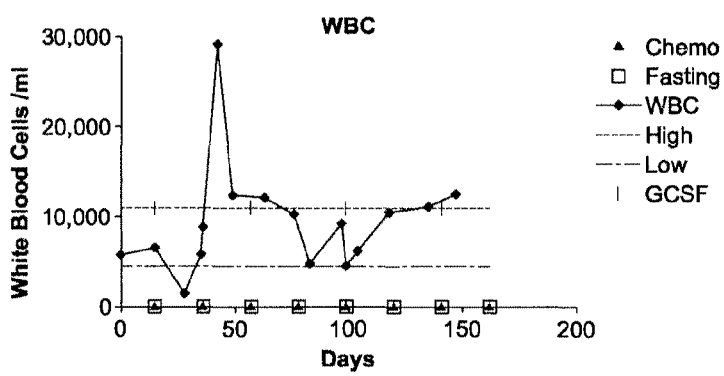
Figure 18D:
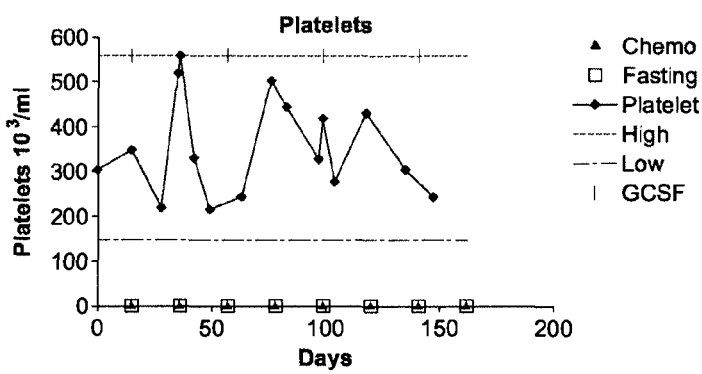
Figure 18E:
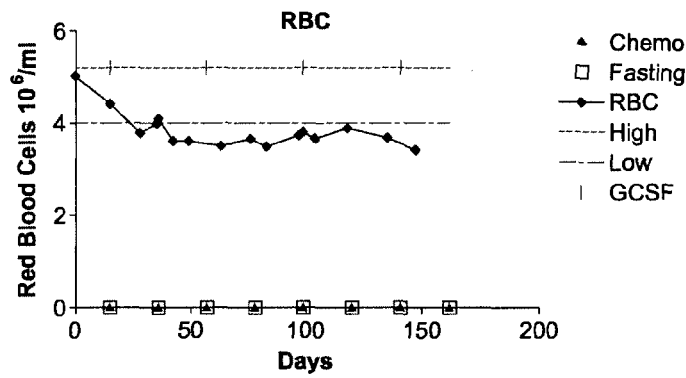
Figure 18F:
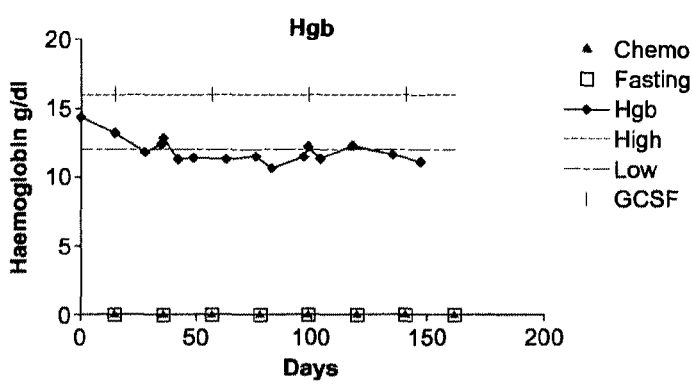
Figure 18G:
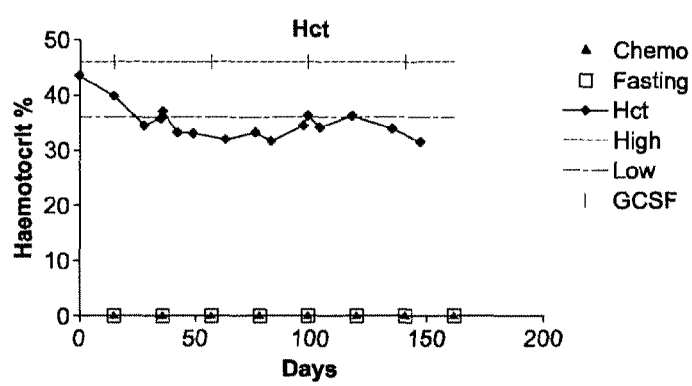
Figure 18H:
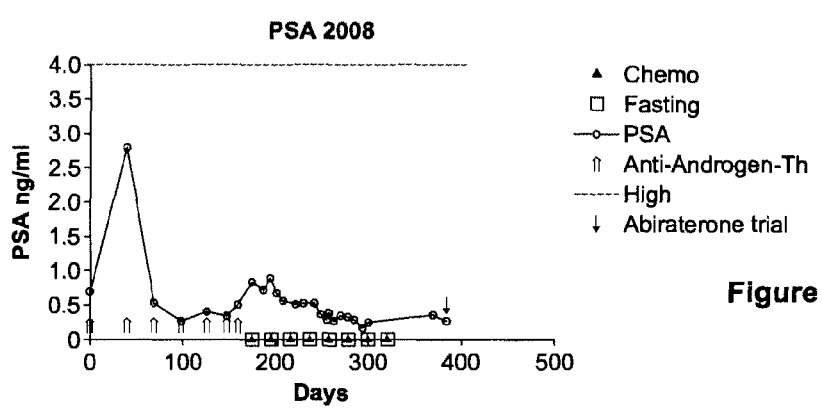

Case 5:

A 66-year-old white man who was diagnosed in July 1998 with prostate adenocarcinoma, Gleason score 8. A positive Prosta Scint study performed in the same year displayed increased uptake of the radiotracer in the right iliac nodes. These findings were consistent with stage D1 disease. During 1998 the patient received leuprolide acetate and bicalutamide for the first time. In September 1999 those drugs wore off and finasteride treatment started. In December 2000, a CT scan insinuated a local progression of the disease. With a baseline PSA of 1.1, he started the second cycle with leuprolide acetate, but this time he also received High Dose Rate (HDR) brachytherapy and external beam radiation with Intensity Modulated Radiation Therapy (IMRT) boost to the right obturator node. This was followed by nandrolone 100 mg a week until 2002. In the following years, different drugs were prescribed such as bicalutamide, triptorelin pamoate and nandrolone were used in order to control the disease. However, his PSA levels increased very quickly each time the treatment was halted. In April 2008, a Combidex scan revealed a 3×5 cm pelvic mass and left hydronephrosis; hence a nephrostomy and a stent were placed to the left ureter. In June of the same year, an increase in the PSA level along with a new CT scan which further confirmed the mass on the left iliac area prompted the treatments with docetaxel ($1^{st}$ cycle, 60 mg/m$^2$, and $2^{nd}$-$8^{th}$ cycle, 75 mg/m$^2$, in a 21-day schedule). Based on animal studies the patient decided to fast 60-66 hours prior to and 8-24 hours post chemo fast (Table A). While fasting, the patient experienced lightheadedness and a significant drop in blood pressure, but the self-reported side effects were almost non-existent except for mild vibratory sensation in the feet developed after seven consecutive cycles of fasting-docetaxel. However, he didn't report numbness, paresthesias, or pain. These results are encouraging considering that most patients develop some type of neuropathy after just two to four cycles with this agent. On the other hand, the blood counts displayed steady values throughout the treatments, except for the first cycle (FIG. 18A), suggesting that blood cells may also benefit from fasting-dependent protection. Lastly, PSA levels throughout the cycles displayed a consistent decrease suggesting that fasting did not block the killing of prostate cancer cells (FIG. 18H).

Figure 19A:
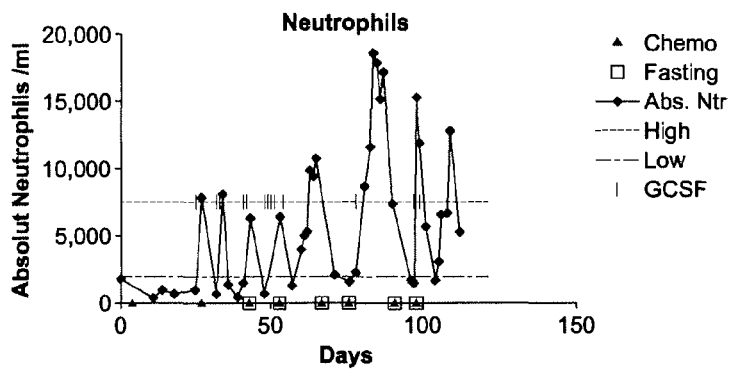
FIG. 19. Laboratory values of blood cell counts for case 6. (A) Neutrophils; (B) Lymphocytes; (C) White blood cells, WBC; (D) Red blood cells, RBC; (E) Platelets; (F) Haemoglobin, Hgb; (G) Haematocrit, Hct.
Figure 19B:
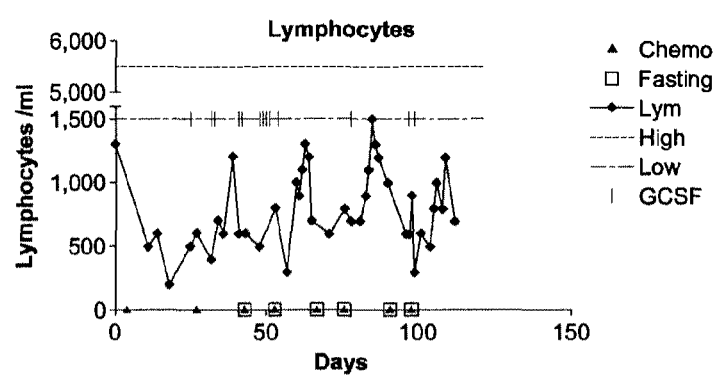
Figure 19C:
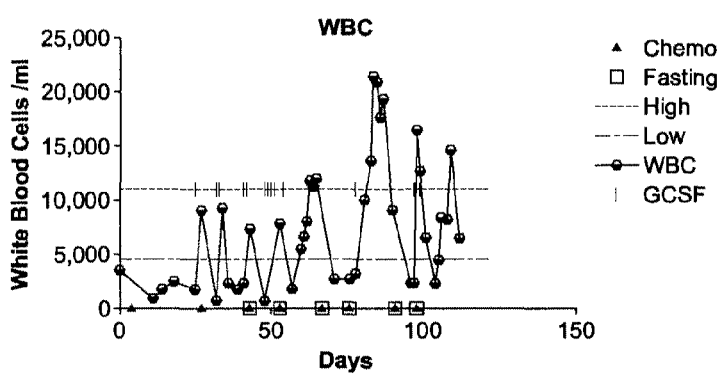
Figure 19D:
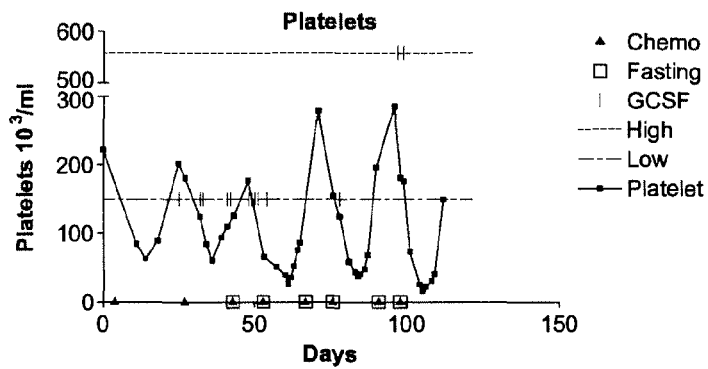
Figure 19E:
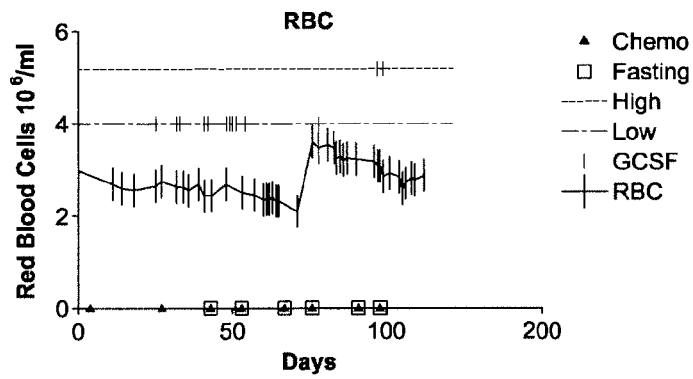
Figure 19F:
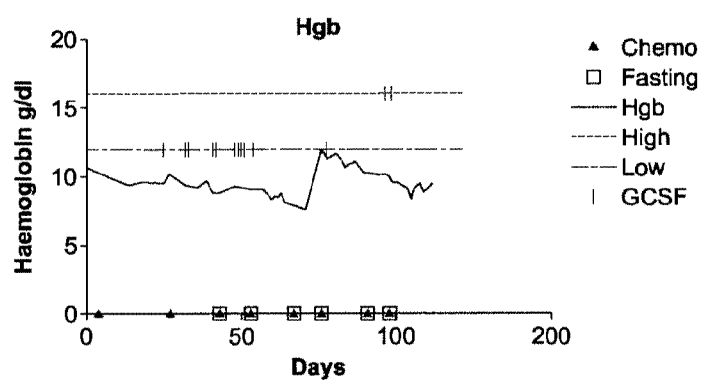
Figure 19G:
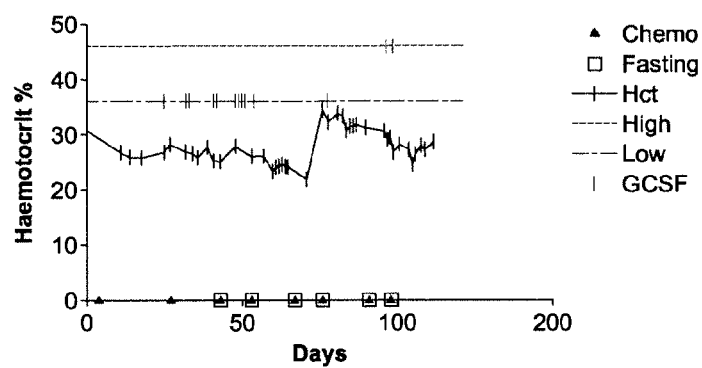
Figure 20A:
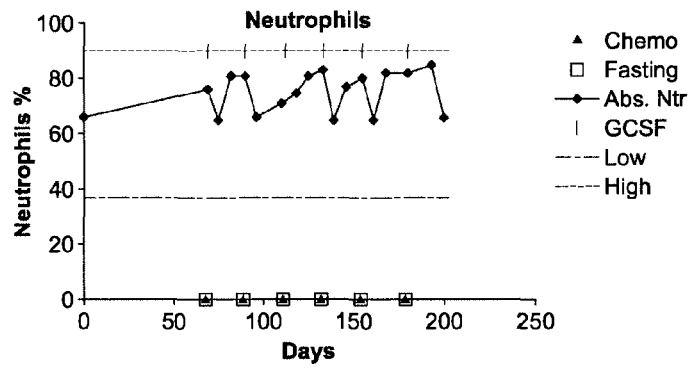
FIG. 20. Laboratory values of blood cell counts for case 9. (A) Neutrophils; (B) Lymphocytes; (C) White blood cells, WBC; (D) Red blood cells, RBC; (E) Platelets; (F) Haemoglobin, Hgb; (G) Haematocrit, Hct.
Figure 20B:
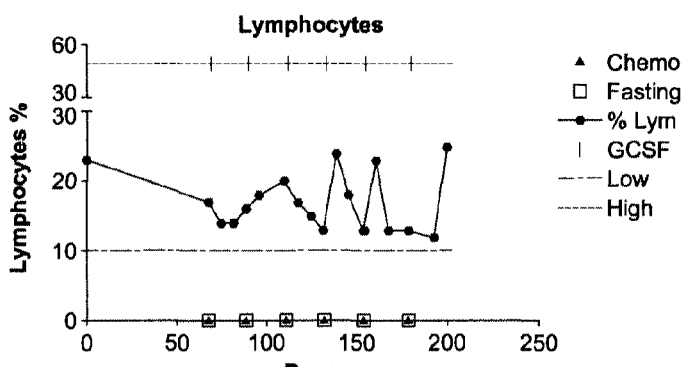
Figure 20C:
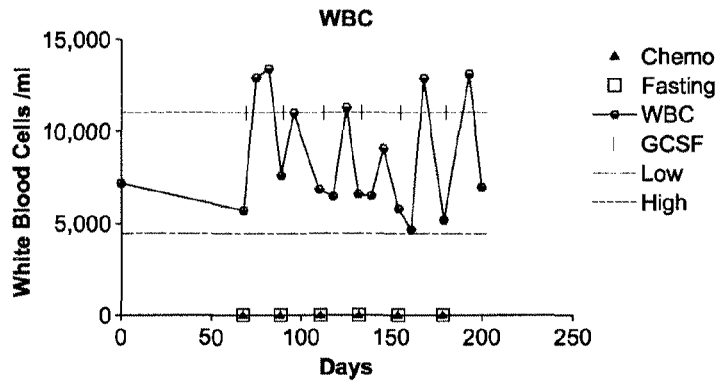
Figure 20D:
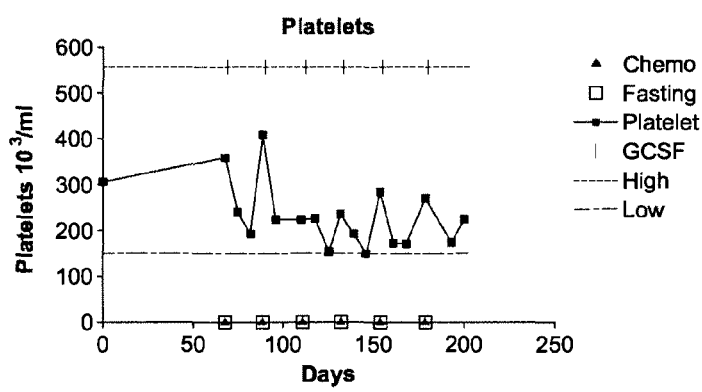
Figure 20E:
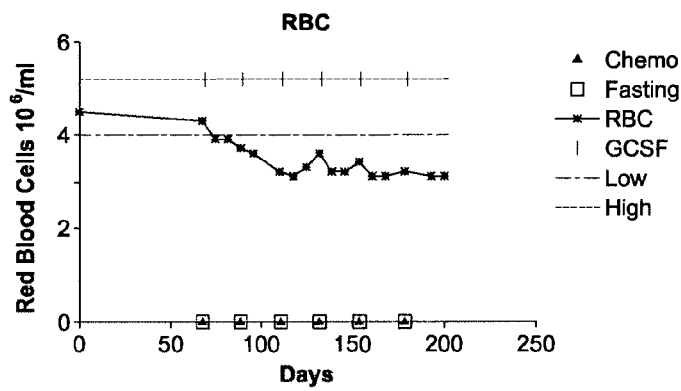
Figure 20F:
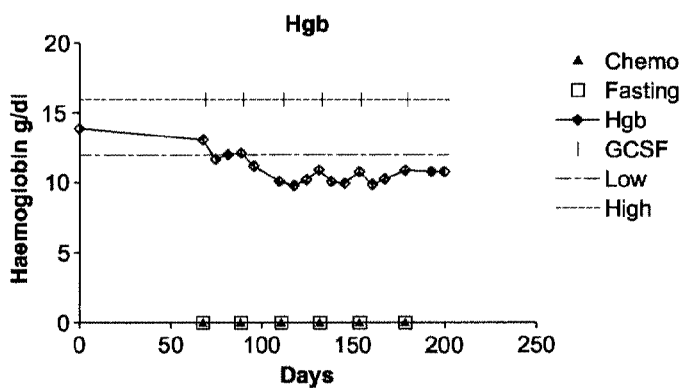
Figure 20G:
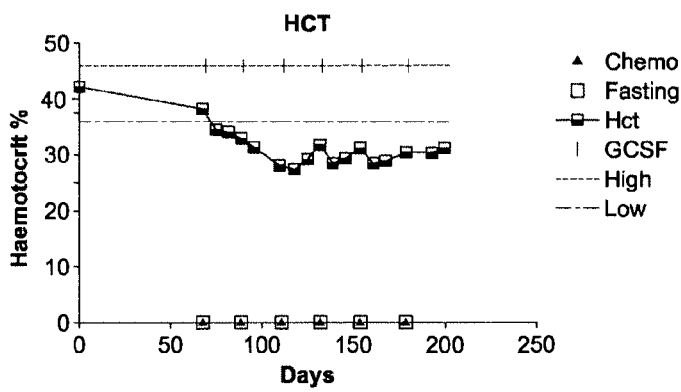

Case 6:

In a 44-year-old white female patient a 10×12 cm right ovarian mass was found in July 2007. Although the patient was subjected to multiple biopsies (30+), they were all negative for cancer and showed no involvement of the ovarian capsule. Based on that, the final diagnosis was Stage IA carcinosarcoma of the ovary. The initial treatment deployed was a six-cycle course with ifosfamide and cisplatin, which the patient received from July to November of 2007. Her first CT scan, performed in January of 2008 didn't show extra ovaric disease. Seven months later, an MRI revealed multiple new pulmonary nodules. This finding was confirmed by a CT scan where more than 20 new nodules were visualized within same area. Also in this study some abnormalities (hypodense images MTS) were found in the splenic region as well as degenerative changes in the spine. Based on these results a new treatment regimen including Taxol, carboplatin and avastin was elected. Infusions started in August 2008 and were performed every three weeks. Concurrently, the patient was supplemented with high dose vitamin C (50 mg/day). In September 2008, a reassessment with a CT scan showed a noticeable decrease in size and number of multiple scattered bilateral pulmonary nodules. By November, however, a CT scan showed that one of the main nodules increased from 0.5 to 0.8 cm, confirming the progression of the disease. A new regimen consisting of gemcitabine on day one followed by gemcitabine and docetaxel on day 8 was prescribed. However after the first administration of gemcitabine at full dose (900 mg/m$^2$), the patient experienced prolonged neutropenia (FIG. 19A) and thrombocytopenia (FIG. 19D) which forced the suspension of the follow up treatment. During the second cycle, the patient received a reduced dose of gemcitabine (720 mg/m$^2$), but again developed prolonged neutropenia and thrombocytopenia, making it difficult to complete the original schedule. Consequently, the patient decided to begin fasting for 62 hours prior and 24 hours post chemotherapy. She reported an overall diminution in side effects and her blood counts improved. We noticed a trend in which nadirs were slightly less pronounced and the peaks were considerably higher in the neutrophil, lymphocyte and leukocyte counts (FIGS. 19A, B, and C, respectively). Additionally, gemcitabine alone led to a rapid and steep decrease in platelet counts, which took 11-12 days to recover. However, the platelet counts did not drop, but rather increased, following the first combined fasting/gemcitabine treatment (FIG. 19D). Platelet nadir did reach a lower level compared to previous chemo-alone treatments, but this time three chemotherapeutic agents were administered instead of one, and the additive effect could be the explanation to these deeper nadirs. Nonetheless the rebound in platelet numbers were much pronounced during the fasting/chemo treatments when compared with chemo-alone (FIGS. 19A, B, and C). This significantly improved and faster recovery of platelets after multiple fasting/chemotherapy cycles suggests that this strategy may have protective effects on megakaryoblasts, allowing a faster repopulation of thrombocytes, neurtphils and lymphocytes.

Case 7:

Here we introduce a 53 years old Caucasian female patient who was diagnosed with stage IIA breast cancer (HER2+). After a Lumpectomy performed in 2008 the patient underwent through 4 cycles with chemotherapy scheduled every three weeks. The regimen combined docetaxel (75 mg/m$^2$) and Cyclophosphamide (600 mg/m$^2$). Throughout 4 cycles the patient fasted 64 hours prior to and 24 hours post the chemotherapy administration. Side effects reported included mild weakness and mild short term memory impairment; no other side effects were reported.

Case 8:

This is a 48 years old Caucasian female patient diagnosed with breast cancer to whom adjuvant chemotherapy was recommended. Her chemotherapy regimen consisted in 4 cycles of doxorubicine (110 mg) combined with cyclophosphamide (1100 mg) every 3 weeks followed by paclitaxel and herceptin on a weekly basis for 12 weeks. Prior to her first chemotherapy treatment (AC) the patient fasted for 48 hour and referred no adverse effects., During the second cycle the patient incorporated 60 hours of fasting prior to the chemotherapy continued by 5 hours post drug administration. Interestingly, she expressed no hardship in following the fasting. Although she experienced hair loss due to chemotherapy, the patient did not suffer other commonly reported side effects from chemotherapy such as fatigue, weakness, nausea, vomiting and diarrhea.

Case 9:

This is a 78 years old lady diagnosed with HER2 positive breast cancer. Upon diagnosis a lumpectomy was performed in which 3 masses were resected from her breast. After the surgery the patient suffered and infection which obliged her to undergo through a second surgery in which a drainage was in placed. Although efforts were made a total mastectomy was unavoidable. 6 cycles of complementary adjuvant chemotherapy with carboplatin (400 mg AUC 6) and docetaxel (75 mg/m$^2$) followed by 6 months with trastuzumab were indicated by the oncologists. Throughout the chemotherapy treatments the patient fasted prior to and after the drug administration. Although variance of fasting regimen adopted by the patient (see Table A), only low fatigue and hair loss were reported. Furthermore total white blood cells counts including neutrophils, lymphocytes, leukocytes and platelets levels were within normal range (FIG. 20). This suggests that fasting could protect the blood cells against the chemotherapy toxicity.

Figure 21:
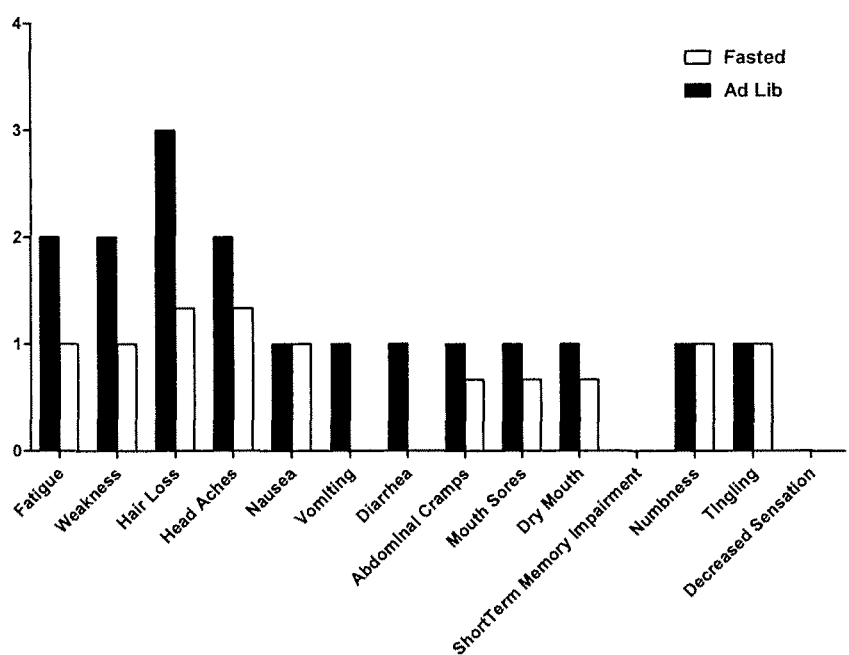
FIG. 21. Self-reported side-effects after chemotherapy for case 10.

Case 10:

This is a 74 years old female patient diagnosed in 2008 with stage 1V uterine papillary serous carcinoma. Consequently surgery and adjuvant chemotherapy were indicated. The surgical procedure consisted of a total abdomino hysterectomy plus bilateral salpingoophorectomy (TAH-BSO). Additionally pelvic, periaortic and precaval lymp node were dissected. Lastly due to a significant enlargement of the right ureter a right nephrectomy was also performed. In addition to that 6 cycles of carboplatin (480 mg) and paclitaxel (280 mg) were applied every 3 weeks. Prior to the first treatment the patient had a regular diet and she experienced fatigue, weakness, hair loss, headaches and also complained of gastrointestinal discomfort (FIG. 21). By contrast before the second cycle and for the rest of the treatments the patient fasted prior to and following the drug administration (see Table A). Although chemotherapy drugs are well known to have cumulative toxic side effects, the patient reported a consistent reduction in most of the side effects previously experienced. This is in agreement with others patient experienced and our preclinical data.

Figure 22A:
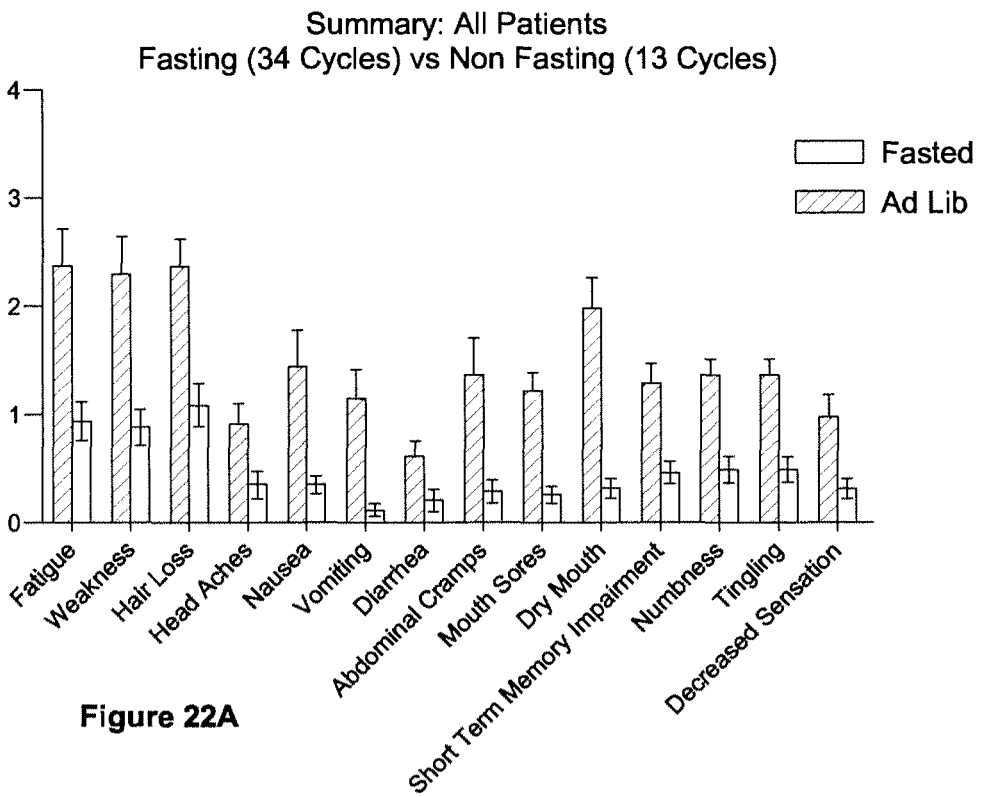
FIG. 22. Self-reported side-effects after chemotherapy with or without fasting. (A) Data represent average of CTC rating post all cycles reported by all the patients in this study; (B) Data represent average of CTC rating from matching fasting and non-fasting cycles.

We obtained self-reported assessments of the severity of the side effect based on the common toxicity criteria scale of all 10 patients monitored, We show the self reported assessment of the side effects for all 10 patients (FIG. 22A). The 5 patients that fasted in combination with all the cycles of chemotherapy reported very low severity for the majority of the side effects. Only mild weakness and hair loss were reported by multiple patients. For the 5 patients that received chemotherapy in association with both fasting or ad lib diet there was a general and major decrease in the self-reported severity of many of the side effects in combination with fasting. Nausea, vomiting, diarrhea, abdominal cramps, and mouth sores were virtually absent from the reports of all 10 patients who fasted whereas at least one of these symptoms were reported by 4 of the 5 ad lib feeding patients.

Figure 22B:
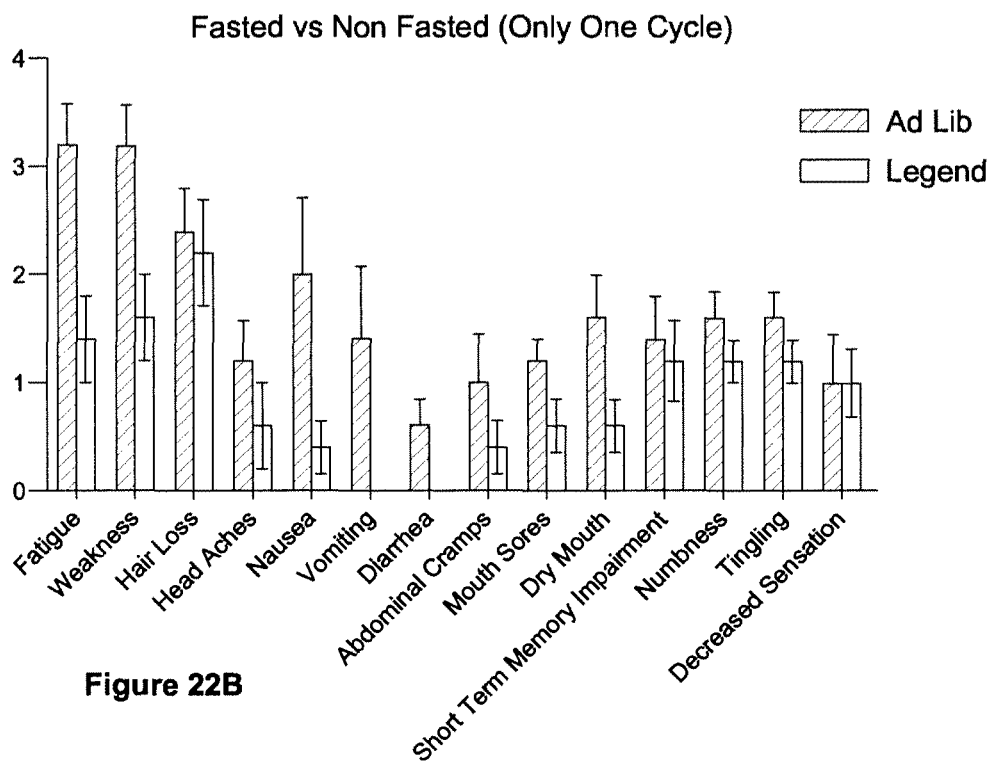

For the five patients who received chemotherapy with or without fasting in at least one cycle we determined the severity of the self-reported side effects by considering only the two closest cycle of chemotherapy in which the patient had fasted or not (FIG. 22B). Whereas symptoms such as fatigue and weakness were significantly reduced ($p<0.001$ and $p<0.00193$, respectively), vomiting and diarrhea were never experienced in combination with fasting (FIG. 22B). Notably, there was no side effect, included in the CTC-based survey, whose average severity was increased by fasting (FIGS. 22A and B).

Since many of the chemo toxic side effects are cumulative, we compared survey data including all the combined fasting- and non-fasting associated chemotherapy side effects. Encouragingly, better self-reported health outcomes were reported by all the patients even though the fasting cycles were mostly carried out in the later portion of the therapy. The survey results, from a small and heterogeneous group of cancer patients, suggest that fasting is safe and well-tolerated in cancer patients and may also ameliorate multiple chemotherapy-dependent side-effects. Although, bias could affect the estimation of the side effects by the patient, the trend of improvements in the post-chemotherapy deficiencies in the counts of multiple blood cell types suggests that fasting may in fact protect against different chemotherapy drugs. Notably, fasting is known to protect organisms ranging from yeast to mice against a variety of toxins and stresses and therefore a protective effect against multiple chemotherapy drugs in humans would not be surprising.

Some of the patients that fasted prior to and following chemotherapy in addition to drinking water consumed a range of very low calorie foods that did not exceed the calorie level or protein level described in this application but continued to experience the protective effects.

Discussion

General dietary recommendations during cancer treatment are based on overall goals to prevent or reverse nutrient deficiencies, to preserve lean body mass, and to minimize nutrition related side effects (such as decreased appetite, nausea, taste changes, or bowel changes) (Doyle, Nutrition and Physical Activity During and After Cancer Treatment, 2006). Contrary to standard post-chemotherapy diets, most patients in this series reported fasting to be feasible and beneficial by reducing side-effects such as fatigue, weakness, nausea, vomiting and abdominal cramps. Minor complaints arose during fasting including dizziness, hunger, or headaches, at a level which did not interfere with normal activities including work.

Weight loss is a major concern in cancer patients. This could be due to cancer itself, reduced appetite following chemotherapy or gastrointestinal damage. Notably in this case report, weight loss during fasting was rapidly recovered by most of the patients, eventually reaching their original weight after completion of their treatments. For the patients who received chemotherapy both with and without fasting, chemotoxic side effects appeared to be attenuated during fasting cycles. Symptoms which appeared to be ameliorated by this intervention were primarily gastrointestinal and constitutional.

In non-malignant cells, environmentally challenging conditions, such as fasting, stimulates the organism to suppress growth/reproduction and divert its energy towards maintenance/repair, and maximize its chance of survival (Longo, Cell review, 2005). Thus, growth factors such as IGF-I decrease and stress resistance mechanisms such as the unfolded proteine response (UPR) increase in response to fasting. Normal cells would respond to these changes, whereas malignant cells would be unresponsive due to self-sufficiency in growth signals, as described in the 6 hallmarks of cancer (Hanahan, Hallmarks of cancer, 2000). Thus, fasting would selectively protect normal cells against chemotherapy toxicity without compromising drug activity on cancer cells.

TABLE A

Additional data from patients who fasted

| | Cycle # | Fast (hours) | Chemotherapy | Tumor Response |
|---|---|---|---|---|
| Case 1 | 1 | 140 pre<br>40 post | Docetaxel 75 mg/m$^2$ +<br>Cyclophosphamide 600 mg/m$^2$ | n/a |
| | 4 | 120 pre<br>24 post | Docetaxel 75 mg/m$^2$ +<br>Cyclophosphamide 600 mg/m$^2$ | n/a |
| Case 2 | 4† | 72 pre<br>51 post | Docetaxel 64.6 mg/m$^2$ + carboplatin<br>485 mg + 5FU 2415.7 mg/m$^2$ | — |
| | 5 | 48 pre<br>56 post | Docetaxel 79 mg/m$^2$ + carboplatin<br>470 mg + 5FU 2415.7 mg/m$^2$ | Stable disease on CT/PET |
| | 6 | 48 pre<br>56 post | Docetaxel 79 mg/m$^2$ + carboplatin<br>470 mg + 5FU 2415.7 mg/m$^2$ | Improvement on CT/PET.<br>Refer to text. |
| | 7 | 48 pre<br>56 post | Docetaxel 79 mg/m$^2$ + carboplatin<br>470 mg + 5FU 2415.7 mg/m$^2$ | — |
| | 8 | 48 pre<br>56 post | Docetaxel 79 mg/m$^2$ + carboplatin<br>470 mg + 5FU 2415.7 mg/m$^2$ | Progression of Disease on CT/PET |
| Case 3 | 7-12‡ | 60-66 pre<br>24 post | Docetaxel 75 mg/m$^2$ | Refer to PSA Graph |
| Case 4 | 6 | 48 pre<br>24 post | Docetaxel 75 mg/m$^2$ + carboplatin 485 mg | — |
| Case 5 | 1 | 65 pre<br>8 post | Docetaxel 75 mg/m$^2$ | Refer to PSA Graph |
| | 2-8 | 65 pre<br>25 post* | Docetaxel 75 mg/m$^2$ | Refer to PSA Graph |

TABLE A-continued

Additional data from patients who fasted

| | Cycle # | Fast (hours) | Chemotherapy | Tumor Response |
|---|---|---|---|---|
| Case 6 | 3 | 62 pre<br>24 post | Gemcitabine 720 mg/m² (day 1) +<br>GMZ 720 mg/m² Docetaxel 80 mg/m2 (Day 8) | — |
| | 4 | 62 pre<br>24 post | Gemcitabine 720 mg/m² (day 1) +<br>GMZ 720 mg/m² Docetaxel 80 mg/m2 (Day 8) | — |
| | 5 | 62 pre<br>24 post | Gemcitabine 900 mg/m² (day 1) +<br>GMZ 900 mg/m² Docetaxel 100 mg/m2 (Day 8) | Reduction in lung masses. Stable bone disease. No new MTS. |
| Case 7 | 1-4 | 64 pre<br>24 post** | Docetaxel 75 mg/m² +<br>Cyclophosphamide 600 mg/m² | n/a |
| Case 8 | 1 | 48 pre | Doxorubicin 110 mg +<br>Cyclophosphamide 1100 mg | n/a |
| Case 9 | 2-4 | 61 pre<br>4 post | Doxorubicin 110 mg +<br>Cyclophosphamide 1100 mg | n/a |
| | 1 | 60 pre | Docetaxel 75 mg/m² + Carboplatin 400 mg | n/a |
| | 2 | 48 pre | Docetaxel 75 mg/m² + carboplatin 400 mg | n/a |
| | 3 | 40 pre<br>24 post | Docetaxel 75 mg/m² + carboplatin 400 mg | n/a |
| | 4 | 48 pre<br>24 post | Docetaxel 75 mg/m² + carboplatin 400 mg | n/a |
| | 5 | 36 pre<br>24 post | Docetaxel 75 mg/m² + carboplatin 400 mg | n/a |
| | 6 | 20 pre<br>20 post | Docetaxel 75 mg/m² + carboplatin 400 mg | n/a |
| Case 10 | 2 | 36 pre | Carboplatin 480 mg + Paclitaxel 280 mg | — |
| | 3-4 | 60 pre | Carboplatin + Paclitaxel | 87% decline in CA 125, Reduction in lymph nodes on CT |
| | 5-6 | 60 pre<br>24 post | Carboplatin 480 mg + Paclitaxel 280 mg | Waiting CT-PET Reports |

‡Cycles 7 to 12 (September 2008-January 2009). All previous cycles performed under regular diet.
*Also utilized low glycemic diet for 24 hours prior to fast.
**Also utilized liquid diet for 24 hours after fast.
†First two cycles were during radiation with 5-FU/cisplatin, and third was 5-FU/cisplatin without fasting.
n/a = not applicable, due to chemotherapy being administered in the adjuvant setting.

EXAMPLE IV

IGF-I Regulates Differential Resistance to Chemotherapy in Normal and Malignant Cells Abstract Chemotherapy toxic side effects including myelosuppression, gastrointestinal damage, and fatigue, limit the dose and length of cancer therapy. Several chemoprotectants have been shown to provide drug-dependent and tissue specific protection, but whether these compounds can have a wide role in differential protection of normal and cancer cells is not known. Recently, we reported that a short-term starvation (STS) selectively protects normal cells and mice but not cancer cells against chemotherapy (differential stress resistance, DSR). Here, we investigated the mechanism of STS-dependent protection. In mice, a 72-hour fast reduced IGF-I by 70% and increased the level of the IGF-I inhibitor IGFBP-1 11-fold. Reduction of IGF-I/IGF-I signaling protected primary glia, but not glioma cells against cyclophosphamide and protected mouse embryonic fibroblasts (MEFs) against doxorubicin-dependent DNA damage. LID mice, which have a 70-80% reduction in circulating IGF-I levels, were protected against 3 out of 4 chemotherapy drugs tested, and 60% of melanoma-bearing LID mice treated with doxorubicin reached long-term survival whereas all control mice died of either cancer metastases or chemotoxicity. These results suggest that IGF-I is a potent inhibitor of protection in normal but not cancer cells.

Introduction

Most chemotherapy agents cause considerable damage to normal cells, leading to toxicity which is dose limiting and has both short- and long-term side effects for patients. Although drug development has reduced these side effects with a succession of selective anti-tumor agents such as antibodies that target specific antigens on cancer [1], or agents with a narrowed therapeutic index [2,3], toxicity continues to limit cancer treatment. Thus, interventions that reduce the undesired toxic side-effects could increase the efficacy of many chemotherapy drugs. Chemoprotectants such as amifostine, glutathione, mesna, and dexrazoxane have been investigated and shown to provide drug-dependent protection to specific tissues, but the use of these compounds has not been shown to increase disease-free or overall survival [4,5]. Recently, we reported that a short-term starvation (STS) provides protection to a broad range of normal cells but not, or much less, to malignant cells, leading to improved survival [6].

Under normal conditions, the finite energy source of an organism is finely balanced between growth and maintenance [7]. However, under challenging environments such as starvation conditions, the energy is diverted from growth to maintenance, thereby enhancing protection and survival at the price of growth [8]. Aging studies in various model organisms show that calorie restriction and deficiencies in the pro-growth GH/IGF-I axis share many physiological characteristics, and are able to increase lifespan as well as stress resistance [9].

Growth hormone (GH) directly regulates the production of IGF-I, which is the major mediator of the growth effects of GH [10]. During starvation, several changes in the GH/IGF-I axis occur as a result of physiological adaptation to the new environment. In humans, IGF-I levels decrease dramatically in response to a short-term starvation (36-72 hours) despite increased GH secretion [11-14]. In mice, a short-term starvation (24-72 hours) decreases both GH and IGF-I production [15,16]. Long-lived organisms that are deficient in IGF-I signaling have also been shown to be resistance to multiple types of stress [17-19]. Our hypothesis is that the reduction of IGF-I in response to starvation suppresses pro-growth pathways in many cells, favoring the investment of energy into maintenance.

Figure 24:
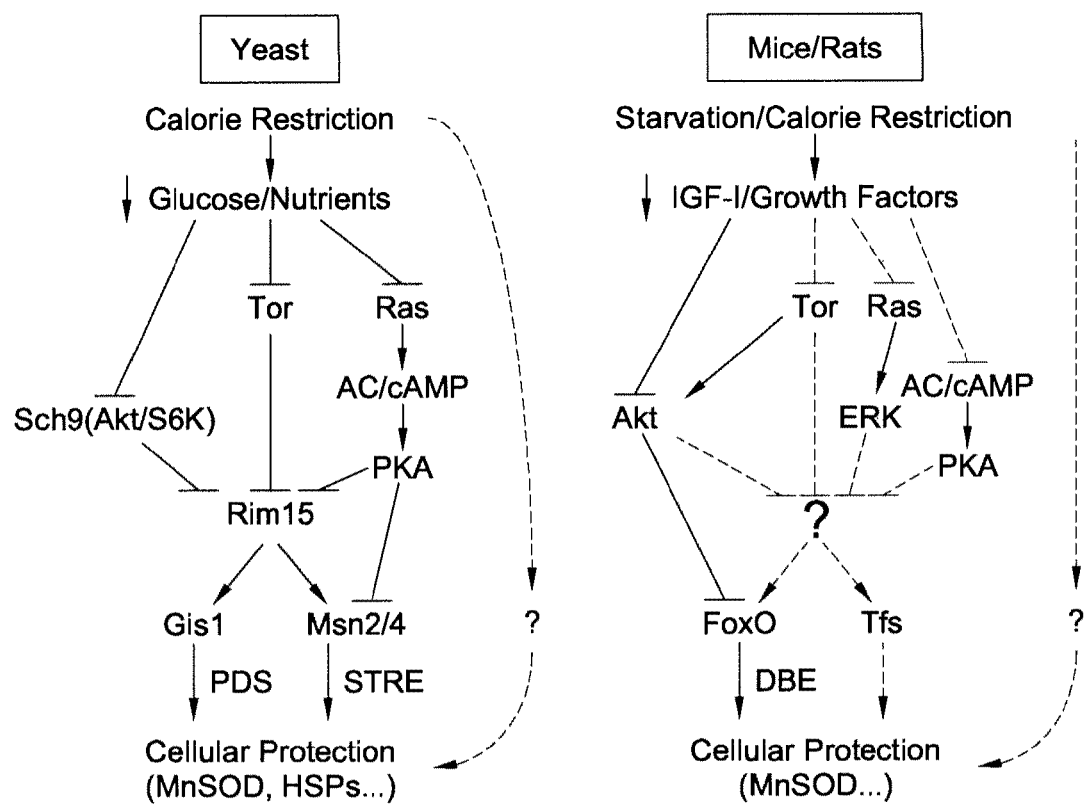
FIG. 24. The conserved regulatory pathways of stress resistance in response to starvation/calorie restriction. In yeast, nutrient-sensing pathways controlled by Sch9, Tor, and Ras converge on the protein kinase Rim15. In turn, the stress response transcription factors Msn2, Msn4, and Gis1 transactivate stress response genes and enhance cellular protection, which leads to life span extension. In mice and humans, a short-term starvation leads to a significant reduction in circulating IGF-I levels. The partially conserved IGF-I signaling pathways negatively regulate the FoxO family transcription factors through Akt. Ras and Tor also function downstream of IGF-I, although their roles in the regulation of stress resistance and aging are poorly understood. Mice deficient in type 5 adenylyl cyclase (AC) are stress resistant, analogous to the adenylate cyclase deficient yeast. Notably, oncogenic mutations that cause the hyperactivation of IGF-I, Akt, Ras, Tor and PKA are among the most common in human cancers [20].

Normal cells and cancer cells differ in many ways but the characteristics that distinguish all cancer cells from most normal cells are very few. Of the many qualifications required for a normal cell to become cancerous, self sufficiency in growth signals and insensitivity to growth inhibitory signals are among the most important, as described in a review of the hallmarks of cancer [20]. Self sufficiency in growth signals is often enabled by gain-of-function mutations in oncogenes (e.g., IGF-IR or the downstream Ras, Akt, mTor, etc) that result in constitutive activation of proliferation pathways regardless of conditions. Notably, the RAS/RAF/MAPK and the PTEN/PI3K/AKT pathways can be down-regulated by CR and starvation [21], possibly by the reduction of IGF-I signaling. On the other hand, insensitivity to growth inhibitory signals is due to loss-of-function mutations in tumor-suppressor genes (e.g., Rb, p53, PTEN, etc), enabling cancer cells to disregard anti-proliferation signals [20,22]. In our studies with *S. cerevisiae*, we have shown that homologs of Ras, Akt and S6K are major mediators of calorie restriction-dependent stress resistance. We have also reported that IGF-I/Ras signaling sensitizes rat neurons to oxidative damage [23] and that homologs of RAS and AKT oncogenes greatly sensitize yeast to various stress challenges and chemotherapy drugs [6,24] (FIG. 24). This distinct response of normal and cancer cells to growth and maintenance regulatory signals is the foundation of our differential stress resistance strategy.

Since fasting would have limited clinical applications due to the inability or unwillingness of patients to undergo prolonged and extreme dietary restriction during therapy, we investigated pathways that may mediate the beneficial effects of fasting on DSR (FIG. 24).

Results

Short-Term Starvation Regulates Components of the Pro-Growth GH/IGF-I Axis

Figure 23:
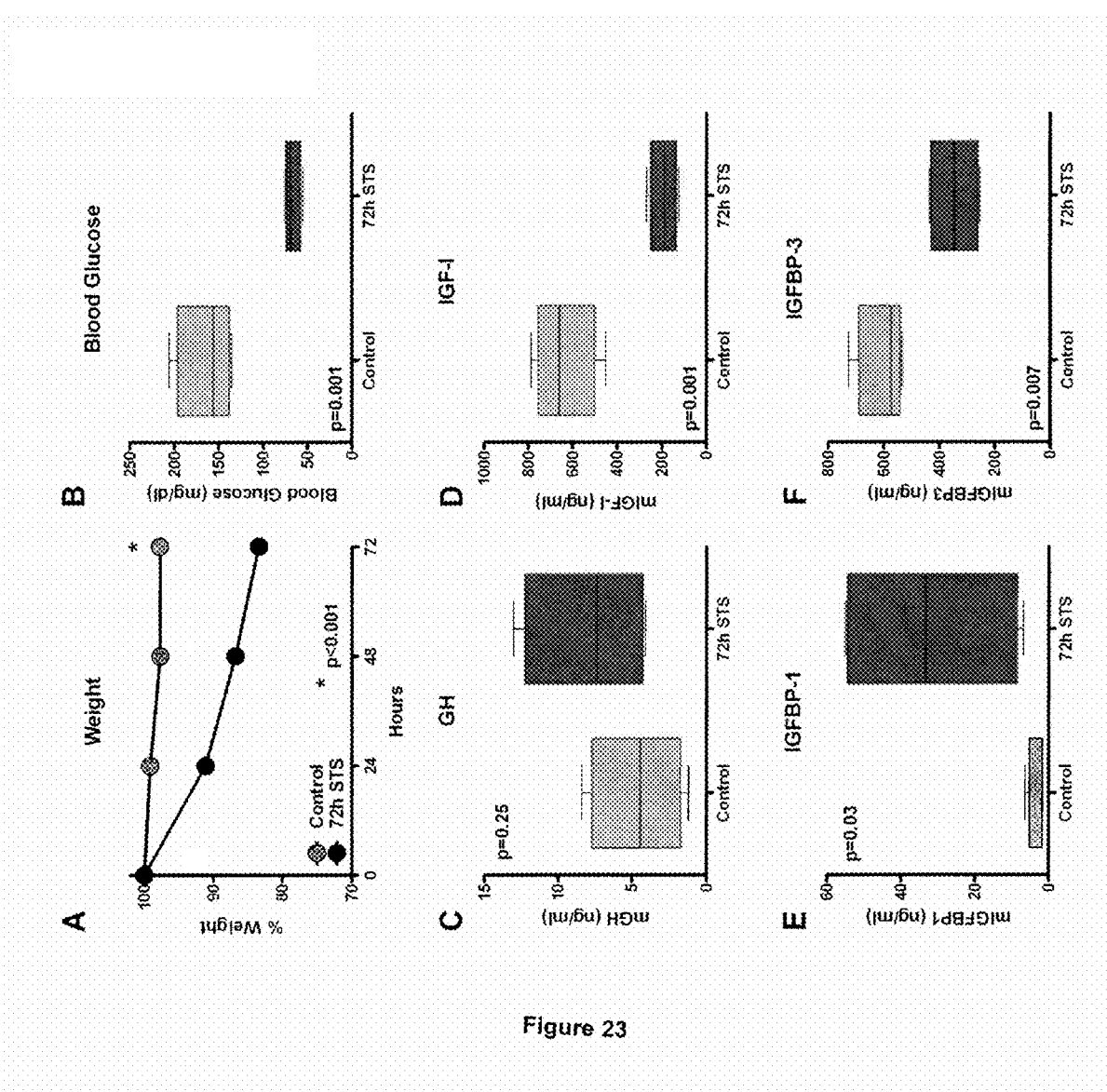
FIG. 23. The effect of 72 hour fasting on weight, glucose levels, and GH/IGF-I axis. 30-week old CD-1 mice were fasted for 72 hours and sacrificed. Blood was collected via cardiac puncture under deep anesthesia, and blood glucose was measured immediately. Plasma was analyzed for GH and IGF-levels (Cohen). GH is a pulsatile hormone and therefore requires a large sample size to obtain significant results. All P values were calculated by Student's t-test except for IGFBP-1 which was done by the Mann-Whitney U test.

To investigate the role of the GH/IGF-I axis in the beneficial effects of fasting on differential stress resistance (DSR), we started by measuring the level of circulating GH, IGF-I and its binding proteins IGFBP-1 and 3 in mice undergoing STS. CD-1 mice were fasted for 72 hours and blood was collected to measure glucose levels and plasma GH, IGF-I, and IGFBP-1 and -3 levels. After a 72 hour STS, mice had lost approximately 20% of body weight, glucose levels were reduced by 41%, GH levels were slightly increased, IGF-I levels decreased 70% (FIGS. 23 A-D). The bioavailability of IGF-I, which can activate IGF-I receptors (IGF-IR), is regulated by IGF binding proteins. In fasted mice, the level of IGFBP-1, which normally reduces IGF-I signaling, increased 11.4-fold (FIG. 23E). These results are in agreement with the reports showing that IGFBP-I increases in response to fasting in humans and rats [16,25,26], and also that its overexpression in mice effectively retards growth by sequestering IGF-I. On the other hand, the 72 hour fast decreased IGFBP-3 levels by 42% (FIG. 23F) in agreement with reports in short-term fasted humans and rats [16,27]. The mechanistic explanation for the decrease in IGFBP-3 is not clear, but it may be due to IGF-I independent effects of IGFBP-3 [28], or increased affinity to IGF-I [27].

Previously, we showed that primary glia but not glioma cell lines pre-incubated with low glucose (50 mg/dl compared to the normal 100 mg/dl) and low serum (1% fetal bovine serum; consequent reduction of several growth factors including IGF-I) showed enhanced protection against the alkylating chemotherapy agent cyclophosphamide [6]. The glucose levels of fasted mice were reduced to a similar level, along with a dramatic decrease in IGF-I levels (FIGS. 23B and D). Thus, the reduction of the major pro-growth factor IGF-I may mediate part of the effect of fasting on DSR (FIGS. 23 D and E; FIG. 24).

Figure 25A:
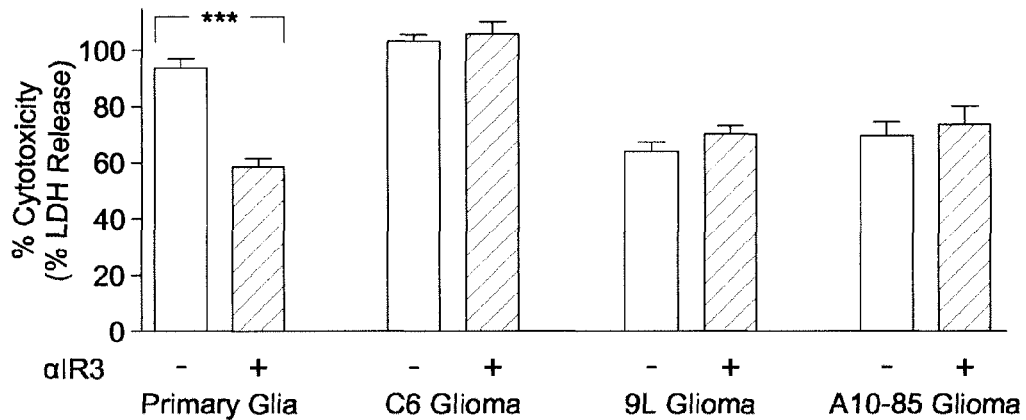
FIG. 25. in vitro DSR to CP treatments by reducing IGF-I. Primary rat glial cells and rat glioma cell lines (C6, 9L, and A10-85) cell lines were tested. (A) Cells were pre-incubated in DMEM/F12 with 1% serum and neutralizing anti-IGF-IR monoclonal antibody alpha-IR3 (1 ug/ml) for 24 hours. Cytotoxicity (LDH assay) was determined following CP treatment (15 mg/ml; n=12) (B) Cells were pre-incubated in medium with either 1% (STS) or 10% FBS for 24 hours. Cytotoxicity (LDH assay) was determined following CP treatment (15 mg/ml; n=12). (C) Cells were pre-incubated in medium with 1% serum with or without rhIGF-I (100 ng/ml) for 48 hours. Cytotoxicity (LDH assay) was determined following CP treatment (12 mg/ml; n=21). *** P<0.0001 by Student's t test.
Figure 25B:
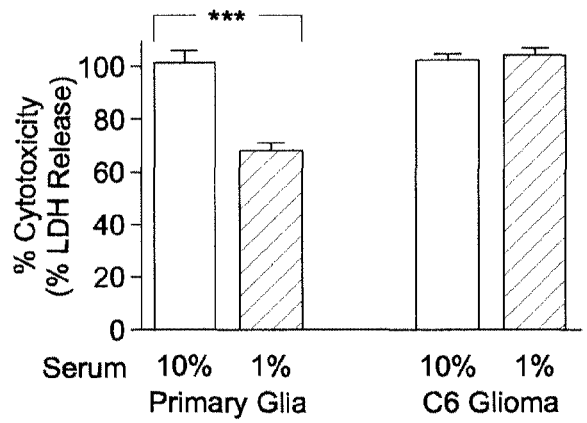
Figure 25C:
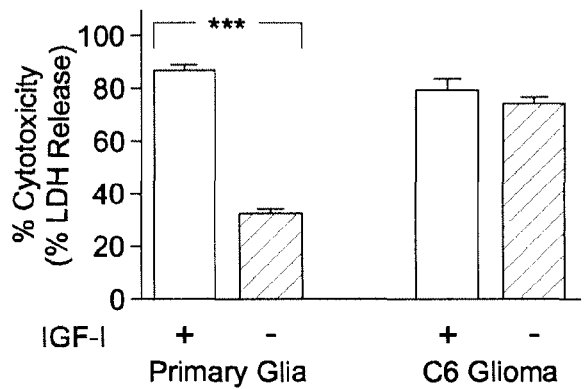

Reduced IGF-I Signaling Protects Primary Glia but not Glioma Cells Against High-Dose Cyclophosphamide IGF-1-like signaling pathways are implicated in regulating life span and stress resistance in organisms ranging from the simple yeast to worms, flies, and mice [9, 29-31]. To test the role of IGF-I signaling in DSR against chemotherapeutic drugs in vitro, we incubated normal and the equivalent cancer cell lines with either an IGF-I receptor (IGF-IR) blocking antibody, different serum concentrations, or excess IGF-I prior to treatment with the alkylating cytotoxic drug cyclophosphamide (CP). Primary mixed rat glia (astrocytes+5-10% microglia) and 3 different rat (C6, A10-85 and 9L) glioma cell lines were tested. All cells were grown to confluence to minimize differences in proliferation rate. First, pre-incubation with an antagonistic IGF-IR antibody (αIR3) protected primary glia but not the three glioma cell lines against CP toxicity (FIG. 25A). Reduction of serum level from the standard 10% to 1%, with consequent reduction of growth factors including IGF-I, decreased the toxicity of 15 mg/ml CP to primary glia but not to C6 glioma cells (FIG. 25B). We also tested the effect of elevated IGF-I on high-dose CP toxicity by adding IGF-I to the culture media. Pre-incubation with 100 ng/ml IGF-I (in the low normal range for adult human serum) [32] caused a 3-fold increase in the toxicity of CP to primary mixed glia but did not increase the toxicity of CP to C6 glioma cells (FIG. 25C). Similar results were obtained with primary neurons and neuron-like pheochromocytoma cells (PC12) treated with a combination of IGF-I and the oxidative stress agent paraquat. These results are consistent with our previous studies on fasting and DSR [6] and support the hypothesis that down-regulation of IGF-I signaling can protect normal but not cancer cells against chemotherapy toxicity.

Effect of IGF-IR Deletion or Overexpression on Stress Resistance in Mouse Embryonic Fibroblast Cells To begin to investigate the mechanism responsible for differential stress resistance, we treated mouse embryonic fibroblasts (MEF) bearing an igf1r deletion (R— cells) or overexpressing IGF-IR (R+ cells) with DXR [33]. All cells were grown to confluence to minimize the difference in proliferation and were treated with DXR for 24 or 48 hours. After a 24 hour DXR treatment, R⁻ cells showed greater survival compared to R+ cells. The effect was most pronounced at 25 μM where more than 80% of R⁻ cells were viable, whereas only 30% of R+ cells were alive (FIG. 26A, P<0.0005). Similar results were observed when cells were treated for 48 hours, with 50% vs. 12% survival rate for R⁻ and R+ cells, respectively, at 25 μM (FIG. 26B, P<0.02).

To begin to investigate how IGF-I protects against chemotoxicity we measured DNA damage using the comet assay. DXR induced DNA damage was significantly higher in R+ cells compared to R− cells, with more than a 3-fold difference as assessed by the comet assay, (FIGS. 26C and D, P<0.001). Notably, R⁻ cells have been shown to be resistant against transformation by the SV40 large T-antigen, which is remarkable considering that fibroblasts frequently transform in culture spontaneously [34]. These results support our hypothesis that the reduced IGF-I signaling protects normal cells by reducing oxidation-dependent DNA damage [35].

The Role of Homologs of Downstream Elements of the IGF-IR in *S. cerevisiae*

Figure 27A:
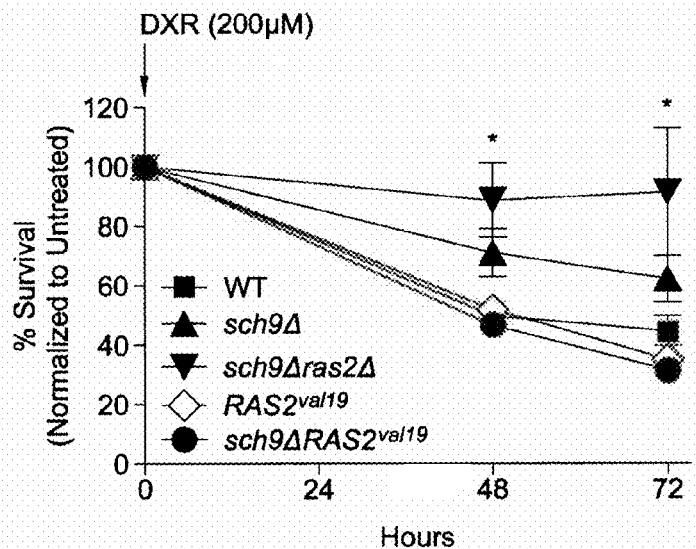
FIG. 27. The effect of Sch9-/Ras2-deficiencies on DSR against DXR in S. cerevisiae. (A) Wild type (DBY746), sch9Δ, sch9Δ, ras2Δ, RAS2$^{val19}$, and sch9ΔRAS2$^{val19}$ strains were inoculated at $OD_{600}$=0.1, grown separately in glucose media, and treated with DXR (200 μM) 24 hours after initial inoculation. Viability was measured as colony forming units (CFU) onto appropriate selective media. Data from 3 independent experiments are shown as mean±SE. * P<0.05 by Student's t test, sch9Δras2Δ vs. sch9ΔRAS2$^{val19}$. (B) Mutation frequency over time, measured as Can$^r$ mutants/$10^6$ cells. Strains shown are wild type (WT), cells lacking Sch9 and/or Ras2, and cells overexpressing constitutively active Ras2$^{val19}$. Data represent the mean±SEM (n=3-5 experiments). Cells were treated with DXR (200 μM) on day 1. Mutation frequency of wild type untreated cells was reported as control. * P<0.05 by Student's t test, sch9Δras2Δ vs. sch9ΔRAS2$^{val19}$.
Figure 27B:
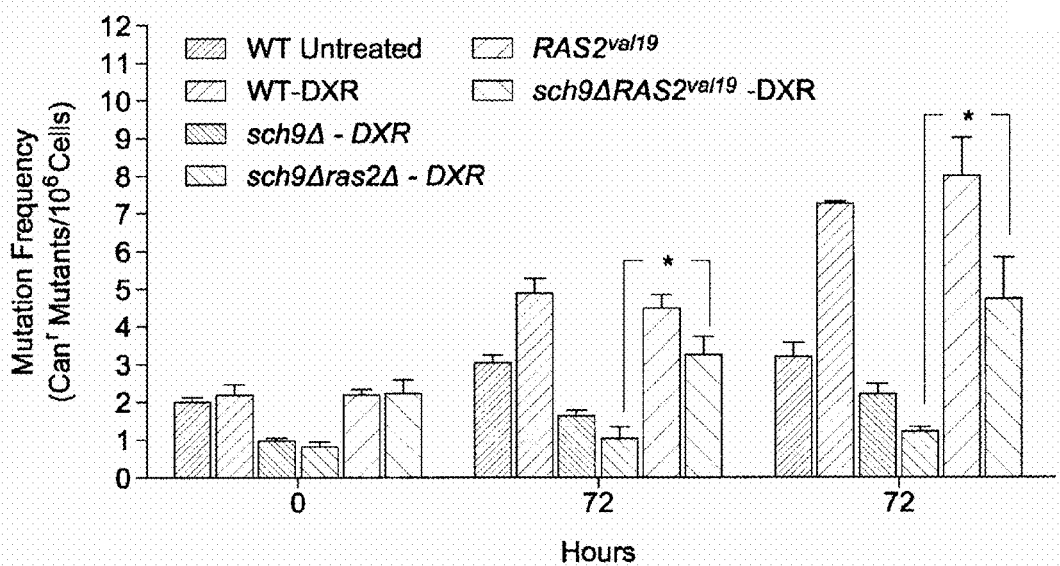

In order to understand the mechanisms by which down-regulation of the IGF-IR protects against chemotoxicity and its effect on DNA damage we turned to the simple model system *S. cerevisiae*. The rationale for utilizing yeast is based on the role of Ras2 and Sch9, homologs of the mammalian Ras and Akt or S6K, respectively, in modulating cellular defense against oxidative stress, DNA alkylation, and thermal stress demonstrated in our previous studies [6,24,36], and on the central signaling role of homologs of SCH9 and RAS2 downstream of IGF-IR. We tested the effect of the deletion of RAS2 and SCH9 on the resistance against DXR. To further investigate DSR, we also studied cells transformed with a gene expressing a constitutively active RAS2 ($RAS2^{val19}$) that models human oncogenic Ras mutations. The deletion of SCH9 (sch9Δ) or SCH9 and RAS2 (sch9Δ ras2Δ) provided remarkable protection against DXR compared to its wild-type (WT) strains (FIG. 27A). However, analogous to our mammalian studies, the expression of the oncogene-like $RAS2^{val19}$ reversed the protection provided by RAS2 and SCH9 deficiency. Following 48 hours of DXR treatment, 50% of WT and $RAS2^{val19}$ expressing cells survived, whereas 70% of sch9Δ and more than 90% of sch9Δ ras2Δ survived (FIG. 27A). The effect was even more pronounced after 72 hours of DXR treatment where sch9Δ ras2Δ and sch9Δ were highly protected (88% and 70% survival respectively) but the protection was reversed by the expression of $RAS2^{val19}$ (sch9Δ $RAS2^{val19}$; 27% survival). To begin to investigate the molecular mechanisms of differential resistance to DXR, we monitored DNA mutation frequency, measured as Can$^r$ colonies/$10^6$ cells [37]. DXR treatments increased mutation frequency in all strains. In agreement with the survival analysis, sch9Δ and sch9Δ ras2Δ exhibited the lowest mutation frequency, whereas $RAS2^{val19}$ expression increased mutation frequency (FIG. 27B). The expression of $RAS2^{val19}$ in sch9Δ (sch9Δ $RAS2^{val19}$) completely reversed the protection provided by the Sch9 deficiency resulting in a 3-fold increase in mutation frequency (FIG. 27). These data suggest that the beneficial effects of lowered Ras2 and Sch9 signaling are due to, at least in part, the enhanced protection against DNA damage in the cell and can be reversed by the expression of oncogenes.

Octreotide Sensitizes NXS2 Neuroblastoma Cells But does not Protect Mice Against High-Dose Etoposide Since reduction of IGF-I provided differential chemotherapy protection in mammalian cell culture, we tested if pharmacological manipulation of the GH/IGF-I axis could induce DSR in vivo. The somatostatin analogue octreotide is used in clinics to reduce GH secretion and IGF-I production primarily in acromegaly patients. Also, octreotide was selected because somatostatin increases in response to fasting [38]. In a previous report, we showed that a short-term starvation (STS) provides DSR against high-dose etoposide, a widely used chemotherapy drug that inhibits topoisomerase II [6]. Here we tested if the protection against etoposide could be obtained or augmented by inhibiting the GH/IGF-I axis with octreotide. Interestingly, octreotide and other somatostatin analogs have been shown to have therapeutic effects in a number of cancers [39] through two distinct effects: direct actions on tumors mediated by somatostatin receptors [40, 41], and indirect effects through inhibition of growth hormone release and the lowering of IGF-I [40-42]. We selected a particularly aggressive tumor line (NXS2) that models neuroblastoma (NB) [43]. Intravenous injection of NXS2 cells results in a consistent formation of metastasis in multiple organs including the liver, kidneys, adrenal gland, and ovaries [43]. A single injection of high-dose etoposide (80 mg/kg) extended the lifespan of tumor-bearing mice, which otherwise would have succumbed to metastasis within 40 days. In our previous study, STS caused a remarkable reduction in acute chemotoxicity-related deaths, but also provided partial protection to the cancer cells [6]. Our present results indicate that octreotide is not sufficient to protect the animals against chemotherapy but its combination with STS sensitizes the NXS2 cancer cells to etoposide. However, octreotide, which is primarily used to reduce GH production in humans, had a minor effect on lowering IGF-I levels in mice, thus the lack of host protection by octreotide may be explained by its minor effect on IGF-I level. It is possible that homeostatic mechanisms counteract the effect of somatostatin and lead to tachyphylaxis to octreotide treatment, thus failing to reduce IGF-I levels significantly.

To test if octreotide exerted its sensitizing effect on NXS2 cells directly or indirectly, we treated NXS2 cells with octreotide and etoposide in vitro. Octreotide did not alter the toxicity of etoposide to NXS2 cells in cell culture, suggesting the sensitizing effect of octreotide in mice is indirect. Together, this implies that octreotide alone does not provide starvation-like host protection, but may reverse the partial protection provided by STS to cancer cells by sensitizing them. Further studies are necessary to investigate the possibility that octreotide may sensitize other tumors against chemotherapy.

Enhanced Stress Resistance in LID Mice Against High-Dose Chemotherapy

Mice with genetic disruptions in the IGF-IR or its downstream elements have been shown to be more resistant against oxidative stress [17,44]. To determine whether reducing IGF-I signaling protects against chemotoxicity, we tested a transgenic mouse model with a conditional liver igf1 gene deletion (LID), using an albumin driven Cre/loxP recombinant system [45] which results in a post-natal 70-80% reduction of circulating IGF-I [46], which is similar to that of 72 hour fasted mice (FIG. 23D). The LID mice provides a model for investigating the mechanistic relationship between IGF-I and fasting in chemotherapy resistance [47]. First, based on our promising results with etoposide and STS/octreotide, we challenged LID mice with high-dose etoposide. Surprisingly, LID mice were not protected compared to the controls (mice homozygous for loxP-flanked igf1 gene but lacking the cre-recombinase) [45] to a single administration of 100 mg/kg etoposide, with 50% vs. 88% survival rate respectively in the LID and control mice (FIG. 28A, n=10/LID, n=9/control, P=0.064). Then, based on our in vitro results, we tested CP in LID mice. LID mice treated with 500 mg/kg CP showed significantly higher resistance, with 70% vs. 30% survival rate for LID and control mice respectively (FIG. 28B, n=20/group, P=0.001). Furthermore, while LID mice only lost an average of 10% of their weight, control mice lost 20%. The surviving LID mice also did not show any signs of toxicity. To determine the range of protection by reduced IGF-I, we tested two additional drugs, 5-fluorouracil (5-FU) and doxorubicin (DXR), which represent different classes of chemotherapy drugs. Cyclophosphamide is a DNA alkylating agent [48], 5-FU is an antimetabolite[49], DXR is an intercalating agent and topoisomerase II inhibitor [50,51], and etoposide is a topoisomerase II inhibitor[52]. Survival after a treatment with high-dose 5-FU was improved, with a 55% vs. 10% survival rate in LID and controls respectively, although the difference was not significant (FIG. 28C, n=11/LID, n=10/control, P=0.148). Similar but more pronounced effects were obtained with DXR. Unlike etoposide and other drugs that can cause irreversible damage to the tail vein of rodents after a single high-dose injection, DXR can be injected for up to 2-3 cycles. Thus, in order to test the effect of multiple cycles of chemotherapy, we challenged LID mice with 2 cycles of high-dose DXR. The first DXR injection (20 mg/kg) did not result in any toxicity related deaths, but led to considerable weight loss in all mice (FIG. 28D). Weight loss was more evident in LID mice during the first 5 days following DXR injection, but unlike controls who continued to lose weight and showed signs of toxicity, LID mice regained their weight during the following 3 weeks. The second DXR injection (28 mg/kg) caused a considerable amount of DXR-related deaths in the control (25% survival) but not in the LID mice (100% survival) (FIG. 28D, n=5/LID, n=4/control, P=0.022).

Figure 29A:
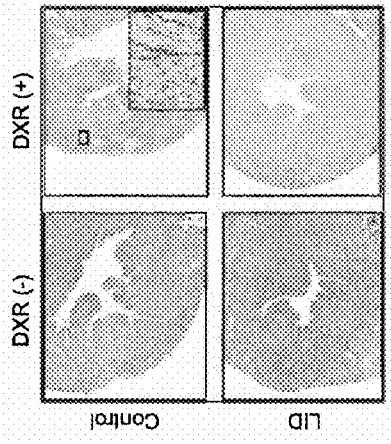
FIG. 29. Differential stress resistance (DSR) against 2 cycles of high-dose DXR in melanoma bearing LID mice. (A) Timeline of experimental procedures. (B) Bioluminesence imaging of B16Fluc melanoma bearing LID mice and control mice treated with 2 cycles of high-dose DXR. Five mice were randomly selected and followed throughout the experiment to monitor tumor progression or regression. (C) Survival rate comparison between B16Fluc melanoma bearing LID and control mice treated with 2 cycles of high-dose DXR (P<0.05). (D) The data in (C) represent all deaths resulting from both metastasis and DXR toxicity. Therefore, the data was analyzed to represent only DXR toxicity related deaths. (F) Weight of LID and control mice. (F) DXR induced cardiomyopathy in control and LID mice. Heart failure is a major outcome of acute DXR toxicity [76]. Histological slides of the heart from DXR treated control mice showed loss of myofibrils and infiltration of immune cells, whereas DXR dependent cardiac myopathy was not observed in LID mice. Hematoxylin and eosin staining. Representative slide shown. Bar, 100 µm.
Figure 29B:
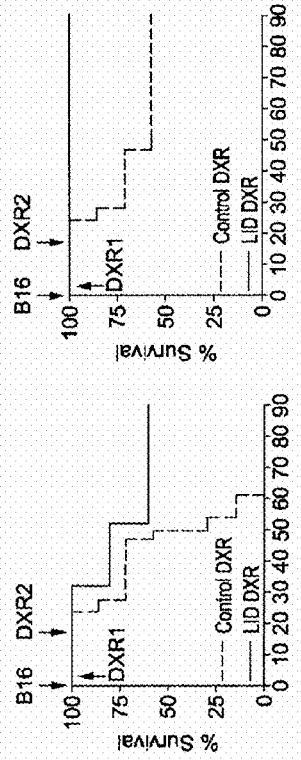
Figure 29C:
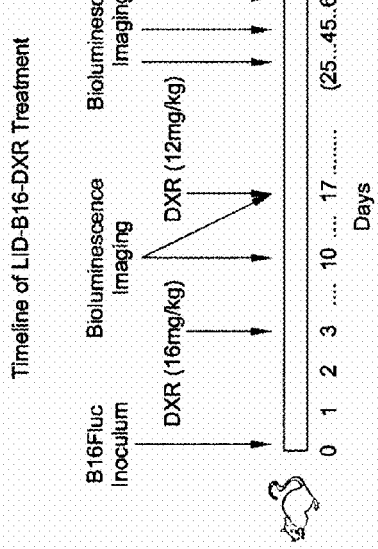
Figure 29D:
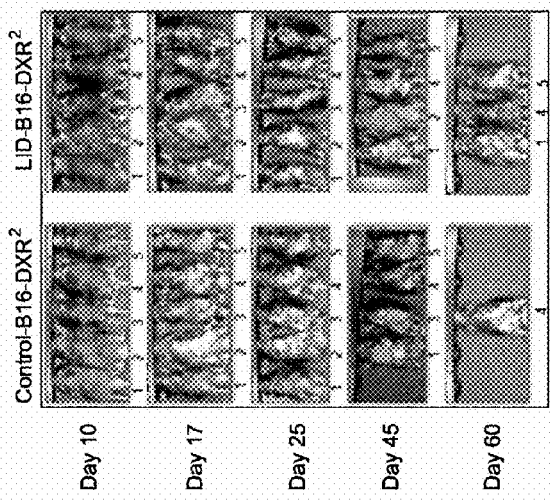
Figure 29E:
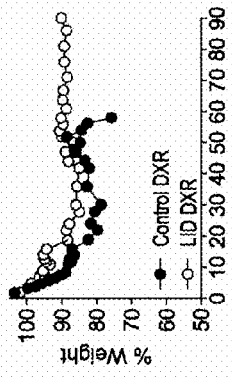
Figure 29F:
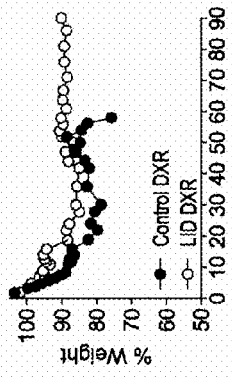

Differential Stress Resistance in Melanoma Bearing LID Mice Against High-Dose Doxorubicin Next, we tested DSR in vivo by monitoring LID mice inoculated with a highly aggressive melanoma cell line (B16Fluc) that metastasizes primarily to the lungs [53]. B16Fluc is a luminescent derivative of the B16 mouse melanoma cell line. Therefore tumor progression and regression can be visualized and quantified in vivo using bioluminescence imaging technology (BLI) [53]. LID and its control mice were intravenously injected with B16Fluc ($2\times10^5$ cells/mouse) melanoma cells and treated for 2 cycles with high-dose DXR (FIG. 7A, n=4/LID-B16, n=5/LID-B16-DXR, n=8/Control-B16, n=7/Control-B16-DXR). Although IGF-I plays a major role in transformation, anti-apoptosis, tumor growth, and metastasis [54], both LID and its control mice started to succumb to metastasis as early as 25 days following cancer inoculation. The 2 cycles of high-dose DXR extended survival time by delaying metastasis in all mice (FIGS. 29 B and C). A considerable number of control mice treated with DXR died from toxicity (43%) with signs of cardiac myopathy, whereas none of the LID mice died from DXR toxicity (FIGS. 29D and F). In addition, LID mice showed a sight advantage in weight maintenance (FIG. 29E). 90 days after cancer inoculation, all control mice that received chemotherapy had died from either cancer metastasis or doxorubicin toxicity, but 60% of LID mice that received 2 cycles of high-dose DXR treatment were cancer-free with no apparent toxic side-effects, (FIG. 29B, P<0.05). All the LID mice deaths were caused by cancer metastases. The progression of cancer and death in B16Fluc injected control and LID mice treated with DXR was similar suggesting that reduction of circulating IGF-I protects the host but not cancer cells against high dose chemotherapy.

Discussion

Figure 30:
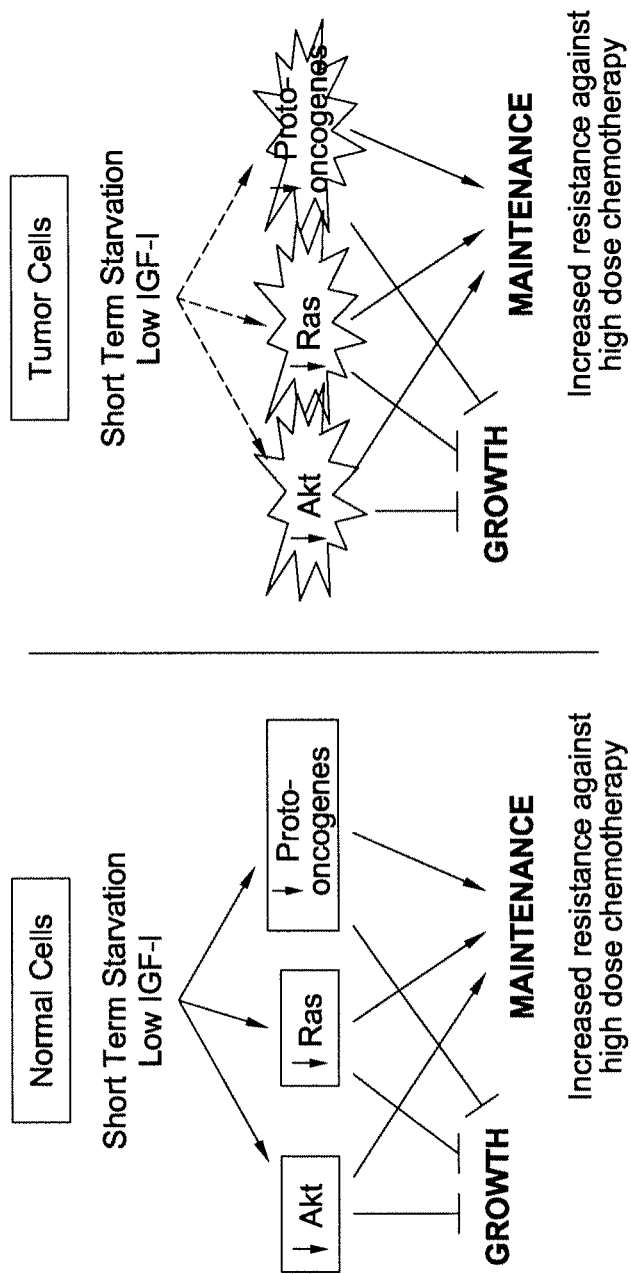
FIG. 30. A model for differential stress resistance (DSR) in response to short-term starvation (STS) and reduced IGF-I. Normal cells respond to starvation or the absence of growth signals by undergoing cell cycle arrest and shifting energy to maintenance. Since one of the hallmarks of cancer cells is the ability to grow or remain in a growth mode regardless of external regulatory signals (including IGF-IR, Ras, and Akt), cancer cells are predicted to fail to or only partially enter into a protective maintenance mode in response to starvation and low IGF-I.
Figure 31:
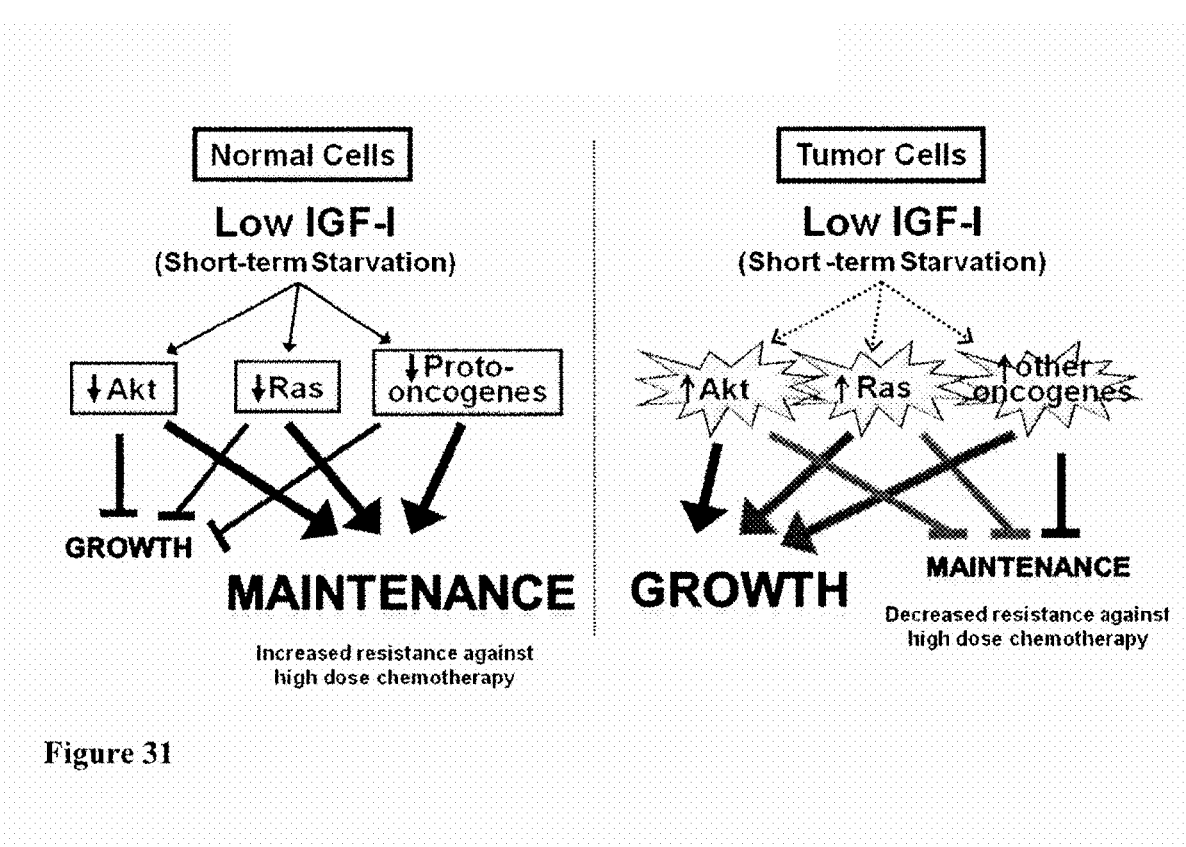
FIG. 31. DIFFERENTIAL STRESS RESISTANCE BY STARVATION. In normal cells, downstream effectors of the IGF-I and other growth factor pathways, including the Akt, Ras and other proto-oncogenes, are down-regulated in response to the reduction in growth factors caused by starvation. This down-regulation blocks/reduces growth and promotes protection to chemotherapy. By contrast, oncogenic mutations render tumor cells less responsive to STS due to their independence from growth signals. Therefore, cancer cells fail to or only partially respond to starvation conditions and continue to promote growth instead of protection against oxidative stress and high dose chemotherapy.
Figure 32:
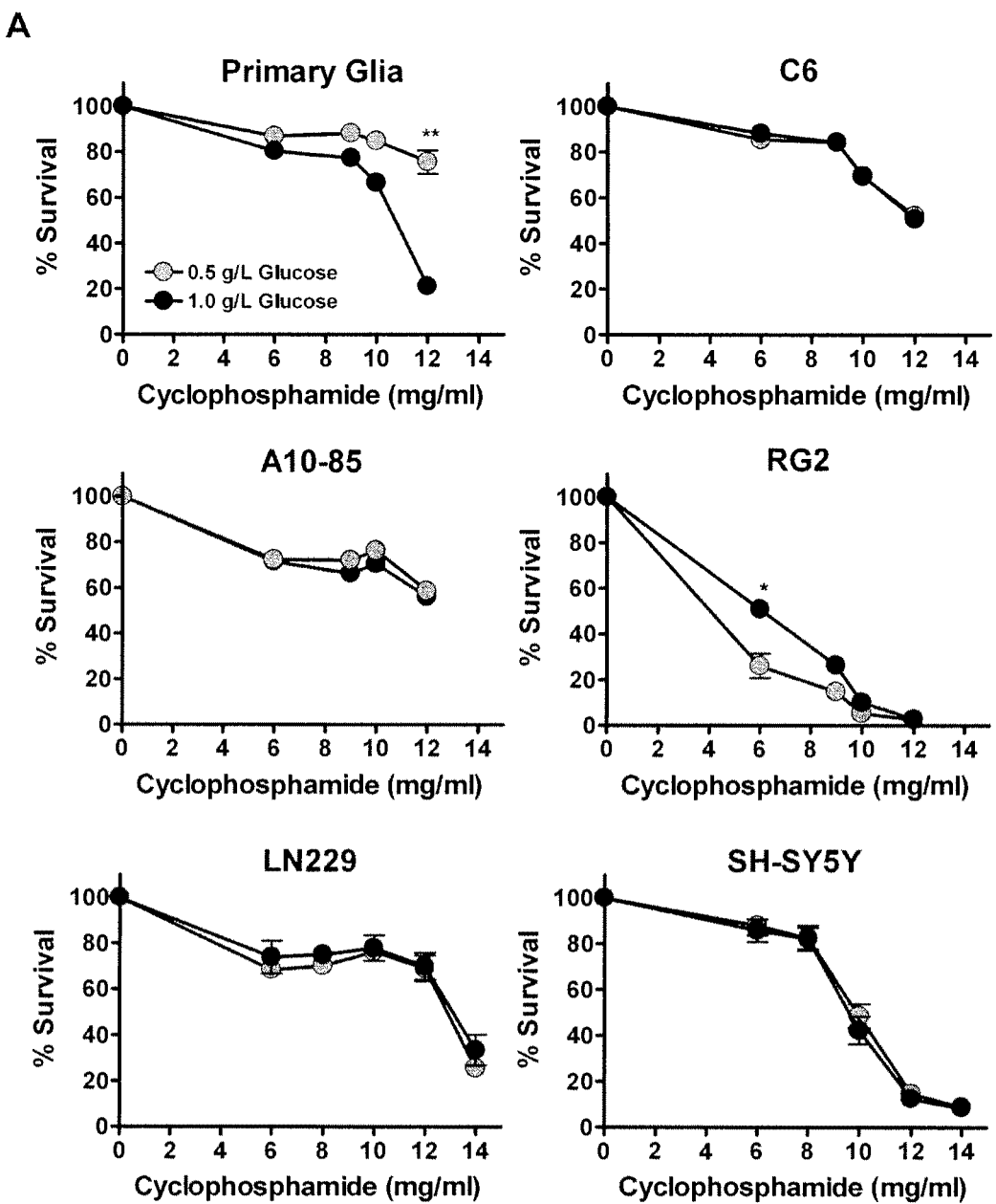
FIG. 32. Differential Stress Resistance in Starved Mammalian Cells. Primary rat glial cells, rat glioma cell lines (C6, A10-85, and RG2), human glioma (LN229) and human neuroblastoma (SH-SY5Y) cell lines were tested. (* p<0.05, ** p<0.01)
Figure 33E:
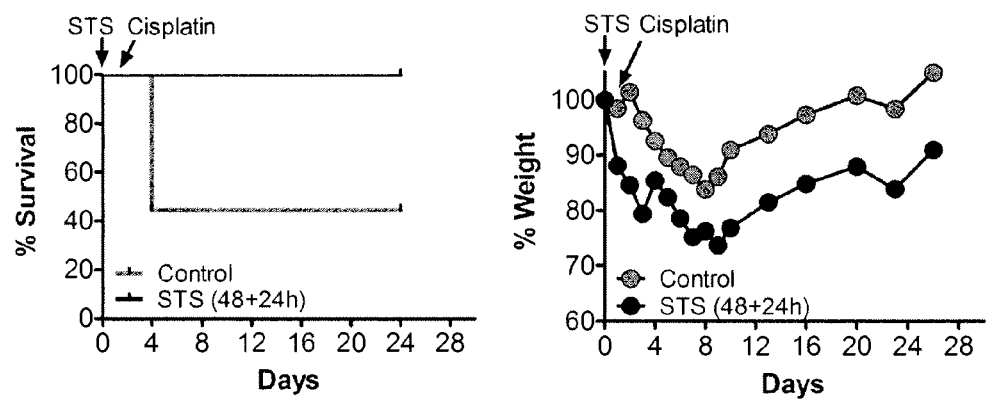
FIG. 33. Short-term starvation (STS) Protects Mice From Chemo-toxicity. Mice from 3 different genetic backgrounds (A: A/J B: CD-1 C: Nude) were starved for 48-60 hours and challenged with high-dose etoposide (100-110 mg/kg). (p<001, * p<0.05) (E) 8-week old CD-1 female mice were starved for 48 hours prior to and 24 h following administration of 12 mg/kg of cisplatin. (p<0.05) (F) 15-week old A/J female mice were starved for 48 hours and challenged with 16 mg/kg of doxorubicin. (p<0.05)
Figure 33F:
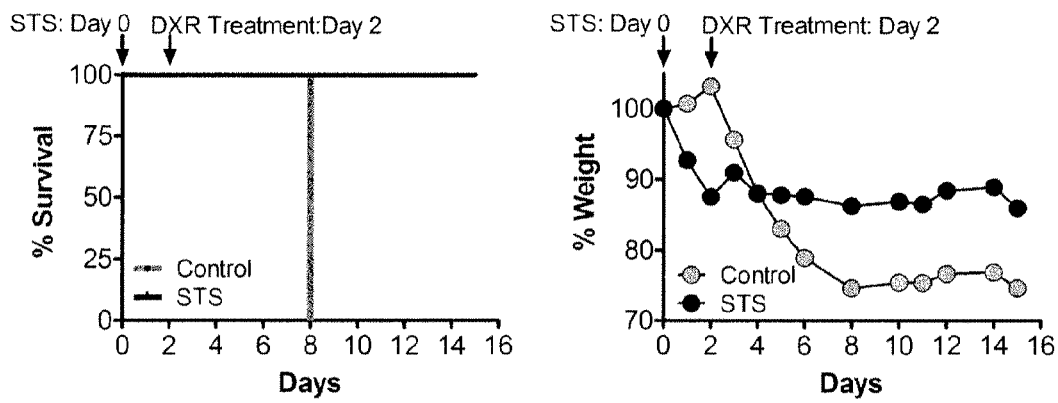
Figure 34A:
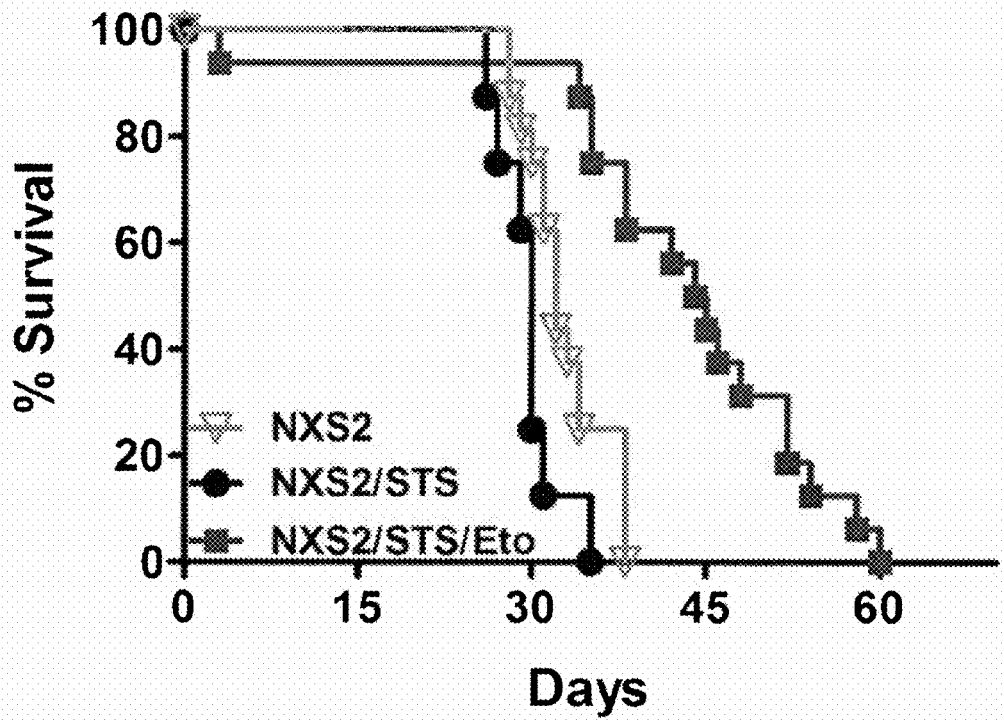
FIG. 34. Differential Stress Resistance in Starved Mice with Neuroblastoma. (A) NXS2 (neuroblastoma)-bearing mice were starved for 48 hours (STS) prior to chemotherapy with high-dose etoposide (80 mg/kg). (B) Experimental procedures. (C) STS may sensitize NXS2 cells against doxorubicin and cisplatin.
Figure 34B:
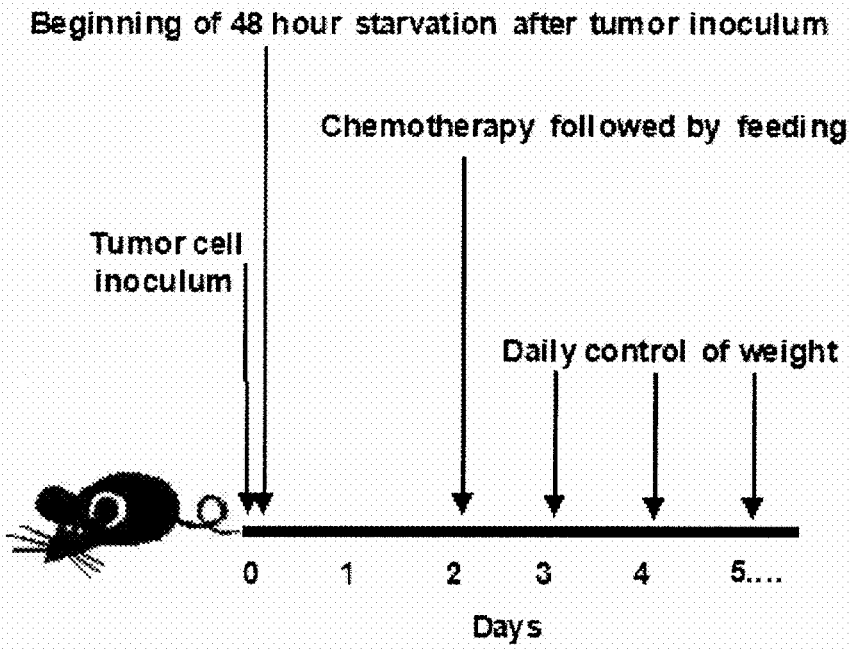
Figure 34C:
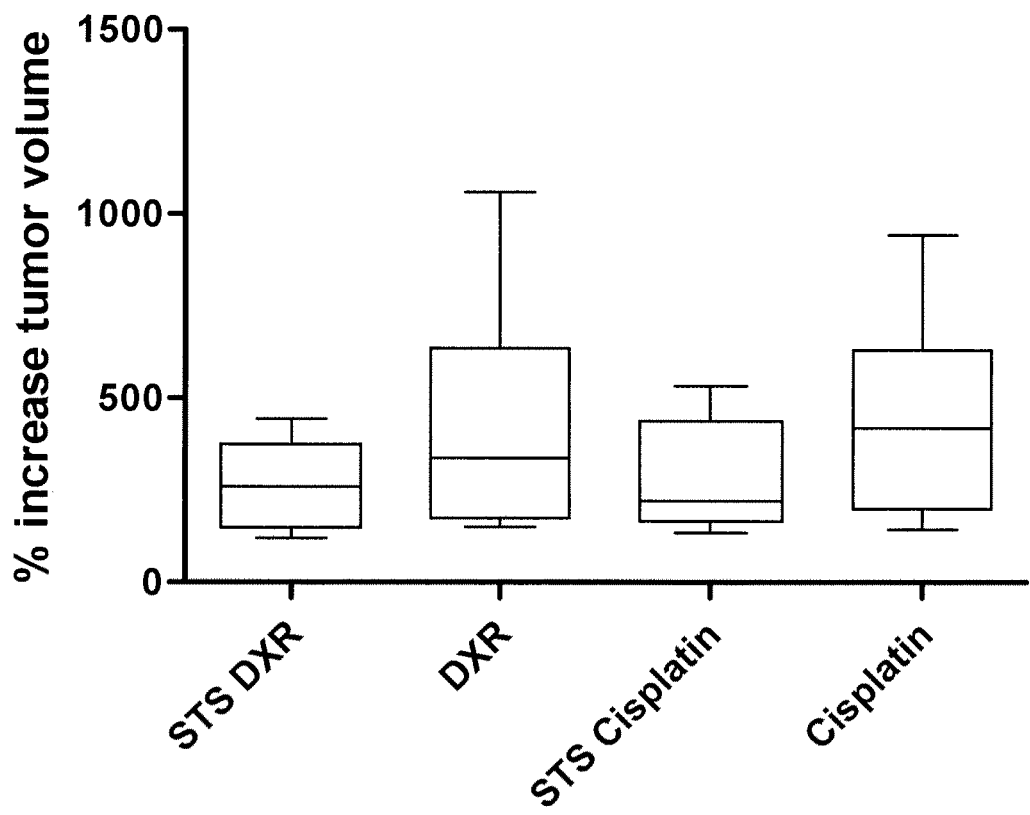
Figure 35:
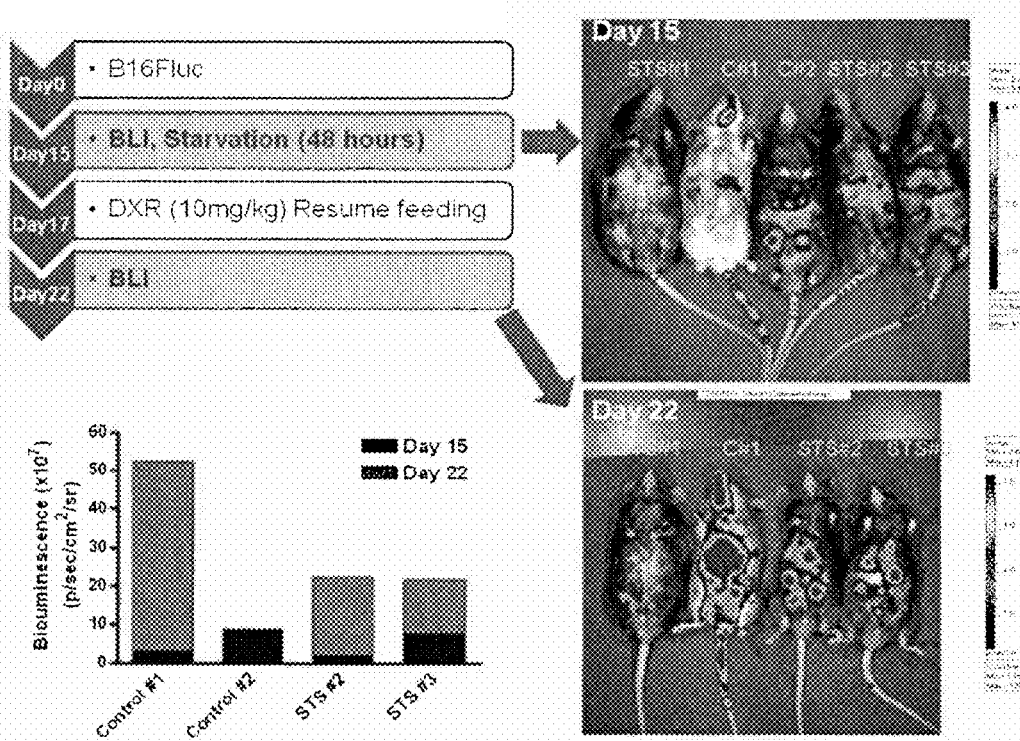
FIG. 35. Differential Stress Resistance in Starved Mice with B16 Melanoma Cells. STS sensitizes B16 melanoma cells against DXR: Mice starved 48 hour prior to chemotherapy showed a greater tumor response which was further quantified using bioluminescence technology.

In a previous report, we described a short-term starvation (STS) based DSR method to protect the host but not cancer cells against high-dose chemotherapy. The basis for this appears to be the existence of a non-dividing or low division "maintenance mode" which cells enter in response to starvation for the purpose of investing the remaining energy resources in cellular protection against various insults (FIG. 30). Here we investigated the role of IGF-I and the IGF-IR in the regulation of DSR in mammals and determined that a major reduction in circulating IGF-I can protect the host but not cancer cells against chemotherapy. Low levels of IGF-I can reduce intracellular mitogenic signaling pathways, including Ras and Akt, which are components of two of the major pathways downstream of the IGF-IR. We believe this reduction of mitogenic stimuli allows normal cells to undergo cell cycle arrest [55,56] and shift the energy towards repair by mechanisms regulated by proteins including Akt, Ras/ERK, FOXO, SirT1, and ER stress response [6,18,23,35], thereby entering a high protection 'maintenance mode' [6,56]. On the other hand, cancer cells are self sufficient in growth signals and are less or not responsive to physiological anti-growth signals [6,20,35]. This could explain the differential protection against DXR observed in our $R^+$ and $R^-$ cells treated under complete confluence. In addition, our yeast experiments show that the deletion of the homologs of RAS and/or AKT/S6K promotes defense against DXR, but the expression of the oncogenic $RAS2^{val19}$ reverses the protection independently of cell division. These results raise the possibility that oncogenic mutations that activate pathways ranging from the Ras to the PTEN/AKT to the PKA pathway may be sufficient to reverse the protective effect of the down-regulation of IGF-I signalling in canter cells, thus allowing differential protection of host and various cancers. Notably, IGF-IR may represent simply one of a number of receptors that can activate Ras, Akt etc in normal cells and therefore only one of the receptors that can be down-regulated to provide differential stress resistance.

Preclinical studies show that IGF-IR targeting strategies can be effective in the treatment of multiple myelomas, prostate, breast and colon cancer in addition to other cancers [42,57]. The antitumor effect seen with such agents is thought to be dependent on apoptosis resulting from IGF-IR inactivation [57]. However, it must be noted that IGF-IR blockade could also trigger apoptosis in normal cells, and may not protect against high dose chemotherapy by interfering with the growth/recovery of blood cells. As observed with our LID mice, reduced IGF-I, unlike IGF-IR blockade, does not cause cancer cell death but can selectively enhance the resistance of normal cells against chemotoxicity and may sensitize cancer cells to chemotherapy. This is in agreement with our recent observation regarding the normal development of prostatic carcinoma in the LID-TRAMP model [46]. Based on our results from etoposide treated LID mice, strategies that reduce circulating IGF-I may also increase the toxicity of certain chemotherapy drugs. Therefore, the compatibility between each drug and IGF-I reduction/blockade therapy should be carefully tested in pre-clinical studies before being considered as a candidate.

In summary, our studies in mice indicate that a major reduction in circulating IGF-I can provide enhanced resistance to the host, but not cancer cells against chemotherapy, thus providing the foundation for a method to enhance cancer treatment without the need to fast. However, the combination of fasting and IGF-I reduction could result in an even more pronounced effect. It is important to note that the reduction in circulating IGF-I has the potential to be utilized for a variety of cancers.

Methods

Cell Lines

Primary mixed glial cells were obtained from the cerebral cortex of 1 to 3 day old Sprague Dawley rat pups (Charles River) as described before [58]. Cells cultured for 10-14 nbdays in DMEM/F12 medium with 10% fetal bovine serum (PBS) were used in assays. C6, A10-85, and 9L rat glioma cell lines, kindly provided by Dr. Chen (University of Southern California) and $R^+$ and $R^-$ cells, kindly provided by Dr. Baserga (Thomas Jefferson University), were maintained in DMEM/F12 with 10% FBS at 37° C. under 5% CO. $R^+$ and $R^-$ cells are mouse embryonic fibroblast (MEF) that overexpress human IGF-IR or have IGF-IR deletion, respectively, and were generated as previously described [33]. R$^-$ cells are 3T3-like cells originating from mouse embryos with a targeted disruption of the igf1r genes [33]. The R$^+$ cell line was derived from R$^-$ cells, and express the human igf1r cDNA under the control of the cytomegalovirus (CMV) promoter [33]. Primary neurons from embryonic day 18 Sprague-Dawley rat cerebral cortices were dissociated in neurobasal medium (Invitrogen) supplemented with 0.5 mM L-glutamine, 25 µM L-glutamic acid and 2% B-27 and plated at 640 cells/mm$^2$ in 96-well plates which were pre-coated with 10 µg/ml poly-D-lysine dissolved in Borax buffer (0.15 M, pH 8.4). Neurons were maintained at 37° C. in 5% CO$_2$ in neurobasal medium supplemented with B-27 and 0.5 mM L-glutamine for 4 days. PC12 rat pheochromocytoma cell line (ATCC) was maintained in F12K medium supplemented with 15% horse serum and 2.5% fetal bovine serum at 37° C. under 5% CO$_2$, In Vitro IGF-I Modulation All cells were grown to confluence prior to treatments. The inhibition of IGF-IR activation was achieved with monoclonal anti-IGF-IR antibody (αIR3, 1pg/ml; Calbiochem) in DMEM/F12 1% FBS for 24 hours. Serum restriction was performed by incubating cells in DMEM/F12 with either 10% or 1% FBS for 24 hours. IGF-I treatment was carried out by incubating cells for 48 hours in DMEM/F12 with 1% FBS and rhIGF-I (100 ng/ml, ProSpec-Tany TechnoGene, Rehovot, Israel), which is shown to be within the IGF-I level range for middle age humans [32].

In Vitro Drug Treatments

Primary glia and C6, A10-85, and 9L rat glioma cells were seeded at 2×10$^4$ cells/well and incubated for 48 hours in 96 well plates prior to treatments to reach confluence and minimize differences in proliferation. Various IGF-I modulating pretreatments were followed by cyclophosphamide (CP, Sigma) treatments. Glial cells have been reported to express cytochrome P450 and thus are capable of metabolizing the prodrug CP [59,60]. CP was prepared in DMEM/F12 with 1% FBS at 40 mg/ml and was filter sterilized. The stock solution was stored at 4° C. for no longer than 2 weeks. Cells were incubated with varying concentrations of cyclophosphamide (0-15 mg/ml) for 10 hours in DMEM/F12 with 1% FBS. R$^+$ and R$^-$ cells were seeded at 2×10$^4$ cells/well and incubated in 96 well plates and were also grown to confluence (2 days) prior to doxorubicin (DXR) treatments. DXR was prepared at 5 mg/ml in sterile saline. Cells were treated with DXR for 24 hours and 48 hours prior to survival analysis by MTT reduction. NXS2 neuroblastoma cells treated with different concentrations of etoposide (1-3 µM) in the presence or absence of octreotide (10 and 50 µM) for 72 hours were harvested by scraping, washed with complete medium, and incubated with trypan blue (0.04%; Sigma; St. Louis, Mo.) for 1 minute at 37° C. The cells were then placed in a Burker chamber (Teconovetro, Monza Milan, Italy) and counted with a contrast phase microscope (Olympus Optical Co LTD, Tokyo, Japan). Trypan blue-positive cells (i.e., dead cells), trypan blue-negative cells (i.e., living cells), and total cells were counted per microscope field (four fields were counted for each treatment). The proportion of dead (or living) cells was calculated by dividing the number of dead (or living) cells by the total number of cells per field. Primary rat neurons and PC12 cells were treated with IGF-I and paraquat to determine the effect of IGF-I on oxidative stress. Cortical neurons were treated for 24 hours in Eagle's minimal essential medium (Invitrogen) supplemented with 21 mM glucose and 1% horse serum. PC12 cells were plated at 5×10$^4$ cells/well onto poly-D-lysine coated 96-well plates and were grown for 24 hours in F12K 1% HS. Both types of cells were then treated with either 100 µM of paraquat alone or followed 30 minutes later by IGF-I (100 ng/ml) or IGF-I (100 ng/ml) alone in appropriate media. Survival was determined by the MTT reduction assay and presented as percentage of treated to control.

In Vitro Viability Assays

Cytotoxicity was measured by either lactate dehydrogenase (LDH) released using the CytoTox 96 Non-Radioactive Cytotoxicity Assay kit (Promega) or the ability to reduce methylthiazolyldiphenyl-tetrazolium bromide (MTT). MTT is reduced in the mitochondria (metabolically active cells) by mitochondrial reductase enzymes to form insoluble purple formazan crystals, which are solubilized by the addition of a detergent [1]. Briefly, MTT was prepared at 5 mg/ml in PBS and was diluted in DMEM/F12 1% PBS media to a final concentration of 0.5 mg/ml for assays. Following experimental treatments, media was replaced with 100 µl of MTT and cells were incubated for 3~4 hours at 37° C. Formazan crystals were dissolved overnight (16 hours) at 37° C. with 100 µl lysis buffer ((w/v) 15% SDS, (v/v) 50% dimethylformamide, pH 4.7). Survival was presented as percentage of MTT reduction level of treated cells to control cells. Absorbance was read at 570 nm using a microplate reader SpectraMax 250 (Molecular Devices) and SoftMax Pro 3.0 software (Molecular Devices).

Comet Assay Protocol

Cells were diluted to 10$^5$/ml in culture medium (DMEM/F12 with 10% FBS), and treated with 50 µM DXR for 1 hour at 37° C. Cells were then washed once with ice cold PBS and subject to CometAssay (Trevigen, Inc, Gaithersburg, Md.) according to the manufacturer's recommended procedure. Comet images were acquired with a Nikon Eclipse TE300 fluorescent microscope and analyzed with the Comet Score software (TriTek Corp., ver1.5). 100-300 cells were scored for each genotype/treatment group.

Plasma mGH, mIGF-I, and mIGFBP-1 and -3 Measurements

Plasma mIGF-I and mIGFBP-1 and -3 assays were performed as previously described by in-house ELISA assay using recombinant mouse IGF-I protein and monoclonal antibodies from R&D systems (Minneapolis, Minn.) [61]. mGH levels were measured by rat/mouse GH ELISA kit (ALPCO Diagnostics).

Blood Glucose Measurements

Following a 72 hour fast, mice were anesthetized with 2% inhalant isoflurane and blood was collected by left ventricular cardiac puncture. Blood glucose was measured using the Precision Xtra blood glucose monitoring system (Abbott Laboratories, USA).

STS/Octreotide Treatments in Mice

The murine NX3IT28 cell line was generated by hybridization of the GD2-negative C1300 murine neuroblastoma cell line (A/J background) with murine dorsal root ganglional cells from C57BL/6J mice, as previously described [62]. The NXS2 subline was then created by the selection of NX3IT28 cells with high GD2 expression [43]. Female A/J mice, weighing 15-18 g were purchased from Harlan Laboratories (Harlan Italy, S. Pietro al Natisone, Italy) and housed in sterile cages under specific virus and antigen-free conditions. All procedures were reviewed and approved by licensing and ethical committee of the National Cancer Research Institute, Genoa, Italy, and by the Italian Ministry of Health. A/J mice were pretreated with 1 mg/kg/day doses of octreotide (OCT, ProSpec-Tany TechnoGene, Rehovot, Israel) for 4 days given slowly through the tail vein in a volume of 100 µl. Following the 4 days of octreotide treatment, mice were intravenously injected with NXS2 cells (200,000 cells/mouse), as previously described [43]. After tumor cell injection, some animals were starved for 48 hours and then I.V. injected with 80 mg/kg of etoposide (Teva Pharma B.V., Mijdrecht, Holland), administered as a single dose. Additional daily doses of OCT were administered for 4 days after chemotherapy. Control groups without dietary intervention and OCT treatment were also investigated.

Octreotide pre-treatment: 4 days 1 mg/kg/day on days 1-4
NXS2: 200,000/mouse on day 4
STS: from day 4 to day 6 (after tumor cell injection)
Etoposide: 80 mg/kg on day 7
Octreotide post-treatment: days 8-11

To determine toxicity and efficacy, mice were monitored routinely for weight loss and general behavior. The animals were killed by cervical dislocation after being anesthetized with xilezine (Xilor 2%, Bio98 Srl, Milan, Italy) when they showed signs of poor health, such as adbominal dilatation, dehydration, or paraplegia.

Stress Resistance Against Chemotherapy Treatments in LID Mice

LID mice of 75-100 weeks of age were used to model human cancer onset [63]. Since liver is the major source of IGF-I production, mice with a conditional hepatic igf1 gene knockout have reduced circulating IGF-I levels by 80% [46]. Because albumin is expressed in the liver after 10 days of birth, resulting in liver igf1 gene deletion, LID mice do not experience early death, growth retardation, or developmental defects like the igf1 gene knock-out (igf1−/−) mice [45,64, 65]. LID and its control mice were given 100 mg/kg etoposide intravenously. CP was given at 500 mg/kg. CP was dissolved in saline at 40 mg/ml and injected intraperitoneally. 5-Fluorouracil (5-FU, Sigma) was injected at 400 mg/kg intraperitoneally. Doxorubicin (DXR, Sigma) was prepared at 5 mg/ml in saline and injected intravenously first at 20 mg/kg and 22 days later at 28 mg/kg. All drugs have been selected from different categories. CP is a DNA alkylating agent [48], 5-FU is an antimetabolite [49], DXR is an intercalating agent and topoisomerase II inhibitor [50,51], and etoposide is a topoisomerase II inhibitor [52]. Etoposide, CP, 5-fluorouracil, and DXR have been shown to increase reactive oxygen species (ROS) and cause oxidative stress [66-69]. All mice were monitored daily for weight loss and signs of pain and stress. Mice determined terminally moribund were euthanized by $CO_2$ narcosis and necropsy was performed. Experiments were performed in accordance with Institutional Animal Care and Use Committee (University of Southern California, Los Angeles, Calif.) and the National Institutes of Health guidelines.

Differential Stress Resistance Against DXR in LID Mice

In order to study differential stress resistance, mice were injected with highly metastatic melanoma cells. LID and its control mice of ages 75-100 weeks were used. B16Fluc melanoma cells were a generous gift of Dr. Noah Craft at UCLA. B16Fluc cells are derivatives of B16 cells but produce light by stable transfection of the Firefly luciferase gene driven by the CMV promoter [53]. Prior to injection, cells were washed and resuspended in sterile saline. Each mouse received $2\times10^5$ cells in 100 µl saline, followed by another 100 µl of sterile saline to wash off remaining cells in the tails. 3 days after tumor inoculation, the first DXR (Bedford Laboratories) injections were given at 16 mg/kg. 2 weeks following the initial DXR administration, the second DXR injection was given at 12 mg/kg. Mice were observed daily for signs of stress or pain and body weight was recorded. Mice determined terminally moribund were sacrificed by $CO_2$ narcosis and necropsy was performed. The heart was collected for further histological examination.

Bioluminescence Imaging

For bioluminescence imaging (BLI), 5 mice were randomly selected from LID and control groups and followed throughout the experiment. All BLI imaging procedures were performed at the University of Southern California (USC) Small Animal Imaging core facility. Prior to imaging, mice were anesthetized using inhalant isoflurane (2%) and injected with 60 µl of 50 mg/kg of the luciferase substrate luciferin (Xenogen Corp.). 10 minutes later, mice were imaged in the supine position and scanned for 2 minutes using the IVIS 200 optical imaging system (Xenogen Corp.). Signal intensity was quantified as photon count rate per unit body area per unit solid angle subtended by the detector (units of photon/s/$cm^2$/steridian). Images were analyzed with the IVIS 200 and LIVING IMAGE 3D (Xenogen Corp.) software.

Histological Studies

The heart was collected for histological examinations of melanoma bearing LID and its control mice after 2 cycles of high-dose DXR. Heart failure has been documented as the major cause of acute toxicity after receiving DXR and therefore we examined the heart at the tissue level [70]. The organs were collected and washed in ice cold PBS and stored in 10% neutral buffered formalin (VWR). Samples were paraffin embedded and sectioned at 5 µm and H&E stained. Samples were examined and analyzed with Dr. Dubeau, professor of pathology at USC Keck School of medicine Yeast Strains All experiments were performed with the strain DBY746 (MATα, leu2-3, 112, his3Δ1, trp1-289, ura3-52, $GAL^+$), provided by D. Botstein, Massachusetts Institute of Technology, Cambridge, M A. The sch9Δ mutant has been described previously [71]. All the mutant strains were originated in the DBY746 background by one-step gene replacement [72].

Growth Conditions

Yeast chronological life span was monitored in expired SDC medium by measuring colony forming-units (CFUs) every 48 hours. The number of CFUs at day 1 was considered to be the initial survival (100%) and was used to determine the age-dependent mortality [73]. Cultures were treated once with 200 µM DXR on day 1.

Mutation Frequency Measurements

To characterize the type of mutations occurring in wild type and mutant strains, we measured the frequency of mutations of the CAN1 (YEL063) gene [74,75]. $Can^r$ mutations are mostly caused by point mutations as well as other DNA mutations including small insertion/deletion, complex events and gross chromosomal rearrangements (35). Cells from chronological aging cultures were plated them onto selective media every two days. The mutation frequency was calculated based on the number of viable cells as described previously [36,37].

REFERENCES

1. Collins I, Workman P (2006) New approaches to molecular cancer therapeutics. Nat Chem Biol 2: 689-700.
2. Mini E, Nobili S, Caciagli B, Landini I, Mazzei T (2006) Cellular pharmacology of gemcitabine. Ann Oncol 17 Suppl 5: v7-12.
3. Green M R, Manikhas G M, Orlov S, Afanasyev B, Makhson A M, et al. (2006) Abraxane, a novel Cremophor-free, albumin-bound particle form of paclitaxel for the treatment of advanced non-small-cell lung cancer. Ann Oncol 17: 1263-1268.
4. Links M, Lewis C (1999) Chemoprotectants: a review of their clinical pharmacology and therapeutic efficacy. Drugs 57: 293-308.

5. Hensley M L, Hagerty K L, Kewalramani T, Green D M, Meropol N J, et al. (2009) American Society of Clinical Oncology 2008 clinical practice guideline update: use of chemotherapy and radiation therapy protectants. J Clin Oncol 27: 127-145.
6. Raffaghello L, Lee C, Safdie F M, Wei M, Madia F, et al. (2008) Starvation-dependent differential stress resistance protects normal but not cancer cells against high-dose chemotherapy. Proc Natl Acad Sci USA 105: 8215-8220.
7. Kirkwood T B, Shanley D P (2005) Food restriction, evolution and ageing. Mech Ageing Dev 126: 1011-1016.
8. Shanley D P, Kirkwood T B (2000) Calorie restriction and aging: a life-history analysis. Evolution 54: 740-750.
9. Longo V D, Finch C E (2003) Evolutionary Medicine: from Dwarf Model Systems to Healthy Centenarians. Science 299: 1342-1346.
10. Bartke A (2005) Minireview: role of the growth hormone/insulin-like growth factor system in mammalian aging. Endocrinology 146: 3718-3723.
11. Thissen J P, Underwood L E, Ketelslegers J M (1999) Regulation of insulin-like growth factor-I in starvation and injury. Nutr Rev 57: 167-176.
12. Norrelund H (2005) The metabolic role of growth hormone in humans with particular reference to fasting. Growth Horm IGF Res 15: 95-122.
13. Maccario M, Aimaretti G, Grottoli S, Gauna C, Tassone F, et al. (2001) Effects of 36 hour fasting on GH/IGF-I axis and metabolic parameters in patients with simple obesity. Comparison with normal subjects and hypopituitary patients with severe GH deficiency. Int J Obes Relat Metab Disord 25: 1233-1239.
14. Merimee T J, Zapf J, Froesch E R (1982) Insulin-like growth factors in the fed and fasted states. J Clin Endocrinol Metab 55: 999-1002.
15. Tannenbaum G S, Rorstad O, Brazeau P (1979) Effects of prolonged food deprivation on the ultradian growth hormone rhythm and immunoreactive somatostatin tissue levels in the rat. Endocrinology 104: 1733-1738.
16. Frystyk J, Delhanty P J, Skjaerbaek C, Baxter R C (1999) Changes in the circulating IGF system during short-term fasting and refeeding in rats. Am Physiol 277: E245-252.
17. Holzenberger M, Dupont J, Ducos B, Leneuve P, Geloen A, et al. (2003) IGF-1 receptor regulates lifespan and resistance to oxidative stress in mice. Nature 421: 182-187.
18. Murakami S (2006) Stress resistance in long-lived mouse models. Exp Gerontol 41: 1014-1019.
19. Ayyadevara S, Alla R, Thaden J J, Shmookler Reis R J (2008) Remarkable longevity and stress resistance of nematode PI3K-null mutants. Aging Cell 7: 13-22.
20. Hanahan D, Weinberg R A (2000) The hallmarks of cancer. Cell 100: 57-70.
21. Xie L, Jiang Y, Ouyang P, Chen J, Doan H, et al. (2007) Effects of dietary calorie restriction or exercise on the PI3K and Ras signaling pathways in the skin of mice. J Biol Chem 282: 28025-28035.
22. Vogelstein B, Kinzler K W (2004) Cancer genes and the pathways they control. Nat Med 10: 789-799.
23. Li Y, Xu W, McBurney M W, Longo V D (2008) SirT1 Inhibition Reduces IGF-I/IRS-2/Ras/ERK1/2 Signaling and Protects Neurons. Cell Metab 8: 38-48.
24. Wei M, Fabrizio P, Hu J, Ge H, Cheng C, et al. (2008) Life span extension by calorie restriction depends on Rim15 and transcription factors downstream of Ras/PKA, Tor, and Sch9. PLoS Genet 4: e13.
25. Cotterill A M, Holly J M, Wass J A (1993) The regulation of insulin-like growth factor binding protein (IGFBP)-1 during prolonged fasting. Clin Endocrinol (Oxf) 39: 357-362.
26. Katz L E, Satin-Smith M S, Collett-Solberg P, Baker L, Stanley C A, et al. (1998) Dual regulation of insulin-like growth factor binding protein-1 levels by insulin and cortisol during fasting. J Clin Endocrinol Metab 83: 4426-4430.
27. Norrelund H, Frystyk J, Jorgensen J O, Moller N, Christiansen J S, et al. (2003) The effect of growth hormone on the insulin-like growth factor system during fasting. J Clin Endocrinol Metab 88: 3292-3298.
28. Lee K W, Cohen P (2002) Nuclear effects: unexpected intracellular actions of insulin-like growth factor binding protein-3. J Endocrinol 175: 33-40.
29. Brown-Borg H M, Rakoczy S G, Romanick M A, Kennedy M A (2002) Effects of growth hormone and insulin-like growth factor-1 on hepatocyte antioxidative enzymes. Exp Biol Med 227: 94-104.
30. Suh Y, Atzmon G, Cho M O, Hwang D, Liu B, et al. (2008) Functionally significant insulin-like growth factor I receptor mutations in centenarians. Proc Natl Acad Sci USA 105: 3438-3442.
31. Yan L, Vatner D E, O'Connor J P, Ivessa A, Ge H, et al. (2007) Type 5 adenylyl cyclase disruption increases longevity and protects against stress. Cell 130: 247-258.
32. Manetta J, Brun J F, Maimoun L, Callis A, Prefaut C, et al. (2002) Effect of training on the GH/IGF-I axis during exercise in middle-aged men: relationship to glucose homeostasis. Am J Physiol Endocrinol Metab 283: E929-936.
33. Drakas R, Tu X, Baserga R (2004) Control of cell size through phosphorylation of upstream binding factor 1 by nuclear phosphatidylinositol 3-kinase. Proc Natl Acad Sci USA 101: 9272-9276.
34. Baserga R (1999) The IGF-I receptor in cancer research. Exp Cell Res 253; 1-6.
35. Longo V D, Lieber M R, Vijg J (2008) Turning anti-ageing genes against cancer. Nat Rev Mol Cell Biol 9: 903-910.
36. Madia F, Gattazzo C, Wei M, Fabrizio P, Burhans W C, et al. (2008) Longevity mutation in SCH9 prevents recombination errors and premature genomic instability in a Werner/Bloom model system. J Cell Biol 180: 67-81.
37. Madia F, Gattazzo C, Fabrizio P, Longo V D (2007) A simple model system for age-dependent DNA damage and cancer. Mech Ageing Dev 128: 45-49.
38. Ishikawa M, Mizobuchi M, Takahashi H, Bando H, Saito S (1997) Somatostatin release as measured by in vivo microdialysis: circadian variation and effect of prolonged food deprivation. Brain Res 749: 226-231.
39. Hejna M, Schmidinger M, Raderer M (2002) The clinical role of somatostatin analogues as antineoplastic agents: much ado about nothing? Ann Oncol 13: 653-668.
40. Susini C, Buscail L (2006) Rationale for the use of somatostatin analogs as antitumor agents. Ann Oncol 17: 1733-1742.
41. Zalatnai A, Schally A V (1989) Treatment of N-nitrosobis (2-oxopropyl)amine-induced pancreatic cancer in Syrian golden hamsters with D-Trp-6-LH-RH and somatostatin analogue RC-160 microcapsules. Cancer Res 49: 1810-1815.
42. Pollak M N, Schernhammer E S, Hankinson S E (2004) Insulin-like growth factors and neoplasia. Nat Rev Cancer 4: 505-518.

43. Lode H N, Xiang R, Varki N M, Dolman C S, Gillies S D, et al. (1997) Targeted interleukin-2 therapy for spontaneous neuroblastoma metastases to bone marrow. J Natl Cancer Inst 89: 1586-1594.
44. Migliaccio E, Giorgio M, Mele S, Pelicci G, Reboldi P, et al. (1999) The p66shc adaptor protein controls oxidative stress response and life span in mammals. Nature 402: 309-313.
45. Yakar S, Liu J L, Stannard B, Butler A, Accili D, et al. (1999) Normal growth and development in the absence of hepatic insulin-like growth factor I. Proc Natl Acad Sci USA 96: 7324-7329.
46. Anzo M, Cobb L J, Hwang D L, Mehta H, Said J W, et al. (2008) Targeted deletion of hepatic Igf1 in TRAMP mice leads to dramatic alterations in the circulating insulin-like growth factor axis but does not reduce tumor progression. Cancer Res 68: 3342-3349.
47. Patel A C, Nunez N P, Perkins S N, Barrett J C, Hursting S D (2004) Effects of energy balance on cancer in genetically altered mice, J Nutr 134: 3394S-3398S.
48. de Jonge M E, Huitema A D, Rodenhuis S, Beijnen J H (2005) Clinical pharmacokinetics of cyclophosphamide. Clin Pharmacokinet 44: 1135-1164.
49. Longley D B, Harkin D P, Johnston P G (2003) 5-fluorouracil: mechanisms of action and clinical strategies. Nat Rev Cancer 3: 330-338.
50. Zeman S M, Phillips D R, Crothers D M (1998) Characterization of covalent adriamycin-DNA adducts. Proc Natl Acad Sci USA 95: 11561-11565.
51. Tewey K M, Rowe T C, Yang L, Halligan B D, Liu L F (1984) Adriamycin-induced DNA damage mediated by mammalian DNA topoisomerase II. Science 226: 466-468.
52. Hande K R (1998) Etoposide: four decades of development of a topoisomerase II inhibitor. Eur J Cancer 34: 1514-1521.
53. Craft N, Bruhn K W, Nguyen B D, Prins R, Liau L M, et al. (2005) Bioluminescent imaging of melanoma in live mice. J Invest Dermatol 125: 159-165.
54. Samani A A, Yakar S, LeRoith D, Brodt P (2007) The role of the IGF system in cancer growth and metastasis: overview and recent insights. Endocr Rev 28: 20-47.
55. Keyomarsi K, Pardee A B (2003) Selective protection of normal proliferating cells against the toxic effects of chemotherapeutic agents. Prog Cell Cycle Res 5: 527-532.
56. Blagosklonny M V, Pardee A B (2001) Exploiting cancer cell cycling for selective protection of normal cells. Cancer Res 61: 4301-4305.
57. Tao Y, Pinzi V, Bourhis J, Deutsch E (2007) Mechanisms of disease: signaling of the insulin-like growth factor 1 receptor pathway—therapeutic perspectives in cancer. Nat Clin Pract Oncol 4: 591-602.
58. McCarthy K D, de Vellis J (1980) Preparation of separate astroglial and oligodendroglial cell cultures from rat cerebral tissue. J Cell Biol 85: 890-902.
59. Geng J, Strobel H W (1998) Expression, induction and regulation of the cytochrome P450 monooxygenase system in the rat glioma C6 cell line. Brain Res 784: 276-283.
60. Kempermann G, Knoth I R, Gebicke-Haerter P J, Stolz B J, Volk. B (1994) Cytochrome P450 in rat astrocytes in vivo and in vitro: intracellular localization and induction by phenyloin. J Neurosci Res 39: 576-588.
61. Hwang D L, Lee P D, Cohen P (2008) Quantitative ontogeny of murine insulin-like growth factor (IGF)-I, IGF-binding protein-3 and the IGF-related acid-labile subunit. Growth Horm IGF Res 18: 65-74.
62. Greene L A, Shain W, Chalazonitis A, Breakfield X, Minna J, et al. (1975) Neuronal properties of hybrid neuroblastoma X sympathetic ganglion cells. Proc Natl Acad Sci USA 72: 4923-4927.
63. Jemal A, Siegel R, Ward E, Hao Y, Xu J, et al. (2008) Cancer statistics, 2008. CA Cancer J Clin 58: 71-96.
64. Liu J P, Baker J, Perkins A S, Robertson E J, Efstratiadis A (1993) Mice carrying null mutations of the genes encoding insulin-like growth factor I (Igf-1) and type 1 IGF receptor (Igf1r). Cell 75: 59-72.
65. Baker J, Liu J P, Robertson E J, Efstratiadis A (1993) Role of insulin-like growth factors in embryonic and postnatal growth. Cell 75: 73-82.
66. Tsai-Turton M, Luong B T, Tan Y, Luderer U (2007) Cyclophosphamide-induced apoptosis in COV434 human granulosa cells involves oxidative stress and glutathione depletion. Toxicol Sci 98: 216-230.
67. Manda K, Bhatia A L (2003) Prophylactic action of melatonin against cyclophosphamide-induced oxidative stress in mice. Cell Biol Toxicol 19: 367-372.
68. Kurosu T, Fukuda T, Miki T, Miura O (2003) BCL6 overexpression prevents increase in reactive oxygen species and inhibits apoptosis induced by chemotherapeutic reagents in B-cell lymphoma cells. Oncogene 22: 4459-4468.
69. Hwang J T, Ha J, Park O J (2005) Combination of 5-fluorouracil and genistein induces apoptosis synergistically in chemo-resistant cancer cells through the modulation of AMPK and COX-2 signaling pathways. Biochem Biophys Res Commun 332: 433-440.
70. Rajagopalan S, Politi P M, Sinha B K, Myers C E (1988) Adriamycin-induced free radical formation in the perfused rat heart: implications for cardiotoxicity. Cancer Res 48: 4766-4769.
71. Fabrizio P, Pozza F, Pletcher S D, Gendron C M, Longo V D (2001)
Regulation of longevity and stress resistance by Sch9 in yeast. Science 292: 288-290.
72. Brachmann C B, Davies A, Cost G J, Caputo E, Li J, et al. (1998) Designer deletion strains derived from *Saccharomyces cerevisiae* S288C: a useful set of strains and plasmids for PCR-mediated gene disruption and other applications. Yeast 14: 115-132.
73. Fabrizio P, Longo V D (2003) The chronological life span of *Saccharomyces cerevisiae*. Aging Cell 2: 73-81.
74. Fabrizio P, Gattazzo C, Battistella L, Wei M, Cheng C, et al. (2005) Sir2 blocks extreme life-span extension. Cell 123: 655-667.
75. Fabrizio P, Battistella L, Vardavas R, Gattazzo C, Liou L L, et al. (2004) Superoxide is a mediator of an altruistic aging program in *Saccharomyces cerevisiae*. J Cell Biol 166: 1055-1067.
76. Villani F, Galimberti M, Zunino F, Monti E, Rozza A, et al. (1991) Prevention of doxorubicin-induced cardiomyopathy by reduced glutathione. Cancer Chemother Pharmacol 28: 365-369.

EXAMPLE V

Chemotherapy toxic side effects including myelosuppression, gastrointestinal damage, and fatigue, limit the dose and length of cancer therapy. Although, several chemoprotectants have been shown to provide protection to certain tissues their differential effects on normal and cancer cells are limited. Recently, we reported that short-term starvation (STS) selectively protects normal cells and mice but not cancer cells against chemotherapy (differential stress resistance, DSR).

Here, we investigated the mechanism of STS-dependent protection. In mice, a 72-hour fast reduced IGF-I by 70% and increased the level of the IGF-I inhibitor IGFBP1 10-fold. Reduction of IGF-I/IGF-I signaling protected primary glia, but not glioma cells against cyclophosphamide and protected mouse embryonic fibroblasts (MEFs) against doxorubicin-dependent DNA damage. LID mice with a 70-80% reduction in circulating IGF-I levels displayed protection against 3 out of 4 chemotherapy drugs tested and melanoma-bearing LID mice treated with doxorubicin had a significantly improved long-term survival rate (60% vs. 0%, LID and control respectively) with less chemo toxicity. These results suggest that IGF-I is a potent inhibitor of protection in normal but not cancer cells.

EXAMPLE VI

Short-Term Starvation-Based Strategy for Differential Protection Against Multiple Chemotherapy Agents Abstract The side effects of chemotherapy are a major limiting factor in cancer treatment. Although progress has been made in the development of chemoprotectants, they are not widely used due to their drug- and tissue-specificity. Our previous research revealed the role of starvation and starvation-regulated genetic pathways in the protection of cells and organisms against a variety of toxins. Recently, we reported that short-term starvation (STS) selectively protected normal cells and mice against etoposide but provided no, or minor, protection to neuroblastoma cells in vitro and in vivo, respectively (differential stress resistance, DSR). Our DSR hypothesis is based on the fact that stress resistance is inhibited by oncogenic pathways and thus cannot be activated in cancer cells. We have investigated whether STS protects mice against other drugs and studied its effect on the resistance of different malignant cells to chemotherapy. The reported STS regimen consisted of a 48-60 hours fast prior to chemotherapy administration. Here we show that protection to cisplatin requires a 48-hour pre-chemo and 24-hour post-chemo fast. Using luciferase-expressing melanoma and neuroblastoma cells, we monitored the effect of chemotherapy in vivo. Our results confirmed that STS protects the host from chemotoxicity, and suggest that it does not protect neuroblastoma cells and may sensitize melanoma cells to multiple cycles of doxorubicin treatment. These results indicate that short-term starvation has the potential to be effective in the differential protection of normal and cancer cells against a wide range of chemo drugs and may enhance chemotherapy efficacy and health outcomes.

Materials and Methods

Cell Culture

Primary mixed glial cells were obtained from the cerebral cortices of 1 to 3 days old Sprague Dawley rat pups (Charles River). Cells cultured for 10-14 days in DMEM/F12 medium (Invitrogen) with 10% fetal bovine serum (FBS) were used. C6, A10-85, 9L and RG2 rat glioma cell lines and LN229 human glioma cell line, kindly provided by Dr. Chen (University of Southern California) and SH-SY5Y human neuroblastoma cell line were maintained in DMEM/F12 medium with 10% FBS at 37° C. under 5% CO2.

STS Treatments of Mammalian Cells

Primary glia, glioma or neuroblastoma cells were seeded into 96-well microtiter plates at 20,000-30,000 cells/well and incubated for 2 days. Cells were washed with phosphate buffered saline (PBS) prior to treatments. All treatments were performed at 37° C. under 5% $CO_2$. Glucose restriction was done by incubating cells in glucose free DMEM (Invitrogen) supplemented with either low glucose (0.5 g/L) or normal glucose (1.0 g/L) for 24 hours in 1% serum. Serum restriction was done by incubating cells in DMEM/F12 with either 10% or 1% FBS for 24 hours.

In Vitro Drug Treatments

Cyclophosphamide (CP, Sigma) was used for in vitro chemotherapy studies. Following STS treatments, cells were incubated with varying concentrations of cyclophosphamide (6-15 mg/ml) for 10 hours in DMEM/F12 with 1% FBS. Survival was determined by the MTT/LDH assay and presented as percent ratio of treated to control.

Stress Resistance in Mice

A/J, CD-1 and athymic Nude/nu mice, were used. Six week old female A/J mice (Harlan, Italy), weighing 15-18 g, and four week old female athymic (Nude-nu) mice (Harlan), weighing 20-22 g, were starved for 48 hours and then i.v. injected with 80 mg/kg and 100 mg/kg etoposide (Teva Pharma, Holland), respectively. Four week old female CD-1 mice, weighing 18-20 g, were starved for 60 hours and then i.v. injected with 110 mg/kg etoposide. In all experiments the mice were offered food after chemotherapy and were monitored daily for weight loss and general behaviour. Experiments were also performed with different chemotherapy agents cisplatin in CD-1 mice, and doxorubicin in A/J mice.

Differential Stress Resistance in Mice (DSR)

6-7 week old female A/J mice, weighing 15-18 g (Harlan, Italy) were housed in sterile enclosures under specific virus and antigen-free conditions. A/J mice were injected intravenously with murine neuroblastoma NXS2 cell line (200,000/mouse). After tumor cell injection, some groups of animals were starved for 48 hours and then i.v. injected with 80 mg/kg of etoposide, administered as a single dose. Control groups (NXS2 group) of mice without diet starvation were also investigated. To further investigate differential stress resistance, C57BL/B6 mice were injected with B16Fluc melanoma cells. Prior to injection, cells were washed and resuspended in sterile saline. Each mouse received $2 \times 10^5$ cells in 100 µl followed by another 100 µl of sterile saling to wash the remaining cells in the tail. Mice were randomly selected and followed throughout the experiment. Bioluminescence imaging were performed at USC Small animal imaging center. Signal intensity was quantified (Units of photon/S/$cm^2$/steridian).

Results

See FIGS. 31-35.

CONCLUSIONS

A short-term starvation (STS) can induce stress resistance against chemo-toxicity in vitro and in vivo. STS induced stress resistance can be applied to various common chemotherapies. STS imparted differential stress resistance (DSR) against chemo-drugs in mammalian cells, and tumor-bearing mice. STS could sensitize cancer cells to chemotherapy.

All publications cited herein are incorporated by reference in their entirety.

What is claimed is:
1. A method of protecting an animal or human against chemotherapy or radiotherapy, comprising:
administering to an animal or human, prior to chemotherapy or radiotherapy, a diet capable of providing nutrition while providing no more than 11 kcal energy per kg body weight of the animal or human per day, and no more than 0.4 g protein per kg body weight of the animal or human per day, thereby protecting the animal or human against chemotherapy, radiotherapy, oxidative stress, or aging, wherein no more than half of the energy is in carbohydrates if carbohydrates are present in the diet.

2. The method of claim 1, wherein the diet is capable of providing no more than 700 kcal total energy per day.

3. The method of claim 1, further comprising exposing the animal or human to chemotherapy or radiotherapy.

4. The method of claim 3, wherein the diet is administered to the animal or human for 3 to 10 consecutive days prior to the exposing step, 24 hours following the exposing step, or a combination thereof.

5. The method of claim 1, wherein the diet is administered every third meal or every 3 to 10 days to protect the animal or human against chemotherapy or radiotherapy.

6. A method of protecting an animal or human against chemotherapy or radiotherapy:

administering to the animal or human, 3 to 10 days prior to chemotherapy or radiotherapy, a diet capable of providing nutrition while providing no more than 11 kcal energy per kg body weight of the animal or human per day, and no more than 0.4 g protein per kg body weight of the animal or human per day, thereby protecting the animal or human against chemotherapy or radiotherapy, wherein no more than half of the energy is in carbohydrates if the carbohydrates are present in the diet; and exposing the animal or human to chemotherapy or radiotherapy.

7. The method of claim 6, wherein the diet is capable of providing no more than 700 kcal total energy per day.

8. The method of claim 6, wherein the diet is administered to the animal or human for 24 hours following the exposing step.

9. The method of claim 6, wherein the diet is administered to the animal or human for 3 to 10 consecutive days.

\* \* \* \* \*